United States Patent [19]
Fujiwara et al.

[11] Patent Number: 5,948,786
[45] Date of Patent: Sep. 7, 1999

[54] PIPERIDINYLPYRIMIDINE DERIVATIVES

[75] Inventors: Norio Fujiwara, Yao; Yutaka Ueda, Ibaraki; Shinobu Murata, Toyonaka; Fumiyo Hirota; Hajime Kawakami, both of Nishinomiya; Hitoshi Fujita, Nishinomiya, all of Japan

[73] Assignee: Sumitomo Pharmaceuticals Company, Limited, Osaka, Japan

[21] Appl. No.: 09/069,085

[22] Filed: Apr. 29, 1998

Related U.S. Application Data

[63] Continuation-in-part of application No. 08/911,001, Aug. 14, 1997, which is a continuation-in-part of application No. 08/837,453, Apr. 18, 1997, abandoned, which is a continuation-in-part of application No. 08/722,548, Sep. 27, 1996, abandoned.

[30] Foreign Application Priority Data

Apr. 12, 1996 [JP] Japan .................................. 8-115556

[51] Int. Cl.$^6$ ...................... A61K 31/505; C07D 405/14; C07D 239/02; C07D 401/00
[52] U.S. Cl. ......................... 514/274; 514/275; 544/330; 544/331; 544/332; 544/316
[58] Field of Search ..................... 544/316, 330, 544/331, 332; 514/274, 275

[56] References Cited

U.S. PATENT DOCUMENTS 5,763,448 6/1998 Carling et al. ..................... 514/274

FOREIGN PATENT DOCUMENTS 49-11710 3/1974 Japan .
9426733 11/1994 WIPO .

OTHER PUBLICATIONS

*Chem. Pharm. Bull.*, "Synthesis of Piperidine Derivatives with a Quinazoline Ring System as Potential Antihypertensive Agents", vol. 34 (1986), Haruki Takai et al.

*Primary Examiner*—Mukund J. Shah
*Assistant Examiner*—Bruck Kifle
*Attorney, Agent, or Firm*—Sughrue, Mion, Zinn, Macpeak & Seas, PLLC

[57] ABSTRACT

A compound of formula (1)

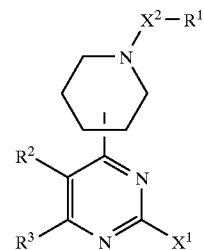

(1)

wherein $X^1$ is amino or hydroxyl, $X^2$ is carbonyl and the like $R^1$ is an alkyl, an aryl and the like, $R^2$ is hydrogen and the like, and $R^3$ is an alkyl and the like, or a pharmaceutical acceptable salt thereof is effective for inibiting the production and/or secretion of tumor necrosis factor in a patient in need of such inhibition.

8 Claims, No Drawings

PIPERIDINYLPYRIMIDINE DERIVATIVES

CROSS-REFERENCE TO RELATED APPLICATION

This is a continuation-in-part application of patent application Ser. No. 08/911,001 filed on Aug. 14, 1997, that is continuation-in-part Ser. No. 08/837,453, filed on Apr. 18, 1997 now abandoned, that is continuation-in-part application of patent application Ser. No. 08/722,548, filed on Sep. 27, 1996, now abandoned.

All the contents of those related applications should be incorporated herein by reference.

FIELD OF THE INVENTION

The present invention relates to a method for inhibiting the production and/or secretion of tumor necrosis factor, a pharmaceutical composition inhibiting the production and/or secretion of tumor necrosis factor and novel piperidinylpyrimidine derivatives.

BACKGROUND ART

Tumor necrosis factor alpha (hereinafter abbreviated as TNF α) is a peptide of 157 amino acids, having a molecular weight of about 17,000. TNF α is a cytokine produced from various cells including activated macrophages.

Although TNF α is a cytokine showing cytotoxicity against several kinds of tumor cells, subsequent studies revealed that TNF α has various other activities, and the activities are not only limited to tumor cells but extend to many other normal cells. The diverse effects of TNF α are markedly enormous. Examples of the TNF α activities are suppression of lipoprotein lipase activity in adipocytes; expression of human leukocyte antigens (HLA) on blood endothelial cells and fibroblasts; interleukin-1 production by fibroblasts or macrophages; activation of macrophages; induction of colony stimulating factor by fibroblasts, endothelial cells or some tumor cells; inhibition of synthesis of proteoglycans and stimulation of their resorption in cartilage; activation of neutrophils and generation of superoxide; production of procoagulant factor by blood endothelial cells; proliferation of fibroblasts; IL-6 production by fibroblasts; injury of blood endothelial cells; and the like. According to recent studies, TNF α is recognized as a cytokine involved broadly in vital protection through inflammation and immune response, as described in Vassalli, P., Ann. Rev. Immunol., 10, 411–452 (1992).

On the other hand, it has been found that continuous or excessive production of TNF α can result in extreme action on normal cells which can cause various diseases. It is also reported in Beutler B., Greenwald D., Hulmes J. D. et al., Nature, 316, 552–554 (1985), Kawakami, M., SEIKA-GAKU (Biochemistry), 59, 1244–1247 (1987) that TNF α is also known as cachectin, which induces cachexia in cancer or infectious diseases (involving catabolic acceleration of total metabolism leading to extreme wasting).

TNF α is considered to be one of the causes of septic shock and there are many reports on the effectiveness of an anti-TNF α antibody in septic shock (Starnes, H. F. Jr., Pearce, M. K., Tewari, ., Yim, J. H., Zou, J. C., Abrams, J. S., J. Immunol., 145, 4185–4191 (1990), Beutler, B., Milsark, I. W., Cerami, A. C., Science, 229, 869–871 (1985), Hinshaw, L. B., Tekamp-Olson, P., Chang, A. C. K. et al., Circ. Shock, 30, 279–292 (1990)).

An increased level of TNF α is also found in the synovial fluid or blood from rheumatoid arthritis patients, as reported in Tetta, C., Camussi, G., Modena, V., Vittorio, C. D., Baglioni, C., Ann. Rheum. Dis., 49, 665–667 (1990).

In recent years, acquired immunodeficiency syndrome (AIDS) has been explosively prevalent all over the world. AIDS is a disease mainly caused by infection with human immunodeficiency virus-1 (HIV). HIV-infected patients are often complicated by opportunistic infections, Kaposi's sarcoma, neurological disorders (CNS disorders), and/or cachexia, etc., and those diseases often cause fatal.

HIV is a retrovirus classified in the subfamily of Lentiviruses. CD4-positive T lymphocytes and monocytes are the major cellular targets for HIV infection, but HIV also infects other various cells such as macrophages, glial cells and the like. HIV-1 infects cells through binding to specific receptors such as CD4, CXCR4, CCR5 and so on that are expressed on the cell surface. As with the life cycle of other retroviruses, HIV-1 RNA in the cells was reverse-transcribed by HIV-1 reverse transcriptase and a viral DNA was integrated into a genomic DNA of the infected cell by HIV-1 integrase. The integrated DNA, called a provirus, has a unique sequence called long terminal repeat (LTR) at both ends. It is revealed that the LTR region is crucial for the transcription activation and the replication of HIV-1.

Control of HIV-1 transcription is complex and involves the interplay of cis-acting viral elements, viral transactivators, and several cellular proteins. These interactions regulate basal levels and induce high levels of viral gene expression. The site of viral RNA synthesis is the cell nucleus, and the template is proviral DNA integrated into host cell genome. Retroviral LTRs are divided into three regions, called U3, R, and U5 respectively. They have distinct functions in transcription. The U3 region of HIV contains basal promoter elements, including a TATAA box for initiation by host cell RNA polymerase II and sites for binding the cellular transcription factor SP1. Additional cis-acting sequences in this region are recognized by several cellular factors that modulate transcription by influencing the rate of initiation. Initiation of viral RNA takes place at U3/R border of the 5'LTR, and 5' ends of these viral transcripts are posttranscriptionally capped with 7-methylguanosine by cellular enzymes.

It is known that in T cells or macrophages stimulated by, e.g., antigens, a lipopolysaccharide, which is one of the main constituents of bacteria, proinflammatory cytokines (TNF α, IL-1 or IL-6) or PMA, signal transduction pathways in cells are activated and unique sets of activated transcription factors increase in the nucleus to accelerate the transcription of HIV (Osborn, L. et al., Proc. Natl. Acad. Sci., USA, 86, 2336–2340 (1989), Poli, G. et al., J. Exp. Med., 172, 151–158 (1990), Poli, G. et al., Proc. Natl. Acad. Sci., USA, 87, 782–785 (1990)). The viral transactivator Tat functions through a cis-acting sequence, designated the tat-response element (TAR), which is located in R region. R-U5 is in the leader sequence of the full-length viral transcript as well as all spliced transcripts. The 3' ends of viral transcripts are defined by the R/U5 border in 3'LTR; signals in U3 and R (AAUAAA and a downstream GU-rich element) are recognized by cellular functions which add poly-A tails to the 3' ends of viral transcripts. Although both LTRs are identical in sequence, retrovirus have mechanisms by which the 5' LTR is used initiation and the 3' LTR signals addition of poly-A tails (Paul A. Luciw; Virology, Third edition chapter 60 Human Immunodeficiency Viruses and Their Replication Field; Lippincott-Raven Publishers, Philadelphia (1996) 1881). The newly transcribed viral RNA comprises regions encoding proteins constituting HIV and is translated into the proteins to produce new virions together with the viral RNA.

It is considered that an agent that inhibits the functions of Tat, the transcription factors, or inhibits their upstream signaltransducers can be a potential inhibitor for HIV-1 replication. As a result, such an agent can be an effective medicine for treating HIV-1 infection.

In several longitudinal studies of HIV-1 LTR sequence in vitro and in vivo, it was shown that the sequence diversity was found in LTR region of laboratory-adapted and clinical isolated viruses, but it is also reported that several binding sites of transcription factor and TAR are highly preserved. Therefore, the rationale of the medicines described above should be extended to most of HIV-1 infection.

It is interesting to note that some of the binding sites of those transcription factors contained in the LTR sequence are also found in the enhancer/promoter region of viral genes, such as Rous sarcoma virus, human cytomegalovirus and simian virus, and in the enhancer/promoter region of various vital genes including TNF α (Shakhov, A. N., J. Exp. Med., 171, 35–47 (1990)). It is known that the corresponding transcription factors take some role in activation of the transcription of these genes. It is then suggested that some inhibitors of TNF α production may reduce not only the transcription of TNF α but HIV by interfering directly/indirectly with the activity of these transcription factors (Li, C. J. et al., Trends in Microbiology, 2(5), 164–169 (1994)).

On the other hand, an abnormally high concentration of TNF α in blood of AIDS patients is reported (Dezube, B. J. et al., J. Acquir, Immune Defic. Syndr. 5, 1099–1104 (1992), Wright, S. C. et al., J. Immunol, 141(1), 99–104 (1988)). The excessive production of TNF α in the AIDS patients is another evidence suggesting that TNF α would be associated with pathological conditions including cachexia, apoptosis of T cells, abnormal B cells proliferation, etc., in addition to the activity of accelerating HIV proliferation. By reducing the level (concentration) of TNF α in a host, an inhibitor of TNF α or an inhibitor of production and/or secretion of TNF α is therefore expected to show not only the activity of inhibiting HIV replication but the activity of improving the pathological conditions of AIDS described above.

In addition, there are many other diseases wherein a high concentration of TNF α is found in blood and/or tissue, e.g., osteoarthritis (Venn, G., Nietfeld, J. J., Duits, A. J., Brennan, F. M., Arner, E., Covington, M., Billingham, M. E. J., Hardingham, T. E., Arthritis Rheum., 36(6), 819–826 (1993)); multiple sclerosis (Sharief, M. K., Hentges, R., N. Engl. J. Med., 325 (7), 467–472 (1991)); Kawasaki disease (Matsubara, T., Furukawa, S., Yabuta, K., Clin. Immunol. Immunopathol., 56, 29–36 (1990)); inflammatory bowel diseases such as ulcerative colitis or Crohn's disease (Murch, S., Walker-Smith, J. A., Arch. Dis. Child, 66, 561 (1991); Maeda, Y., SHOKAKI-TO-MEN-EKI (Digestive Organ and Immunity), 22, 111–114 (1989)); Behcet disease (Akoglu, T., Direskeneli, H., Yazici, H., Lawrence, R., J. Rheumatol., 17, 1107–1108 (1990)); systemic lupus erythematosus (SLE) (Maury, C. P. J., Teppo, A-M., Arthritis Rheum., 32, 146–150 (1989)); graft versus host disease (GvHD) (Nestel, F. P., Price, K. S., Seemayer, T. A., Lapp, W. S., J. Exp. Med., 175, 405–413 (1992)); multiple organ failure (Fujiwara, T., Kawakami, M., RINSHO-I (Clinician), 17 (10), 2006–2008 (1991)); malaria (Grau, G. E., Fajardo, L. F., Piguet, P. F., et al., Science, 237, 1210–1212 (1987)); meningitis (Waage, A., Halstensen, A., Espevik, T., Lancet, I, 355–357 (1987)); hepatitis (Sugano, K., KANZO (Liver), 33, 213–218 (1992)); non-insulin-dependent diabetes mellitus (NIDDM) (Hotamisligil, G. S., Shargill, N. S., Spiegelman, B. M., Science, 259, 87–91 (1993), asthma, adult respiratory distress syndrome (ARDS), tuberculosis, atherosclerosis, Alzheimer's disease, etc.

As seen from the above publications, it is understood that excessive production of TNF α sometimes adversely affects the living body. Therefore, further investigation is desired to develop an inhibitor of production and/or secretion of TNF α or TNF α inhibitors available for the treatment of these diseases.

As compounds and factors showing an activity of inhibiting TNF α, pentoxifylline, glucocorticoid, protease inhibitors, phospholipase A2 inhibitors, lipoxygenase inhibitors, platelet activating factor (PAF) antagonists, radical scavengers, prostaglandin $F_2$ or $I_2$, an anti-TNF α antibody, thalidomide, etc. are known. However, these compounds or factors are accompanied by side effects because of a diversity of their pharmacological activities. It is therefore required to develop highly safe compounds based on a novel mechanism.

TNF β (lymphotoxin, LT) is also known as a factor belonging to the same family of TNF α. TNF β is a glycoprotein composed of 171 amino acids, and has homology with TNF α both in gene structure and amino acid sequence. Further, it is known that both TNF β and TNF α commonly share the same receptors and have identical biological activities. The enhancer/promoter regions at the upstream of TNF α and TNF β genes have a common partial sequence to which the same transcriptional factors possibly bind. TNF β may be produced by stimulation with antigen, phorbol ester and mitogen which are known to induce the production of TNF α. Thus, factors or compounds having an inhibitory activity on the production of TNF α may also exhibit an inhibitory activity on TNF β (Jongeneel, C. V., Tumor Necrosis Factors; Beutler, B. Ed., Raven Press: New York, 1992, pp. 539–559, Poter, A. G., FEMS Microbiol. Immunol., 64, 193–200 (1990), Pauli, U., Critical Rev. Eukaryotic Gene Expression, 4, 323–344 (1994)).

On the other hand, piperidinylpyrimidine derivatives are described in WO 9426733 and Japanese Patent KOKOKU No. 49–11710. However, these publications do not suggest any TNF α inhibitory activities. In the description of Chem. Pharm. Bull., 34 (5), 1907–1916 (1986), which is limited to use as intermediates for synthesis, discloses compounds represented by the following formula:

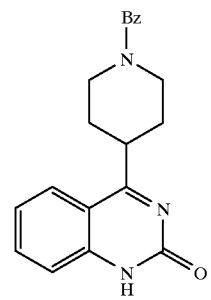

(wherein Bz is benzoyl.). No utility of these compounds is disclosed anywhere in the report.

SUMMARY OF THE INVENTION

This invention provides a method for inhibiting the production and/or secretion of tumor necrosis factor, a pharmaceutical composition inhibiting the production and/or secretion of tumor necrosis factor and novel piperidinylpyrimidine derivatives having an excellent activity of inhibiting the fornation and/or secretion of TNF α.

The present invention relates to a method for inhibiting the production and/or secretion of tumor necrosis factor in a patient in need of such inhibition, which comprises administering to a patient a pharmaceutically effective amount of a compound represented by formula (1)

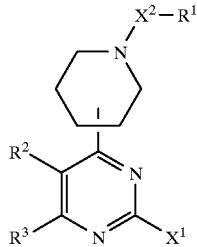

(1)

wherein $X^1$ is amino or hydroxy;

$X^2$ is carbonyl (—(CO)—), carbonyloxy (—(CO)O—), carbonylamino (—(CO)NH—), or sulfonyl (—(SO$_2$)—);

$R^1$ is an alkyl, a cycloalkyl, an aryl, a substituted aryl, a heteroaryl, or —(CH$_2$)$_m$-A, wherein m is an integer selected from the group consisting of 1, 2, 3, 4, 5, 6, 7, 8, 9 and 10, and A is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl;

$R^2$ is hydrogen, an alkyl, or an aryl;

$R^3$ is an alkyl, an aryl, a substituted aryl, a heteroaryl, or —(CH$_2$)$_{m'}$-A', wherein m' is an integer selected from the group consisting of 1, 2, 3, and 4, and A' is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl;

or $R^2$ and $R^3$ are combined together with the pyrimidine ring to form quinazoline, a substituted quinazoline, pyridopyrimidine or a substituted pyridopyrimidine;

or a pharmaceutically acceptable salt thereof.

This invention also relates to a pharmaceutical composition comprising a compound represented by the formula (1);

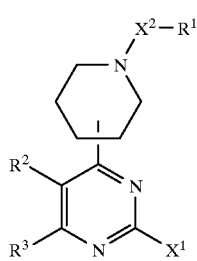

(1)

wherein $X^1$ is amino or hydroxy;

$X^2$ is carbonyl (—(CO)—), carbonyloxy (—(CO)O—), carbonylamino (—(CO)NH—), or sulfonyl (—(SO$_2$)—);

$R^1$ is an alkyl, a cycloalkyl, an aryl, a substituted aryl, a heteroaryl, or —(CH$_2$)$_m$-A, wherein m is an integer selected from the group consisting of 1, 2, 3, 4, 5, 6, 7, 8, 9 and 10, and A is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl;

$R^2$ is hydrogen, an alkyl, or an aryl;

$R^3$ is an alkyl, an aryl, a substituted aryl, a heteroaryl, or —(CH$_2$)$_{m'}$-A', wherein m' is an integer selected from the group consisting of 1, 2, 3, and 4, and A' is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl;

or $R^2$ and $R^3$ are combined with the pyrimidine ring to form quinazoline, a substituted quinazoline, pyridopyrimidine or a substituted pyridopyrimidine;

or a pharmaceutically acceptable salt thereof.

This invention also relates to a piperidinylpyrimidine derivative represented by the formula (1-a)

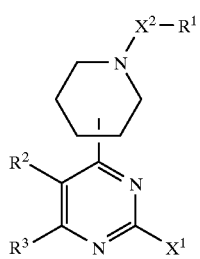

(1-a)

wherein (1) $X^1$ is amino or hydroxy;

$X^2$ is carbonyl (—(CO)—), carbonyloxy (—(CO)O—), carbonylamino (—(CO)NH—), or sulfonyl (—(SO$_2$)—);

$R^1$ is an alkyl, a cycloalkyl, an aryl, a substituted aryl, a heteroaryl, or —(CH$_2$)$_m$-A, wherein m is an integer selected from the group consisting of 1, 2, 3, 4, 5, 6, 7, 8, 9, and 10, and A is a halogen atom, a cycloalkyl, hydroxy, amino, cyano, nitro, carboxyl, an alkoxy, an alkylthio, an alkokycarbonyl, an aryloxycarbonyl, an alkyloxycarbonylamino, an alkylamino, a dialkylamino, a saturated heterocyclic, an aryl, a substituted aryl or a heteroaryl;

$R^2$ is hydrogen, an alkyl, or an aryl;

$R^3$ is an alkyl, an aryl, a substituted aryl, a heteroaryl, or —(CH$_2$)$_{m'}$-A', wherein m is an integer selected from the group consisting of 1, 2, 3, and 4, and A is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl; or (2) $X^1$ is amino;

$X^2$ is carbonyl (—(CO)—);

$R^1$ is an $C_{6-10}$ alkyl, a cycloalkyl, an aryl substituted by two or three halogen atoms, 2, 3-methylenedioxyphenyl, 3,4-methylenedioxyphenyl, a $C_{7-15}$ aralkyl or —(CH$_2$)$_m$-A, wherein m is an integer selected from the group consisting of 6, 7, 8, 9, and 10, and A is a halogen atom, a cycloalkyl, hydroxy, amino, cyano, carboxyl, an alkoxy, an alkoxycarbonyl, an aryloxycarbonyl, an alkyloxycarbonylamino, an alkylamino, a dialkylamino, a saturated heterocyclic, an aryl or a substituted aryl;

R² and R³ are combined with the pyrimidine ring to form quinazoline, a substituted quinazoline, pyridopyrimidine, or a substituted pyridopyrimidine;

or a pharmaceutically acceptable salt thereof.

A preferred compound is represented by the formula (1-b);

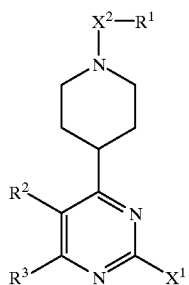

wherein X¹ is amino;

X² is carbonyl (—(CO)—), carbonyloxy (—(CO)O—), or carbonylamino(—CONH—);

R¹ is an alkyl, a cycloalkyl, an aryl, a substituted aryl, a heteroaryl, or —(CH₂)$_m$-A, wherein m is an integer selected from the group consisting of 1, 2, 3, 4, 5, 6, 7, 8, 9 and 10, and A is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl;

R² is hydrogen or an alkyl;

R³ is an aryl, a substituted aryl, a heteroaryl, or —(CH₂)$_{m'}$-A', wherein m' is an integer selected from the group consisting of 1 and 2, and A' is an aryl, a substituted aryl or a heteroaryl;

or R² and R³ are combined with the pyrimidine ring to form quinazoline, a substituted quinazoline, pyridopyrimidine or a substituted pyridopyrimidine;

or a pharmaceutically acceptable salt thereof.

A preferred compound is represented by formula (1-c),

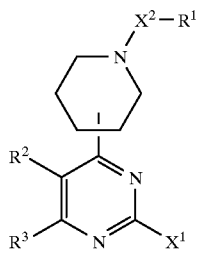

wherein X¹ is amino or hydroxy;

X² is carbonyl (—(CO)—), carbonyloxy (—(CO)O—), carbonylamino (—(CO)NH—), or sulfonyl (—(SO₂)—);

R¹ is an alkyl, a cycloalkyl, an aryl, a substituted aryl, a heteroaryl, or —(CH₂)$_m$-A, wherein m is an integer selected from the group consisting of 1, 2, 3, 4, 5, 6, 7, 8, 9, and 10, and A is a halogen atom, a cycloalkyl, hydroxy, amino, cyano, nitro, carboxyl, an alkoxy, an alkylthio, an alkokycarbonyl, an aryloxycarbonyl, an alkyloxycarbonylamino, an alkylamino, a dialkylamino, a saturated heterocyclic, an aryl, a substituted aryl or a heteroaryl;

R² is hydrogen, an alkyl, or an aryl;

R³ is an alkyl, an aryl, a substituted aryl, a heteroaryl, or —(CH₂)$_{m'}$-A', wherein m' is an integer selected from the group consisting of 1, 2, 3, and 4, and A' is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl;

or a pharmaceutically acceptable salt thereof.

A preferred compound is represented by formula (1-d),

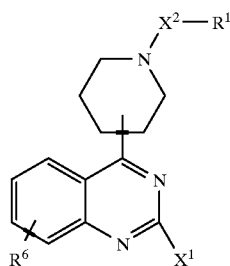

wherein X¹ is amino;

X² is carbonyl (—(CO)—);

R¹ is an C$_{6-10}$ alkyl, a cycloalkyl, an aryl substituted by two or three halogen atoms, 2,3-methylenedioxyphenyl, 3,4-methylenedioxyphenyl, a C$_{7-15}$ aralkyl or —(CH₂)$_m$-A, wherein m is an integer selected from the group consisting of 6, 7, 8, 9, and 10, and A is a halogen atom, a cycloalkyl, hydroxy, amino, cyano, carboxyl, an alkoxy, an alkoxycarbonyl, an aryloxycarbonyl, an alkyloxycarbonylamino, an alkylamino, a dialkylamino, a saturated heterocyclic, an aryl or a substituted aryl;

R⁶ is a halogen atom, an alkyl, an alkoxy, nitro, cyano, carboxyl, hydroxy, amino, trifluoromethyl, an alkylamino, a dialkylamino, an alkanoyl, an alkanoylamino, sulfamoyl, an alkylaminosulfonyl, a dialkylaminosulfonyl or an alkoxycarbonyl;

or a pharmaceutically acceptable salt thereof.

A more preferred compound is represented by formula (1-e),

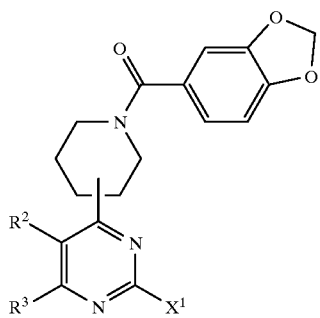

(1-e)

wherein $X^1$ is amino or hydroxy;

$R^2$ is hydrogen, an alkyl, or an aryl;

$R^3$ is an alkyl, an aryl, a substituted aryl, a heteroaryl, or —$(CH_2)_{m'}$-A', wherein m' is an integer selected from the group consisting of 1, 2, 3 and 4, and A' is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl;

or $R^2$ and $R^3$ are combined with the pyrimidine ring to form quinazoline, a substituted quinazoline, a pyridopyrimidine or a substituted pyridopyrimidine;

or a pharmaceutically acceptable salt thereof.

A preferred embodiment included in the formula (1-e) is represented by the formula (1-f).

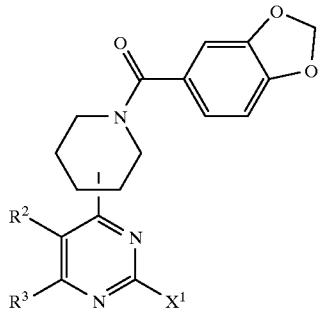

wherein $X^1$ is amino or hydroxy;

$R^2$ is hydrogen, an alkyl, or an aryl;

$R^3$ is an alkyl, an aryl, a substituted aryl, a heteroaryl, or —$(CH_2)_{m'}$-A', wherein m' is an integer selected from the group consisting of 1, 2, 3 and 4, and A' is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl;

or $R^2$ and $R^3$ are combined together with the pyrimidine ring to form quinazoline, a substituted quinazoline, a pyridopyrimidine or a substituted pyridopyrimidine;

or a pharmaceutically acceptable salt thereof.

This invention also provides a method for inhibiting retrovirus long terminal repeat transcriptional activation in a patient in need of such inhibition, which comprises administering to a patient a pharmaceutically effective amount of a compound represented by formula (1-e)

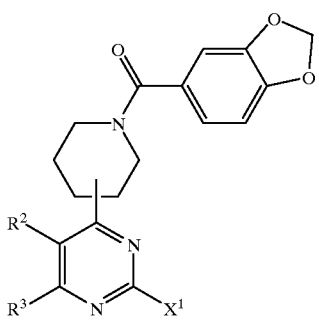

(1-e)

wherein $X^1$ is amino or hydroxy;

$R^2$ is hydrogen, an alkyl, or an aryl;

$R^3$ is an alkyl, an aryl, a substituted aryl, a heteroaryl, or —$(CH_2)_{m'}$-A', wherein m' is an integer selected from the group consisting of 1, 2, 3 and 4, and A' is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl;

or $R^2$ and $R^3$ are combined with the pyrimidine ring to form quinazoline, a substituted quinazoline, a pyridopyrimidine or a substituted pyridopyrimidine;

or a pharmaceutically acceptable salt thereof.

This invention also provides a method for inhibiting human immunodeficiency virus-1 long terminal repeat transcriptional activation in a patient in need of such inhibition, which comprises administering to a patient a pharmaceutically effective amount of a compound represented by formula (1-e)

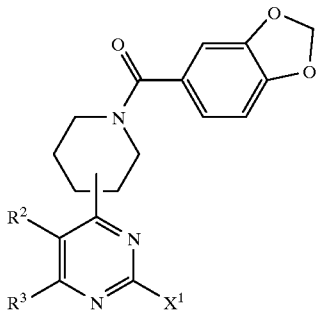

(1-e)

wherein $X^1$ is amino or hydroxy;

$R^2$ is hydrogen, an alkyl, or an aryl;

$R^3$ is an alkyl, an aryl, a substituted aryl, a heteroaryl, or —$(CH_2)_{m'}$-A', wherein m' is an integer selected from the group consisting of 1, 2, 3 and 4, and A' is a halogen atom, a cycloalkyl, hydroxy, amino, cyano, nitro, carboxyl, an alkoxy, an alkylthio, an alkoxycarbonyl, an aryloxycarbonyl, an alkyloxycarbonylamino, an alkylamino, a dialkylamino, a saturated heterocyclic, an aryl, a substituted aryl or a heteroaryl;

or $R^2$ and $R^3$ are combined with the pyrimidine ring to form quinazoline, a substituted quinazoline, a pyridopyrimidine or a substituted pyridopyrimidine;

or a pharmaceutically acceptable salt thereof.

DETAILED DESCRIPTION OF THE INVENTION

The functional groups in the present invention represented by the formulae (1), (1-a), (1-b), (1-c), (1-d), (1-e) and (1-f) are described below.

The term "alkyl" as used herein refers to a straight or branched chain hydrocarbon group having 1 to 10 carbon atoms. Examples of the alkyl are methyl, ethyl, propyl, butyl, pentyl, hexyl, heptyl, octyl, nonanyl, decanyl, 1-methylethyl, 1-methylpropyl, 2-methylpropyl, 1,1-dimethylethyl, 1-methylbutyl, 2-methylbutyl, 3-methylbutyl and the like.

The term "$C_{6-10}$alkyl" as used herein refers to a straight chain hydrocarbon group having 6 to 10 carbon atoms. Examples of the $C_{6-10}$alkyl are hexyl, heptyl, octyl, nonanyl, decanyl, and the like.

The term "cycloalkyl" as used in herein refers to a saturated hydrocarbon group possessing at least one carbocyclic ring, the ring containing 3 to 7 carbon atoms. Examples of the cycloalkyl are cyclopropyl, cyclobutyl, cyclopentyl cyclohexyl and the like.

The term "alkenyl" as used herein refers to a hydrocarbon group having 2 to 10 carbon atoms possessing at least one double bond. Examples of the alkenyl are ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl 3-methyl-2-butenyl and the like.

The term "alkoxy" as used herein refers to a monovalent substituent comprising an alkyl group having 1 to 6 carbon atoms linked through an ether oxygen having its free valence bond from the ether oxygen. Examples of the alkoxy are methoxy, ethoxy, propoxy, 1-methylethoxy, butoxy, 1-methylpropoxy, 2-methylpropoxy, pentyloxy, 1-methylbutoxy, 2-methylbutoxy, 3-methylbutoxy, 1,1-dimethylpropoxy, 1,2-dimethylpropoxy, 2,2-dimethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethyl-1-methylpropoxy 1-ethyl-2-methylpropoxy and the like.

The term "alkylthio" refers to a monovalent substituent comprising an alkyl group having 1 to 6 carbon atoms linked through an ether sulfur having its free valence bond from the ether sulfur. The examples of the alkylthio are methylthio, ethylthio, propylthio, 1-methylethylthio, butylthio, 1-methylpropylthio, 2-methylpropylthio, pentylthio, 1-methylbutylthio, 2-methylbutylthio, 3-methylbutylthio, 1,1-dimethylpropylthio, 1,2-dimethylpropylthio, 2,2-dimethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethyl-1-methylpropylthio 1-ethyl-2-methylpropylthio and the like.

The term "alkoxycarbonyl" refers to a monovalent substituent having the formula alkyl-O—(C=O)—. Examples of the alkoxycarbonyl are methoxycarbonyl, ethoxycarbonyl, propoxycarbonyl, 1-methylethoxycarbonyl, butoxycarbonyl, 1,1-dimethylethoxycarbonyl and the like.

The term "alkylamino" refers to a monosubstituted derivative of ammonia, wherein a hydrogen of ammonia is replaced by an alkyl group having 1 to 4 carbon atoms and examples of the alkylamino are methylamino, ethylamino, propylamino, 1-methylethylamino, butylamino, 1,1-dimethylethylamino and the like.

The term "dialkylamino" refers to a disubstituted derivative of ammonia, wherein two hydrogens of ammonia are replaced by alkyl groups having 1 to 4 carbon atoms and examples of the alkylamino are N,N-dimethylamino, N,N-diethylamino, N,N-dipropylamino, N-methyl-N-ethylamino, N,N-dibutylamino, N-methyl-N-(1,1-dimethylethyl)amino and the like.

The term "aryl" as used herein refers to an aromatic hydrocarbon possessing at least one hydrocarbon ring having up to 10 carbon atoms and examples of the aryl are phenyl, 1-naphthyl, 2-naphthyl and the like.

The term "aryloxycarbonyl" refers to a monovalent substituent having the formula aryl-O—(C=O)—. Examples of the group includes an aryloxycarbonyl group having 7 to 13 carbon atoms and is specifically exemplified by phenoxycarbonyl.

The term "alkyloxycarbonylamino" refers to a primary or secondary amine, which is replaced by a substituent having the formula alkyl-O—(C=O)— and examples of the alkyloxycarbonylamino are t-butoxycarbonylamino and the like.

Examples of the halogen atom are fluorine, chlorine, bromine and iodine atoms.

The substituent of the substituted aryl may be at one or more of the carbons of the aromatic ring. If the aryl group has two or more substituents, the substituents may be same or different from each other. Examples of the substituent of the substituted aryl are a halogen atom, an alkyl, an alkoxy, nitro, cyano, carboxyl, hydroxy, amino, trifluoromethyl, an alkylamino, a dialkylamino, an alkanoyl, an alkanoylamino, sulfamoyl, an alkylaminosulfonyl, a dialkylaminosulfonyl, an alkoxycarbonyl and the like. Furthermore, the substituents adjacent to each other may be combined together to form an alkylenedioxy group such as 2,3-methylenedioxy, 3,4-methylenedioxy, 2,3-ethylenedioxy, 3,4-ethylenedioxy, or to form a heterocyclic group fused with an aryl ring such as 2,3-dihydrobenz[b]furan.

The term "alkanoyl" refers to the radical formed by removal of the hydroxy function from a straight or branched alkanoic acid having 1 to 6 carbon atoms and examples are formyl, acetyl, propanoyl, butanoyl, valeryl, isovaleryl, pivaloyl, hexanoyl and the like.

The term "alkanoylamino" refers to a primary or secondary amine, wherein a hydrogen of the amine is replaced by an alkanoyl group having 1 to 6 carbon atoms. Examples of the alkanoylamino are formylamino, acetylamino, propanoylamino, butanoylamino, valerylamino, isovalerylamino, pivaloylamino, hexanoylamino and the like.

The term "alkylaminosulfonyl" refers to a monovalent substituent comprising an alkylamino group linked through a sulfonyl group having its free valence bond from the sulfur atom and examples of the alkylaminosulfonyl are methylaminosulfonyl, ethylaminosulfonyl, propylaminosulfonyl, 1-methylethylaminosulfonyl, butylaminosulfonyl, 1,1-dimethylethylaminosulfonyl and the like.

The term "dialkylaminosulfonyl" refers to a monovalent substituent comprising an dialkylamino group linked through the sulfonyl group having its free valence bond from the sulfur atom and examples of the dialkylaminosulfonyl are N,N-dimethylaminosulfonyl, N,N-diethylaminosulfonyl, N,N-dipropylaminosulfonyl, N-methyl-N-ethylaminosulfonyl, N,N-dibutylaminosulfonyl, N-methyl-N-(1,1-dimethylethyl)aminosulfonyl and the like.

The term "heteroaryl" refers to a unsaturated aromatized heterocyclic group such as a monocyclic or bicyclic heteroaryl group comprising not more than 9 carbon atoms, and 1 to 3 hetero atom(s) selecting from the group of nitrogen, oxygen and sulfur atoms, which may be the same or different. Examples of heteroaryl are 2-pyridyl, 3-pyridyl, 4-pyridyl, 2-pyrimidinyl, 4-pyrimidinyl, 5-pyrimidinyl, 2-thiazolyl, 4-thiazolyl, 5-thiazolyl, 2-oxazolyl, 4-oxazolyl, 5-oxazolyl, 3-isoxazolyl, 4-isoxazolyl, 5-isoxazolyl, 3-isothiazolyl, 4-isothiazolyl, 5-isothiazolyl, 2-furyl, 3-furyl, 2-imidazolyl, 4-imidazolyl, 2-thienyl, 3-thienyl, 2-pyrrolyl, 3-pyrrolyl, 1-pyrazolyl, 3-pyrazolyl, 4-pyrazolyl, 2-pyrazinyl, 3-pyridazinyl, 4-pyridazinyl, 1H-1,2,4-triazol-1-yl, 1H-1,2,4-triazol-3-yl, 1H-1,2,4-triazol-5-yl, 3-oxadiazolyl, 5-oxadiazolyl, 2-thiazolyl, 4-thiazolyl, 5-thiazolyl, 4-benzo[b]furan, 5-benzo[b]furan, 6-benzo[b]furan, 7-benzo[b]furan, 4-benzimidazole, 5-benzimidazole, 4-benzothiazole, 5-benzothiazole, 6-benzothiazole, 7-benzothiazole, 4-benzoxazole, 5-benzoxazole, 6-benzoxazole, 7-benzoxazole and the like.

The term "saturated heterocyclic" refers to a monocyclic saturated heterocyclic group comprising not more than 6 carbon atoms and one or two hetero atom(s) selecting from the group of nitrogen, oxygen and sulfur atoms, which may be the same or different, and preferred embodiments include a 5- or 6-membered saturated heterocyclic. Examples of the 5-membered saturated heterocyclic group are 1-pyrrolidinyl, 2-pyrrolidinyl, 3-pyrrolidinyl, 2-oxoranyl, 3-oxoranyl, 2-thioranyl and 3-thioranyl. Examples of the 6-membered saturated heterocyclic group are piperidino, 2-piperidyl, 3-piperidyl, 4-piperidyl, 1-piperazinyl, 2-piperazinyl, 2-tetrahydropyranyl, 3-tetrahydropyranyl, 4-tetrahydropyranyl, morpholino, 2-morpholinyl, 3-morpholinyl and the like.

The monocyclic saturated heterocyclic group may be substituted with an alkyl.

The aromatic group fused together with the pyrimidine ring forms a group having a benzopyrimidine (quinazoline) structure. The fused aromatic group may be substituted with a substituent(s) such as a halogen atom, an alkyl, an alkoxy, nitro, cyano, carboxyl, hydroxy, amino, trifluoromethyl, an alkylamino, a dialkylamino, an alkanoyl, an alkanoylamino, sulfamoyl, an alkylaminosulfonyl, a dialkylaminosulfonyl, an alkoxycarbonyl and the like.

The heteroaryl group fused with the pyrimidine ring forms a group having a pyridopyrimidine structure. Specific examples of such a group include pyrido[2,3-d]pyrimidine, pyrido[3,4-d]pyrimidine, pyrido[4,3-d]pyrimidine and pyrido[3,2-d]pyrimidine. The 5, 6, 7 and 8 positions may be substituted by a substituent such as a halogen atom, an alkyl, an alkoxy, nitro, cyano, carboxyl, hydroxy, amino, trifluoromethyl, an alkylamino, a dialkylamino, an alkanoyl, an alkanoylamino, sulfamoyl, an alkylaminosulfonyl, a dialkylaminosulfonyl, an alkoxycarbonyl and the like.

$R^6$ in the formula (1-d) represents a substituent at the 5, 6, 7 or 8 position of the quinazoline ring. The compound (6) may have one $R^6$ or up to 4 $R^6$'s. If the compound (6) has more than one $R^6$'s, each $R^6$ may be the same or different.

Examples of the pharmaceutically acceptable salt of the invention are a salt with a mineral acid such as hydrogen chloride, hydrogen bromide, sulfuric acid phosphoric acid and the like; a salt with an organic carboxylic acid such as formic acid, acetic acid, fumaric acid, maleic acid, malic acid, tartaric acid, aspartic acid, glutamic acid and the like; a salt with a sulfonic acid such as methanesulfonic acid, benzenesulfonic acid, p-toluenesulfonic acid, hydroxyben-zenesulfonic acid, dihydroxybenzenesulfonic acid and the like; a salt with an alkali metal such as sodium, potassium and the like; a salt with an alkaline earth metal such as calcium, magnesium and the like; a salt with an organic base such as trimethylamine, triethylamine, pyridine, ammonia salts and the like.

The compound of the present invention may have a tautomeric isomer, a stereoisomer, a geometrical isomer or an optical isomer. The present invention includes these isomers.

The compound of the present invention may have hydrates, solvates or crystalline forms. The present invention also includes these forms.

This invention provides a method of treatment of or a pharmaceutical composition for treating a patient having a high concentration of TNF α in blood and/or tissue, such as in septic shock, osteoarthritis, multiple sclerosis, inflammatory bowel diseases such as ulcerative colitis or Crohn's disease, Behcet disease, systemic lupus erythematosus (SLE), graft versus host disease (GvHD), multiple organ failure, malaria, meningitis, hepatitis, non-insulin-dependent diabetes mellitus, asthma, adult respiratory distress syndrome (ARDS), tuberculosis, atherosclerosis, Alzheimer's disease and the like, by administering an effective amount of a compound represented by the formula (1), (1-a), (1-b), (1-c), (1-d), (1-e) or (1-f).

The method for treatment or pharmaceutical composition can be applied for not only limited to human but mammals or animals.

This invention also provide a method of inhibiting retrovirus long terminal repeat transcriptional activation in a mammal or an animal in need of such inhibition comprises administering to the mammal or animal, a pharmaceutically effective amount of a compound of the invention represented by the formula (1-e) or (1-f).

Examples of the above retrovirus are HIV-I (human immunodeficiency virus-1), HTLV-I (human adult T-cell leukemia-I virus), HTLV-II (human adult T-cell leukemia-II virus), ALV (avian leukemia virus), RSV (Rous sarcoma virus), Mason-Phizer mammary tumor-associated virus, simian T-cell lymphotropic virus type I, simian T-cell lymphotropic virus type III, feline leukemia virus, equine infectious anemia virus, caprine arthritis encephalitis virus and the like.

A compound of the present invention that shows an inhibitory effect on the transcription activation of HIV-1 gene and replication of HIV-1 in vitro and is considered to be effective on various type of HIV-1 infections. For example, it could have efficacy to not only a acute/productive infection of HIV-1 but also chronic/latent infection of HIV-1 in which conventional reverse transcriptase inhibitors are not effective. Several in vitro and/or in vivo studies that reflect HIV-1 acute infection, chronic infection and latent infection can show the efficacy of a compound.

It is expected that a compound of the present invention can be used in combination with a HIV-1 reverse transcription inhibitor and/or a HIV-1 protease inhibitor. Such combination therapy is expected to show an excellent efficacy to HIV-1 infection, since a compound of the present invention has a different mode of action against HIV-1 replication from the HIV-1 reverse transcription inhibitor or a HIV-1 protease inhibitor.

A compound of the formula (1-e) or a salt thereof may be used as a combined drug for treatment of HIV-1 patient with a proteinase inhibitor, a reverse transcriptase inhibitor, or/and the like. The most preferred compound of the present invention for the combined drug is a compound represented by the formula (1-f). The most preferred compound of the present invention for the combined drug is 2-amino-4-(4-methoxybenzyl)-6-[1-(3,4-methylenedioxybenzoyl)-4-piperidinyl]pyrimidine or a salt thereof. The proteinase inhibitors, reverse transcriptase inhibitors, or/and the like can be selected one or more for combined drug. Such reverse transcriptase inhibitors include 3'-azido-3'-deoxythymidine, 2',3'-dideoxycytidine, 2',3'-didehydro-3'-deoxythymidine, 11-cyclopropyl-5,11-dihydro-4-methyl-6-H-dipyrido[3,2-b:2',3'-e][1,4]diazepin-6-one, (2R-cis)-4-amino-1-[2-(hydroxymethyl)-1,3-oxathiolan-5-yl]-2(1H)-pyrimidinone, 2',3'-dideoxyinosine, 1-[3-[(1-methylethyl)amino]-2-pyridinyl]-4-[[5-[(methylsulfonyl)amino]-1H-indol-2-yl]carbonyl]piperazine, [[[2-(6-amino-9H-purin-9-yl)ethoxy]methyl]phosphinylidene]bis(oxymethylene)-2,2-dimethylpropanoic acid, (1S-cis)-4-[2-amino-6-(cyclopropylamino)-9H-purin-9-yl]-2-cyclopentene-1-methanol, 1-[3-(ethylamino)-2-pyridinyl]-4-[(5-methoxy-1H-indol-2-yl)carbonyl]piperazine, (S)-6-chloro-4-(cyclopropylethynyl)-1,4,-dihydro-4-(trifluoromethyl)-2H-3,1-benzoxazin-2-one, 5-chloro-2',3'-dideoxy-3'-fluorouridine, (+,−)-2,6-dichloro-alpha-[(2-nitrophenyl)amino]benzeneacetamide, [[2-(6-amino-9H-purin-9-yl)-1-methylethoxy]methyl]phosphonic acid, 1-(ethoxymethyl)-5-(1-methylethyl)-6-(phenylmethyl)-2,4(1H,3H)-pyrimidinedione, (+,−)-alpha-[(2-acetyl-5-methylphenyl)amino]-2,6,-dichlorobenzeneacetamide, 3,4,-dihydro-8-methoxy-2-[(methylthio)methyl]-3-thioxo-1(2H)-quinoxalinecarboxylic acid 1-methylethyl ester, (2R-cis)-4-amino-5-fluoro-1-[2-(hydroxymethyl)-1,3-oxathiolan-5-yl]-2(1H)-pyrimidinone, N-(5-bromo-2-pyridinyl)ethyl]-thiourea, (S)-4,5,6,7-tetrahydro-5-methyl-6-(3-methyl-2-butenyl)imidazo[4,5,1-jk][1,4]benzodiazepine-2(1H)-thione, fluorodideoxyadenosine, [10R-(10alpha, 11beta, 12alpha)]-11,12-dihydro-12-hydroxy-6,6,10,11-tetramethyl-4-propyl-2H,6H,10H-benzo[1,2-b:3,4-b':5,6,b"]tripyran-2-one and the like. Such proteinase inhibitors include [3S-[2[1R*(2R*),2S*], 3alpha, 4abeta, 8abeta]]-N1-[3-[3-[[(1,1-dimethylethyl)amino]carbonyl]octahydro-2(1H)-isoquinolinyl]-2-hydroxy-1-(phenylmethyl)propyl]-2-[(2-quinolinylcarbonyl)amino]butanediamide, [5S-(5R*, 8R*,10R*,11R*)]10-hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid 5-thiazolylmethyl ester, [3S-[2(2S*,3S*), 3alpha, 4abeta, 8abeta]]-N-(1,1-dimethylethyl)decadydro-2-[2-hydroxy-3-[(hydroxy-2methylbenzoyl)amino]-4-(phenylthio)butyl]-3-isoquinolinecarboxamide, [1S- [1alpha(R*), 2alpha]]2,3,5-trideoxy-N-(2,3-dihydro-2-hydroxy-1H-indene-1-yl)-5-[2-[[(1,1-dimethylethyl)amino]carbonyl]-4-(3-pyridinylmethyl)-1-piperazinyl]-2-(phenylmethyl)-D-erythro-pentonamide, [3-[[(4-aminophenyl)sulfonyl](2-methylpropyl)amino]-2-hydroxy-1-(phenylmethyl)propyl]-carbamic acid tetrahydro-3-furanyl ester, [7S-(7R*,10S*, 12R*,13R*)]-12-hydroxy-7-(1-methylethyl)-6,9-dioxo-13-(phenylmethyl)-10-[(2,3,4-trimethoxyphenyl)methyl]-2-oxa-5,8,14-triazapentadecane-15-oic acid 1,1-dimethylethyl ester, [4R-[3[2S*,3S*(R*)],4R*]-N-(1,1-dimethylethyl)-3-[2-hydroxy-3-[[2-[[(5-isoquinolinyloxy)acetyl]amino]-3-(methylthio)- 1-oxopropyl]amino]-1-oxo-4-phenylbutyl]-4-thiazolidinecarboxamide, 4-hydroxy-6-[1-(phenylmethyl)propyl]-3-(1-phenylpropyl)-2H-pyran-2-one, [4R-(4alpha, 5alpha,6beta,7beta)]-1,3-bis(3-aminophenyl)methyl]hexahydro-5,6-dihydroxy-4,7-bis(phenylmethyl)-2H-1,3-diazepin-2-one dimethanesulfonate and the like.

The pharmaceutical composition of the present invention can be administered by conventional dosage forms such as oral, parenteral (including intramuscular, subcutaneous and intravenous), rectal, nasal, topical, implant and the like. The formulations may, where appropriate, be prepared by any of the methods well known in the art of pharmaceutics. All methods include the step of bringing into association the active compound with liquid carriers or finely divided solid carriers or both and then, if necessary, shaping the product into a desired formulation.

For oral administration, the pharmaceutical compositions may take the form of, for example, tablets, capsules(each of which includes sustained release or timed release formulations,), pills, powders, cachets, suppositories and the like. Examples of liquid oral dosage forms are solutions, suspensions and the like. Examples of parenteral preparations are sterile solutions, suspensions, and the like prepared by conventional means with pharmaceutically acceptable excipients such as binding agents (e.g. pregelatinised maize starch, polyvinylpyrrolidone, hydroxypropylmethylcellulose, etc.); fillers (e.g. lactose, microcrystalline cellulose, calcium phosphate, etc.); lubricants (e.g. magnesium stearate, talc, silica, etc.); disintegrants (e.g. potato starch, sodium starch glycollate, etc.); or wetting agents (e.g. sodium lauryl sulphate etc.).

Liquid preparations for oral administration may take the form of, for example, solutions, syrups, or suspensions, or they may be presented as a dry product for constitution with water or other suitable vehicle before use. Such liquid preparations may be prepared by conventional means with pharmaceutical acceptable additives such as suspending agents (e.g. sorbitol syrup, methyl cellulose or hydrogenated edible fats, etc.); emulsifying agents (e.g. lectin, acacia, etc.); non-aqueous vehicles ( e.g. almond oil, oily esters, ethyl alcohol, etc.); and preservatives (e.g. methyl or propyl, p-hydroxybenzoates, sorbic acid, etc.).

For topical administration, the pharmaceutical compositions may take the form of buccal or sublingual tablets, drops or lozenges formulated in a conventional manner.

For topical administration to the epidermis, the compounds may be formulated as creams, gels, ointments, lotions or as transdermal patches. Such compositions may, for example, be formulated with an aqueous or oily base with the addition of suitable thickening, gelling, emulsifying, stabilizing, dispersing, suspending, and/or coloring agents.

The active compounds of the invention may also be formulated as depot preparations. Such long acting formulations may be administered by implantation (for example subcutaneously or intramuscularily) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The active compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or multi-dose containers, with added preservatives. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

The active compounds of the invention may also be formulated in rectal compositions, such as suppositories or retention enemas, e.g. containing conventional suppository bases such as cocoa butter or other glyceride.

For intranasal administration the active compounds may be used, for example, as a liquid spray, as a powder or in the form of drops.

For administration by inhalation the active compounds are conveniently delivered in the form of an aerosol spray presentation from pressurized packs or a nebuliser, with the use of a suitable propellant, e.g. dichlorodifluoromethane, trichlorofluoromethane, dichlorotetrafluoroethane, 1,1,1,2-terafluoroethane, carbon dioxide or other suitable gas. In the case of pressurized aerosol, the dosage unit may be determined by providing a valve to deliver a metered amount. Capsules and cartridges of e.g. gelatin for use in an inhaler or insufflator may be formulated containing a powder mix of an active compound of the invention and a suitable powder base such as lactose or starch.

A convenient unit dose formulation contains the active ingredient in an amount of from about 1 to about 1000 mg.

Any of the pharmaceutical compositions described above may be presented in a conventional manner associated with controlled release forms.

It will be appreciated that the amount of a compound of the formula (1), (1-a), (1-b), (1-c), (1-d), (1-e), or (1-f) required for use in treatment will vary not only with the particular compound selected, but also with the route of administration, the nature of the condition being treated and the age, weight and condition of the patient and ultimately be at the discretion of the attendant physician or veterinarian. In general, the daily dose of the active compound of the invention for adult is selected from the range of from about 10 to about 1000 mg, preferably about 10 to about 500 mg for oral administration and, or from the range of from about 1 to about 100 mg, by single administration or by dividing the dose several times.

The piperidinylpyrimidine derivatives of the present invention may be prepared, e.g., by the following processes.
Process (A)

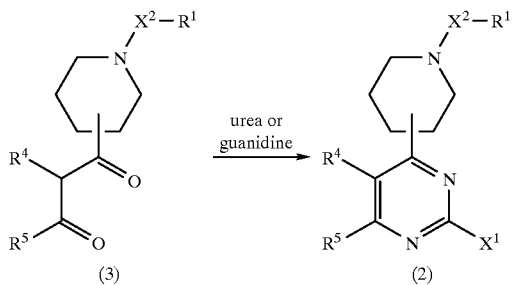

wherein:
$X^1$, $X^2$ and $R^1$ have the same meaning as defined in the formula 1;
$R^4$ is hydrogen atom, an alkyl or an aryl; and,
$R^5$ is an alkyl group, an aryl, a heteroaryl or a group represented by the formula: —$(CH_2)_{m'}$-A', wherein m' and A' have the same meaning as defined in the formula (1).

A compound represented by the formula (2) is included by the formula (1). The compound represented by the formula (2) may be prepared by treating a 1,3-diketone compound represented by the formula (3) with urea or guanidine either in the presence or absence of a base. The reaction may be carried out either in the absence or presence of an inert solvent at a temperature ranging from about room temperature to about 200° C. In the reaction above, examples of the base are an alkali metal alkoxide such as potassium t-butoxide, sodium methoxide, sodium ethoxide and the like; an alkali metal hydride such as sodium hydride and the like; an organic base such as triethylamine, pyridine, 4-dimethylaminopyridine, N-methylmorpholine and the like; an inorganic salt such as potassium carbonate, sodium carbonate, sodium hydrogen carbonate and the like; and the like.

Examples of the inert solvent are an alcohol such as methanol, ethanol, t-butanol and the like; an aprotonic solvent such as pyridine, N,N-dimethylformamide dimethylsulfoxide, hexamethylphosphorictriamide, acetonitrile and the like; a halogenated hydrocarbon such as dichloromethane, chloroform, 1,2-dichloroethane and the like; a hydrocarbon such as benzene, toluene, hexane and the like; and an ether such as tetrahydrofuran, dioxane, diethyl ether and the like; and the like.

The starting compound represented by the formula (3) may be prepared by reacting a ketone derivatives represented by the formula (4) with an acid chloride or an ester represented formula (5):

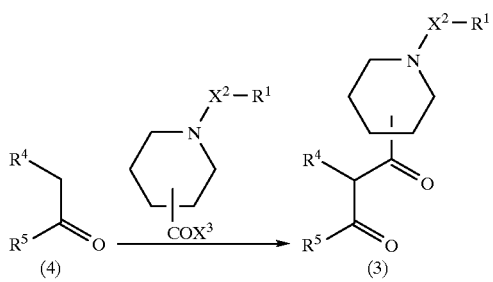

wherein $X^2$, $R^1$, $R^4$ and $R^5$ have the same meaning as defined in the formula (2) and $X^3$ is chlorine atom or an alkoxy.

The reaction may be carried out in the presence of a base in an inert solvent at a temperature ranging from about −78° C. to about reflux temperature. Examples of the base are an alkali metal alkoxide such as potassium t-butoxide, sodium methoxide sodium ethoxide and the like; a lithium compound such as n-butyl lithium, lithium N,N-diisopropylamide and the like; a metal hydride such as sodium hydride and the like; and the like.

Examples of the solvents are an alcohol such as methanol, ethanol, t-butanol and the like; an ether such as diethyl ether, tetrahydrofuran and the like; and the like.

The starting compounds (5) may be prepared from isonipecotic acid, nipecotic acid, pipecolinic acid or a derivative thereof by a conventional method known to a skilled person in the art of organic chemistry.

A 1,3-diketone compound may also be prepared by the following processes.

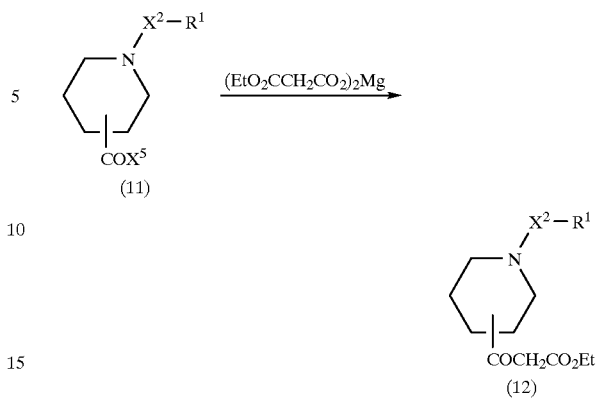

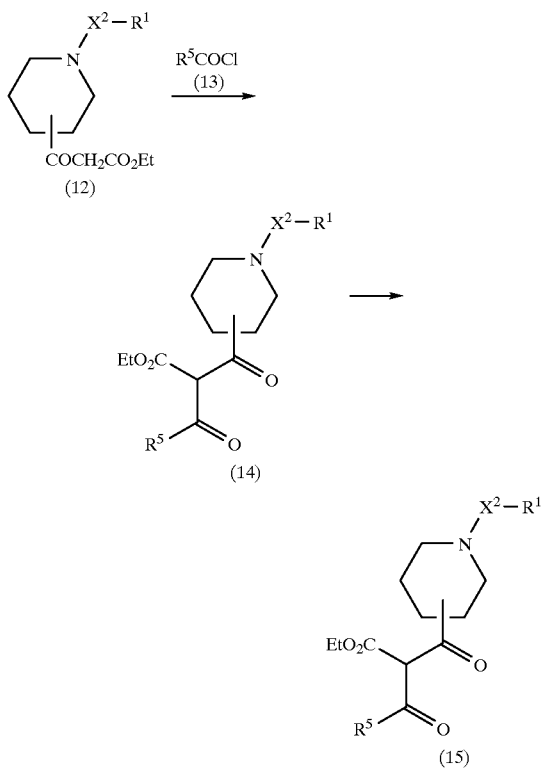

Wherein $X^2$ and $R^5$ are as defined in the formula (2).

The compound of the formula (14) may be prepared by treating a β-ketoester of the formula (12) with an acid chloride of the formula (13). The reaction is carried out in the presence of a suitable base such as an alkaline metal hydride (e.g. sodium hydride, etc.), or an alkaline earth metal alkoxide (e.g. magnesium ethoxide, etc.) in an inert solvent such as an aprotonic solvent (e.g. N,N-dimethylformamide, dimethylsulfoxide, etc.), an ether (e.g. tetrahydrofuran, diethylether, etc.) or a hydrocarbon (e.g. benzene, toluene, hexane, etc.), at a temperature ranging from about 0° C. to about reflux temperature of the solvent.

The acid chloride (13) may be prepared by treating the corresponding acid with a chlorinating agent using the reactions and techniques well known to a skilled person in the art of organic chemistry. Selected examples of the chlorinating agent include but are not limited to oxalyl chloride, thionyl chloride, phosphorous oxychloride, phosphorous trichloride, and phosphorous pentachloride. The reaction may be carried out either in the absence of a solvent or in an inert solvent such as a halogenated hydrocarbon (e.g. dichloromethane, dichloroethane, etc.), an ether (e.g. diethylether, tetrahydrofuran, etc.), or hydrocarbon (e.g. benzene, toluene, hexane, etc.), at a temperature ranging from about 0° C. to about reflux temperature of the solvent either in the absence or presence of base. Selected examples of the base include but are not limited to pyridine, 4-dimethylaminopyridine, triethylamine and imidazole.

The compound of the formula (15) may be prepared by deesterizing the compound of formula (14). The deesterizing reaction may be carried out in a solvent such as an aprotonic solvent (e.g. N,N-dimethylformamide, dimethylsulfoxide, etc.), or an acidic solvent (e.g. acetic acid, etc.) either in the presence or absence of water at a temperature ranging from about room temperature to about reflux temperature.

(Wherein $X^2$ and $R^1$ have the same meaning described in the formula (2). $X^5$ is a chlorine atom, imidazole or a alkoxycarbonyloxy.)

The β-ketoester of the formula (12) may be prepared by treating an acid derivative of the formula (11) with magnesium monoethylmalonate. The reaction is carried out in an inert solvent such as an aprotonic solvent (e.g. N,N-dimethylformamide, dimethylsulfoxide, etc.), an ether (e.g. tetrahydrofuran, diethylether, etc.), or a hydrocarbon (e.g. benzene, toluene, hexane, etc.), at a temperature ranging from about 0° C. to about reflux temperature of the solvent.

Process (B)

With respect to a compound within the formula (1) wherein $R^2$ and $R^3$ are combined with pyrimidine to form a pyridopyrimidine or a quinazoline, the process may be explained by using an example compound of formula (6) having the quinazoline structure.

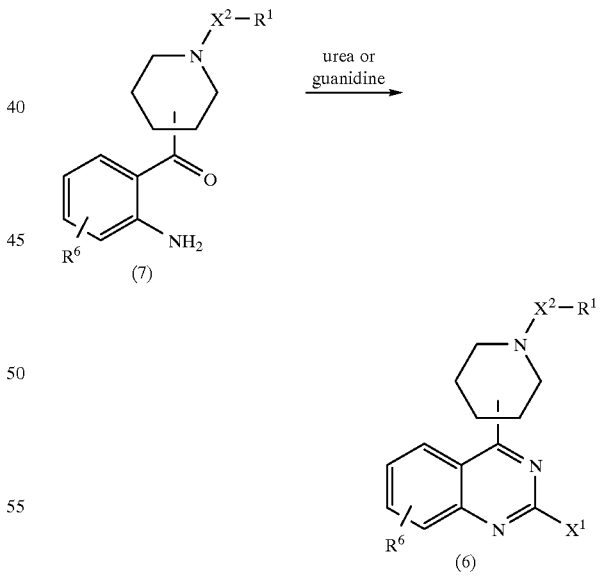

wherein: $X^1$, $X^2$ and $R^1$ have the same significance as defined in the formula (1-d);

$R^6$ represents a substituent at the 5, 6, 7 or 8 position of the quinazoline ring. The compound (6) may have one $R^6$ or up to 4 $R^6$'s. If the compound (6) has more than one $R^6$'s, each $R^6$'s may be the same or different. $R^6$ is a halogen, an alkyl, an alkoxy, nitro, cyano, carboxyl, hydroxy, amino, trifluoromethyl, an alkylamino, a dialkylamino, an alkanoyl, an alkanoylamino, sulfamoyl, an alkylaminosulfonyl, a dialkylamino or an alkoxycarbonyl.

A compound of the formula (6) may be prepared by treating an aminoketone compound represented by the formula (7) with a reagent such as urea, sodium cyanate, potassium cyanate, guanidine or cyanamide. The reaction may be carried out either in the absence or presence of an inert solvent, either in the presence or absence of a base, at a temperature ranging from about room temperature to about 200° C.

In the reaction described above, examples of the base are an alkali metal alkoxide such as potassium t-butoxide, sodium methoxide, sodium ethoxide and the like; a metal hydride such as sodium hydride and the like; an organic amine such as triethylamine, pyridine, 4-dimethylaminopyridine, N-methylmorpholine and the like; an inorganic salt such as potassium carbonate, sodium carbonate, sodium hydrogencarbonate and the like; and the like.

Examples of the solvent are an alcohol such as methanol, ethanol, t-butanol and the like; an aprotonic polar solvent such as pyridine, N,N-dimethylformamide, dimethylsulfoxide, hexamethylphosphorictriamide, acetonitrile and the like; a halogenated hydrocarbon such as dichloromethane, chloroform, 1,2-dichloroethane and the like; a hydrocarbon such as benzene, toluene, hexane and the like; an ether such as tetrahydrofuran, dioxane, diethyl ether and the like; and the like.

The starting compound (7) may be prepared by treating an aniline derivative of the formula (8) with a nitrile or an acid chloride of the formula (9).

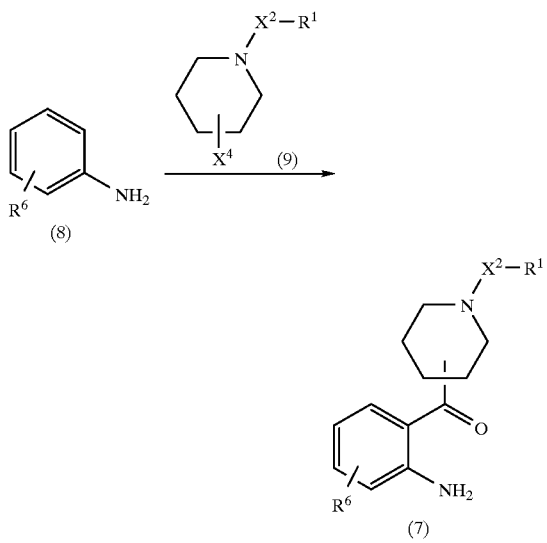

wherein $X^2$, $R^1$ and $R^6$ have the same meaning as defined in the formula (1-d) and $X^4$ is cyano or —COCl. The reaction may be carried out in an inert solvent in the presence of a Lewis acid at a temperature ranging from about room temperature to about reflux temperature.

Examples of the Lewis acid are aluminum chloride, tin tetrachloride, titanium tetrachloride, zinc dichloride, boron trichloride and the like. Two or more Lewis acids in combination may be applied to accelerate the reaction Examples of the solvent are a halogenated hydrocarbon such as dichloromethane, chloroform, 1,2-dichloroethane and the like; a hydrocarbon such as benzene, toluene, hexane and the like; an ether such as tetrahydrofuran, dioxane, diethyl ether and the like; carbon disulfide; and the like.

The starting compound (9) may be prepared from isonipecotinic acid, nipecotic acid, pipecolinic acid or a derivative thereof by a method well known to a skilled person in the art of organic chemistry.

Process (C)

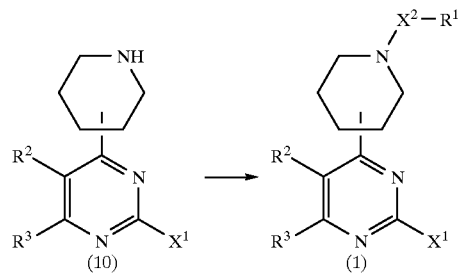

wherein $X^1$, $X^2$, $R^1$, $R^2$ and $R^3$ have the same meaning as defined in the formula (1).

The piperidinylpyrimidine derivative of the formula (1) may be prepared by introducing the corresponding substituent into a piperidine compound of the formula (10).

A compound of formula (1), wherein $X^2$ is —(CO)—, may be prepared by treating a compound of the formula (10) with a corresponding acid anhydride or acid chloride. The reaction may be carried out in an inert solvent in the presence of a condensing reagent at a temperature ranging from about 0° C. to about reflux temperature.

A compound of formula (1), wherein $X^2$ is —(CO)—, may also be prepared by treating a compound of the formula (10) with a corresponding acid. The reaction may be carried out in an inert solvent in the presence of a condensing reagent at a temperature ranging from about 0° C. to about reflux temperature.

A compound of formula (1), wherein $X^2$ is —(CO)O—, may be prepared by treating a compound of the formula (10) with a corresponding chloroformate. The reaction may be carried out in an inert solvent in the presence of a base at a temperature ranging from about 0° C. to about reflux temperature.

A compound of formula (1), wherein $X^2$ is —(CO)NH—, may be prepared by treating a compound of the formula (10) with a corresponding isocyanate. The reaction may be carried out in an inert solvent at a temperature ranging from about 0° C. to about reflux temperature.

A compound of formula (1), wherein $X^2$ is —(SO$_2$)—, may be prepared by treating a compound of the formula (10) with a corresponding sulfonic acid chloride. The reaction may be carried out in an inert solvent in the presence of a base at a temperature ranging from about 0° C. to about reflux temperature.

In the reaction described above, examples of the base are an organic amine such as triethylamine, pyridine, 4-dimethylaminopyridine, N-methylmorpholine and the like; an inorganic salt such as potassium carbonate, sodium carbonate, sodium hydrogen carbonate and the like; and the like.

Examples of the solvent are an aprotonic polar solvent such as N,N-dimethylformamide, dimethylsulfoxide, hexamethylphosphorictriamide, acetonitrile and the like; a hydrocarbon such as benzene, toluene, hexane and the like; a halogenated hydrocarbon such as dichloromethane, chloroform, 1,2-dichloroethane and the like; an ether such as tetrahydrofuran, dioxane, diethyl ether and the like; and the like.

Examples of the condensing reagent are N,N'-dicyclohexylcarbodiimide, 1-ethyl-3-(3-dimethylaminopropyl)carbodiimide and the like.

The compound of formula (10) may be prepared by hydrolyzing a compound of formula (11):

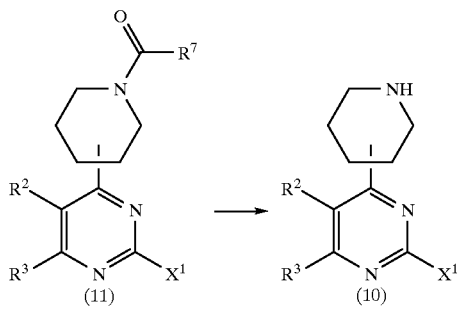

wherein $X^1$, $R^2$ and $R^3$ have the same meaning as defined in the formula (1) and $R^7$ is an alkyl or an aryl.

The hydrolysis above may be carried out in a solvent mixture of an aqueous solution of potassium hydroxide or sodium hydroxide and an alcohol such as ethanol, ethylene glycol or methoxyethanol, or an ether such as 1,4-dioxane or tetrahydrofuran, at a temperature ranging from about room temperature to about the reflux temperature.

In the reactions described above, where the substituent $R^1$, $R^2$, $R^3$, $R^4$ or $R^5$ may contain a residue such as amino, an alkyl amino or hydroxy, the residue may be protected prior to the reaction and the protective group is then deprotected to prepare the desired compound. A man skilled in the art of organic chemistry may choose an appropriate protective group from groups described below depending on the nature or condition of reactions or processes. Examples of the protective group available are an alkanoyl such as acetyl, benzoyl and the like for protecting the amino and alkylamino groups, an alkanoyl such as acetyl, benzoyl and the like, allyl, benzyl, methyl, methoxymethyl, trimethylsilyl and the like for protecting the hydroxy group. The details of the protective groups and procedures are described in T. W. Greene, "Protective Groups in Organic Synthesis", John Wiley & Sons Inc. (1981).

Following are typical compounds of the invention, wherein the symbol "Ph" is phenyl and "Boc" is t-butoxycarbonyl.

TABLE 1

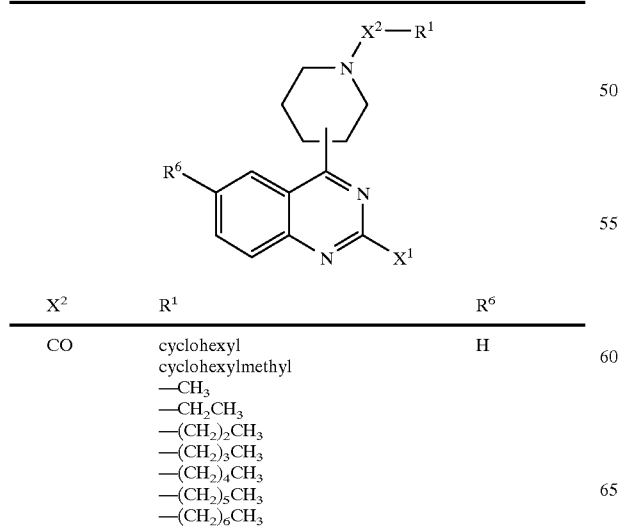

| $X^2$ | $R^1$ | $R^6$ |
|---|---|---|
| CO | cyclohexyl | H |
|  | cyclohexylmethyl |  |
|  | —$CH_3$ |  |
|  | —$CH_2CH_3$ |  |
|  | —$(CH_2)_2CH_3$ |  |
|  | —$(CH_2)_3CH_3$ |  |
|  | —$(CH_2)_4CH_3$ |  |
|  | —$(CH_2)_5CH_3$ |  |
|  | —$(CH_2)_6CH_3$ |  |

TABLE 1-continued

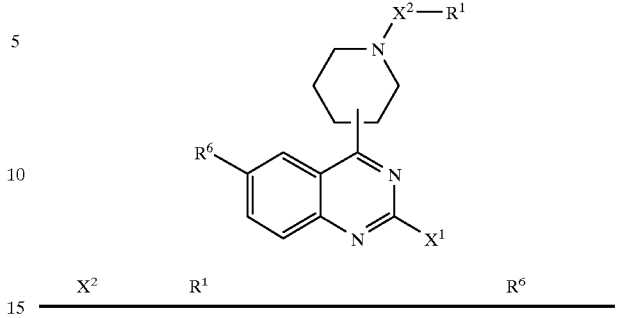

| $X^2$ | $R^1$ | $R^6$ |
|---|---|---|
|  | —$(CH_2)_7CH_3$ |  |
|  | —$(CH_2)_8CH_3$ |  |
|  | —$(CH_2)_9CH_3$ |  |
|  | —$(CH_2)_5OH$ |  |
|  | —$(CH_2)_6OH$ |  |
|  | —$(CH_2)_7OH$ |  |
|  | —$(CH_2)_8OH$ |  |
|  | —$(CH_2)_9OH$ |  |
|  | phenyl |  |
|  | 2-methoxyphenyl |  |
|  | 3-methoxyphenyl |  |
|  | 4-methoxyphenyl |  |
|  | 2-chlorophenyl |  |
|  | 3-chlorophenyl |  |
|  | 4-chlorophenyl |  |
|  | 2-fluorophenyl |  |
|  | 3-fluorophenyl |  |
|  | 4-fluorophenyl |  |
|  | 2-methylphenyl |  |
|  | 3-methylphenyl |  |
|  | 4-methylphenyl |  |
|  | 2-furyl |  |
|  | 3-furyl |  |
|  | 2-pyridyl |  |
|  | 3-pyridyl |  |
|  | 4-pyridyl |  |
|  | 2,3-dimethoxyphenyl |  |
|  | 2,4-dimethoxyphenyl |  |
|  | 2,5-dimethoxyphenyl |  |
|  | 2,6-dimethoxyphenyl |  |
|  | 3,4-dimethoxyphenyl |  |
|  | 3,5-dimethoxyphenyl |  |
|  | 2,3-dichlorophenyl |  |
|  | 2,4-dichlorophenyl |  |
|  | 2,5-dichlorophenyl |  |
|  | 2,6-dichlorophenyl |  |
|  | 3,4-dichlorophenyl |  |
|  | 2,4-dinitrophenyl |  |
|  | 3,4-methylenedioxyphenyl |  |
|  | 2,3-methylenedioxyphenyl |  |
|  | 1-naphthyl |  |
|  | 2-naphthyl |  |
|  | 2,3,4-trimethoxyphenyl |  |
|  | 2,3,6-trimethoxyphenyl |  |
|  | 2,4,5-trimethoxyphenyl |  |
|  | 2,4,6-trimethoxyphenyl |  |
|  | 3,4,5-trimethoxyphenyl |  |
|  | 2,3,5-trichlorophenyl |  |
|  | 2,4,6-trichlorophenyl |  |
|  | benzyl |  |
|  | 2-methoxybenzyl |  |
|  | 3-methoxybenzyl |  |
|  | 4-methoxybenzyl |  |
|  | 2-chlorobenzyl |  |
|  | 3-chlorobenzyl |  |
|  | 4-chlorobenzyl |  |
|  | 2-fluorobenzyl |  |
|  | 3-fluorobenzyl |  |
|  | 4-fluorobenzyl |  |
|  | 2-methylbenzyl |  |
|  | 3-methylbenzyl |  |
|  | 4-methylbenzyl |  |
|  | 2-pyridylmethyl |  |

TABLE 1-continued

| X² | R¹ | R⁶ |
|---|---|---|
| | 3-pyridylmethyl | |
| | 2,5-dimethoxybenzyl | |
| | 3,4-dimethoxybenzyl | |
| | 3,5-dimethoxybenzyl | |
| | 2,4-dichlorobenzyl | |
| | 2,6-dichlorobenzyl | |
| | 3,4-dichlorobenzyl | |
| | 2,4-dinitrobenzyl | |
| | 3,4-methylenedioxybenzyl | |
| | 2,3-methylenedioxybenzyl | |
| | 3,4,5-trimethoxybenzyl | |
| | 2-phenylethyl | |
| | 2-(2-methoxyphenyl)ethyl | |
| | 2-(3-methoxyphenyl)ethyl | |
| | 2-(4-methoxyphenyl)ethyl | |
| | 2-(2,3-dimethoxyphenyl)ethyl | |
| | 2-(3,4-dimethoxyphenyl)ethyl | |
| | 2-(2,3,4-trimethoxyphenyl)ethyl | |
| | 2-(3,4,5-trimethoxyphenyl)ethyl | |
| | 2-(2-chlorophenyl)ethyl | |
| | 2-(4-chlorophenyl)ethyl | |
| | 2-(3,4-dichlorophenyl)ethyl | |
| | 2-(3,4-methylenedioxyphenyl)ethyl | |
| | 3-phenylpropyl | |
| | 3-(4-methoxyphenyl)propyl | |
| | 3-(3,4-dimethoxyphenyl)propyl | |
| | 3-(3,4-methylenedioxyphenyl)propyl | |
| (CO)O | Ph | |
| | —CH₂Ph | |
| (CO)NH | —(CH₂)₇CH₃ | |
| | -Ph | |
| | —CH₂Ph | |
| SO₂ | —(CH₂)₇CH₃ | H |
| | -Ph | |
| | —CH₂Ph | |
| CO | cyclohexyl | OCH₃ |
| | cyclohexylmethyl | |
| | —CH₃ | |
| | —CH₂CH₃ | |
| | —(CH₂)₂CH₃ | |
| | —(CH₂)₃CH₃ | |
| | —(CH₂)₄CH₃ | |
| | —(CH₂)₅CH₃ | |
| | —(CH₂)₆CH₃ | |
| | —(CH₂)₇CH₃ | |
| | —(CH₂)₈CH₃ | |
| | —(CH₂)₉CH₃ | |
| | —(CH₂)₅OH | |
| | —(CH₂)₆OH | |
| | —(CH₂)₇OH | |
| | —(CH₂)₈OH | |
| | —(CH₂)₉OH | |
| | phenyl | |
| | 2-methoxyphenyl | |
| | 3-methoxyphenyl | |
| | 4-methoxyphenyl | |
| | 2-chlorophenyl | |
| | 3-chlorophenyl | |
| | 4-chlorophenyl | |
| | 2-fluorophenyl | |
| | 3-fluorophenyl | |
| | 4-fluorophenyl | |
| | 2-methylphenyl | |
| | 3-methylphenyl | |
| | 4-methylphenyl | |
| | 2-furyl | |
| | 3-furyl | |
| | 2-pyridyl | |
| | 3-pyridyl | |
| | 4-pyridyl | |
| | 2,3-dimethoxyphenyl | |
| | 2,4-dimethoxyphenyl | |
| | 2,5-dimethoxyphenyl | |
| | 2,6-dimethoxyphenyl | |
| | 3,4-dimethoxyphenyl | |
| | 3,5-dimethoxyphenyl | |
| | 2,3-dichlorophenyl | |
| | 2,4-dichlorophenyl | |
| | 2,5-dichlorophenyl | |
| | 2,6-dichlorophenyl | |
| | 3,4-dichlorophenyl | |
| | 2,4-dinitrophenyl | |
| | 3,4-methylenedioxyphenyl | |
| | 2,3-methylenedioxyphenyl | |
| | 1-naphthyl | |
| | 2-naphthyl | |
| | 2,3,4-trimethoxyphenyl | |
| | 2,3,6-trimethoxyphenyl | |
| | 2,4,5-trimethoxyphenyl | |
| | 2,4,6-trimethoxyphenyl | |
| | 3,4,5-trimethoxyphenyl | |
| | 2,3,5-trichlorophenyl | |
| | 2,4,6-trichlorophenyl | |
| | benzyl | |
| | 2-methoxybenzyl | |
| | 3-methoxybenzyl | |
| | 4-methoxybenzyl | |
| | 2-chlorobenzyl | |
| | 3-chlorobenzyl | |
| | 4-chlorobenzyl | |
| | 2-fluorobenzyl | |
| | 3-fluorobenzyl | |
| | 4-fluorobenzyl | |
| | 2-methylbenzyl | |
| | 3-methylbenzyl | |
| | 4-methylbenzyl | |
| | 2-pyridylmethyl | |
| | 3-pyridylmethyl | |
| | 2,5-dimethoxybenzyl | |
| | 3,4-dimethoxybenzyl | |
| | 3,5-dimethoxybenzyl | |
| | 2,4-dichlorobenzyl | |
| | 2,6-dichlorobenzyl | |
| | 3,4-dichlorobenzyl | |
| | 2,4-dinitrobenzyl | |
| | 3,4-methylenedioxybenzyl | |
| | 2,3-methylenedioxybenzyl | |
| | 3,4,5-trimethoxybenzyl | |
| | 2-phenylethyl | |
| | 2-(2-methoxyphenyl)ethyl | |
| | 2-(3-methoxyphenyl)ethyl | |
| | 2-(4-methoxyphenyl)ethyl | |
| | 2-(2,3-dimethoxyphenyl)ethyl | |
| | 2-(3,4-dimethoxyphenyl)ethyl | |
| | 2-(2,3,4-trimethoxyphenyl)ethyl | |
| | 2-(3,4,5-trimethoxyphenyl)ethyl | |

TABLE 1-continued

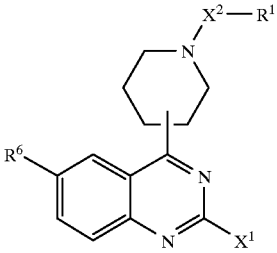

| X² | R¹ | R⁶ |
|---|---|---|
| | 2-(2-chlorophenyl)ethyl | |
| | 2-(4-chlorophenyl)ethyl | |
| | 2-(3,4-dichlorophenyl)ethyl | |
| | 2-(3,4-methylenedioxyphenyl)ethyl | |
| | 3-phenylpropyl | |
| | 3-(4-methoxyphenyl)propyl | |
| | 3-(3,4-dimethoxyphenyl)propyl | |
| | 3-(3,4-methylenedioxyphenyl)propyl | |
| (CO)O | Ph | |
| | —CH₂Ph | |
| (CO)NH | —(CH₂)₇CH₃ | |
| | -Ph | |
| | —CH₂Ph | |
| SO₂ | —(CH₂)₇CH₃ | OCH₃ |
| | -Ph | |
| | —CH₂Ph | |
| CO | cyclohexyl | Cl |
| | cyclohexylmethyl | |
| | —CH₃ | |
| | —CH₂CH₃ | |
| | —(CH₂)₂CH₃ | |
| | —(CH₂)₃CH₃ | |
| | —(CH₂)₄CH₃ | |
| | —(CH₂)₅CH₃ | |
| | —(CH₂)₆CH₃ | |
| | —(CH₂)₇CH₃ | |
| | —(CH₂)₈CH₃ | |
| | —(CH₂)₉CH₃ | |
| | —(CH₂)₅OH | |
| | —(CH₂)₆OH | |
| | —(CH₂)₇OH | |
| | —(CH₂)₈OH | |
| | —(CH₂)₉OH | |
| | phenyl | |
| | 2-methoxyphenyl | |
| | 3-methoxyphenyl | |
| | 4-methoxyphenyl | |
| | 2-chlorophenyl | |
| | 3-chlorophenyl | |
| | 4-chlorophenyl | |
| | 2-fluorophenyl | |
| | 3-fluorophenyl | |
| | 4-fluorophenyl | |
| | 2-methylphenyl | |
| | 3-methylphenyl | |
| | 4-methylphenyl | |
| | 2-furyl | |
| | 3-furyl | |
| | 2-pyridyl | |
| | 3-pyridyl | |
| | 4-pyridyl | |
| | 2,3-dimethoxyphenyl | |
| | 2,4-dimethoxyphenyl | |
| | 2,5-dimethoxyphenyl | |
| | 2,6-dimethoxyphenyl | |
| | 3,4-dimethoxyphenyl | |
| | 3,5-dimethoxyphenyl | |
| | 2,3-dichlorophenyl | |
| | 2,4-dichlorophenyl | |
| | 2,5-dichlorophenyl | |
| | 2,6-dichlorophenyl | |
| | 3,4-dichlorophenyl | |
| | 2,4-dinitrophenyl | |

TABLE 1-continued

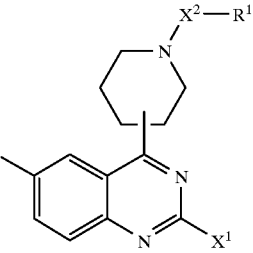

| X² | R¹ | R⁶ |
|---|---|---|
| | 3,4-methylenedioxyphenyl | |
| | 2,3-methylenedioxyphenyl | |
| | 1-naphthyl | |
| | 2-naphthyl | |
| | 2,3,4-trimethoxyphenyl | |
| | 2,3,6-trimethoxyphenyl | |
| | 2,4,5-trimethoxyphenyl | |
| | 2,4,6-trimethoxyphenyl | |
| | 3,4,5-trimethoxyphenyl | |
| | 2,3,5-trichlorophenyl | |
| | 2,4,6-trichlorophenyl | |
| | benzyl | |
| | 2-methoxybenzyl | |
| | 3-methoxybenzyl | |
| | 4-methoxybenzyl | |
| | 2-chlorobenzyl | |
| | 3-chlorobenzyl | |
| | 4-chlorobenzyl | |
| | 2-fluorobenzyl | |
| | 3-fluorobenzyl | |
| | 4-fluorobenzyl | |
| | 2-methylbenzyl | |
| | 3-methylbenzyl | |
| | 4-methylbenzyl | |
| | 2-pyridylmethyl | |
| | 3-pyridylmethyl | |
| | 2,5-dimethoxybenzyl | |
| | 3,4-dimethoxybenzyl | |
| | 3,5-dimethoxybenzyl | |
| | 2,4-dichlorobenzyl | |
| | 2,6-dichlorobenzyl | |
| | 3,4-dichlorobenzyl | |
| | 2,4-dinitrobenzyl | |
| | 3,4-methylenedioxybenzyl | |
| | 2,3-methylenedioxybenzyl | |
| | 3,4,5-trimethoxybenzyl | |
| | 2-phenylethyl | |
| | 2-(2-methoxyphenyl)ethyl | |
| | 2-(3-methoxyphenyl)ethyl | |
| | 2-(4-methoxyphenyl)ethyl | |
| | 2-(2,3-dimethoxyphenyl)ethyl | |
| | 2-(3,4-dimethoxyphenyl)ethyl | |
| | 2-(2,3,4-trimethoxyphenyl)ethyl | |
| | 2-(3,4,5-trimethoxyphenyl)ethyl | |
| | 2-(2-chlorophenyl)ethyl | |
| | 2-(4-chlorophenyl)ethyl | |
| | 2-(3,4-dichlorophenyl)ethyl | |
| | 2-(3,4-methylenedioxyphenyl)ethyl | |
| | 3-phenylpropyl | |
| | 3-(4-methoxyphenyl)propyl | |
| | 3-(3,4-dimethoxyphenyl)propyl | |
| | 3-(3,4-methylenedioxyphenyl)propyl | |
| (CO)O | Ph | |
| | —CH₂Ph | |
| (CO)NH | —(CH₂)₇CH₃ | |
| | -Ph | |
| | —CH₂Ph | |
| SO₂ | —(CH₂)₇CH₃ | Cl |
| | -Ph | |
| | —CH₂Ph | |

TABLE 2

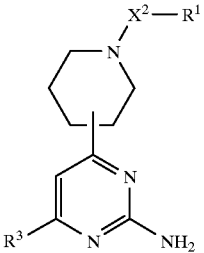

| X² | R¹ | R³ |
|---|---|---|
| CO | cyclohexyl | Ph |
| | cyclohexylmethyl | |
| | —CH₃ | |
| | —CH₂CH₃ | |
| | —(CH₂)₂CH₃ | |
| | —(CH₂)₃CH₃ | |
| | —(CH₂)₄CH₃ | |
| | —(CH₂)₅CH₃ | |
| | —(CH₂)₆CH₃ | |
| | —(CH₂)₇CH₃ | |
| | —(CH₂)₈CH₃ | |
| | —(CH₂)₉CH₃ | |
| | —(CH₂)₅OH | |
| | —(CH₂)₆OH | |
| | —(CH₂)₇OH | |
| | —(CH₂)₈OH | |
| | —(CH₂)₉OH | |
| | phenyl | |
| | 2-methoxyphenyl | |
| | 3-methoxyphenyl | |
| | 4-methoxyphenyl | |
| | 2-chlorophenyl | |
| | 3-chlorophenyl | |
| | 4-chlorophenyl | |
| | 2-fluorophenyl | |
| | 3-fluorophenyl | |
| | 4-fluorophenyl | |
| | 2-methylphenyl | |
| | 3-methylphenyl | |
| | 4-methylphenyl | |
| | 2-furyl | |
| | 3-furyl | |
| | 2-pyridyl | |
| | 3-pyridyl | |
| | 4-pyridyl | |
| | 2,3-dimethoxyphenyl | |
| | 2,4-dimethoxyphenyl | |
| | 2,5-dimethoxyphenyl | |
| | 2,6-dimethoxyphenyl | |
| | 3,4-dimethoxyphenyl | |
| | 3,5-dimethoxyphenyl | |
| | 2,3-dichlorophenyl | |
| | 2,4-dichlorophenyl | |
| | 2,5-dichlorophenyl | |
| | 2,6-dichlorophenyl | |
| | 3,4-dichlorophenyl | |
| | 2,4-dinitrophenyl | |
| | 3,4-methylenedioxyphenyl | |
| | 2,3-methylenedioxyphenyl | |
| | 1-naphthyl | |
| | 2-naphthyl | |
| | 2,3,4-trimethoxyphenyl | |
| | 2,3,6-trimethoxyphenyl | |
| | 2,4,5-trimethoxyphenyl | |
| | 2,4,6-trimethoxyphenyl | |
| | 3,4,5-trimethoxyphenyl | |
| | 2,3,5-trichlorophenyl | |
| | 2,4,6-trichlorophenyl | |
| | benzyl | |
| | 2-methoxybenzyl | |
| | 3-methoxybenzyl | |
| | 4-methoxybenzyl | |
| | 2-chlorobenzyl | |
| | 3-chlorobenzyl | |

TABLE 2-continued

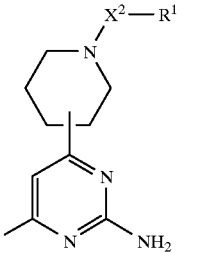

| X² | R¹ | R³ |
|---|---|---|
| | 4-chlorobenzyl | |
| | 2-fluorobenzyl | |
| | 3-fluorobenzyl | |
| | 4-fluorobenzyl | |
| | 2-methylbenzyl | |
| | 3-methylbenzyl | |
| | 4-methylbenzyl | |
| | 2-pyridylmethyl | |
| | 3-pyridylmethyl | |
| | 2,5-dimethoxybenzyl | |
| | 3,4-dimethoxybenzyl | |
| | 3,5-dimethoxybenzyl | |
| | 2,4-dichlorobenzyl | |
| | 2,6-dichlorobenzyl | |
| | 3,4-dichlorobenzyl | |
| | 2,4-dinitrobenzyl | |
| | 3,4-methylenedioxybenzyl | |
| | 2,3-methylenedioxybenzyl | |
| | 3,4,5-trimethoxybenzyl | |
| | 2-phenylethyl | |
| | 2-(2-methoxyphenyl)ethyl | |
| | 2-(3-methoxyphenyl)ethyl | |
| | 2-(4-methoxyphenyl)ethyl | |
| | 2-(2,3-dimethoxyphenyl)ethyl | |
| | 2-(3,4-dimethoxyphenyl)ethyl | |
| | 2-(2,3,4-trimethoxyphenyl)ethyl | |
| | 2-(3,4,5-trimethoxyphenyl)ethyl | |
| | 2-(2-chlorophenyl)ethyl | |
| | 2-(4-chlorophenyl)ethyl | |
| | 2-(3,4-dichlorophenyl)ethyl | |
| | 2-(3,4-methylenedioxyphenyl)ethyl | |
| | 3-phenylpropyl | |
| | 3-(4-methoxyphenyl)propyl | |
| | 3-(3,4-dimethoxyphenyl)propyl | |
| | 3-(3,4-methylenedioxyphenyl)propyl | |
| (CO)O | Ph | |
| | —CH₂Ph | |
| (CO)NH | —(CH₂)₇CH₃ | |
| | -Ph | |
| | —CH₂Ph | |
| SO₂ | —(CH₂)₇CH₃ | Ph |
| | -Ph | |
| | —CH₂Ph | |
| CO | cyclohexyl | 4-chloro-phenyl |
| | cyclohexylmethyl | |
| | —CH₃ | |
| | —CH₂CH₃ | |
| | —(CH₂)₂CH₃ | |
| | —(CH₂)₃CH₃ | |
| | —(CH₂)₄CH₃ | |
| | —(CH₂)₅CH₃ | |
| | —(CH₂)₆CH₃ | |
| | —(CH₂)₇CH₃ | |
| | —(CH₂)₈CH₃ | |
| | —(CH₂)₉CH₃ | |
| | —(CH₂)₅OH | |
| | —(CH₂)₆OH | |
| | —(CH₂)₇OH | |
| | —(CH₂)₈OH | |
| | —(CH₂)₉OH | |
| | phenyl | |
| | 2-methoxyphenyl | |
| | 3-methoxyphenyl | |
| | 4-methoxyphenyl | |

TABLE 2-continued

[Structure: 4-(piperidin-4-yl)pyrimidin-2-amine with N-X²-R¹ on piperidine nitrogen and R³ at pyrimidine 6-position]

| X² | R¹ | R³ |
|---|---|---|
|  | 2-chlorophenyl |  |
|  | 3-chlorophenyl |  |
|  | 4-chlorophenyl |  |
|  | 2-fluorophenyl |  |
|  | 3-fluorophenyl |  |
|  | 4-fluorophenyl |  |
|  | 2-methylphenyl |  |
|  | 3-methylphenyl |  |
|  | 4-methylphenyl |  |
|  | 2-furyl |  |
|  | 3-furyl |  |
|  | 2-pyridyl |  |
|  | 3-pyridyl |  |
|  | 4-pyridyl |  |
|  | 2,3-dimethoxyphenyl |  |
|  | 2,4-dimethoxyphenyl |  |
|  | 2,5-dimethoxyphenyl |  |
|  | 2,6-dimethoxyphenyl |  |
|  | 3,4-dimethoxyphenyl |  |
|  | 3,5-dimethoxyphenyl |  |
|  | 2,3-dichlorophenyl |  |
|  | 2,4-dichlorophenyl |  |
|  | 2,5-dichlorophenyl |  |
|  | 2,6-dichlorophenyl |  |
|  | 3,4-dichlorophenyl |  |
|  | 2,4-dinitrophenyl |  |
|  | 3,4-methylenedioxyphenyl |  |
|  | 2,3-methylenedioxyphenyl |  |
|  | 1-naphthyl |  |
|  | 2-naphthyl |  |
|  | 2,3,4-trimethoxyphenyl |  |
|  | 2,3,6-trimethoxyphenyl |  |
|  | 2,4,5-trimethoxyphenyl |  |
|  | 2,4,6-trimethoxyphenyl |  |
|  | 3,4,5-trimethoxyphenyl |  |
|  | 2,3,5-trichlorophenyl |  |
|  | 2,4,6-trichlorophenyl |  |
|  | benzyl |  |
|  | 2-methoxybenzyl |  |
|  | 3-methoxybenzyl |  |
|  | 4-methoxybenzyl |  |
|  | 2-chlorobenzyl |  |
|  | 3-chlorobenzyl |  |
|  | 4-chlorobenzyl |  |
|  | 2-fluorobenzyl |  |
|  | 3-fluorobenzyl |  |
|  | 4-fluorobenzyl |  |
|  | 2-methylbenzyl |  |
|  | 3-methylbenzyl |  |
|  | 4-methylbenzyl |  |
|  | 2-pyridylmethyl |  |
|  | 3-pyridylmethyl |  |
|  | 2,5-dimethoxybenzyl |  |
|  | 3,4-dimethoxybenzyl |  |
|  | 3,5-dimethoxybenzyl |  |
|  | 2,4-dichlorobenzyl |  |
|  | 2,6-dichlorobenzyl |  |
|  | 3,4-dichlorobenzyl |  |
|  | 2,4-dinitrobenzyl |  |
|  | 3,4-methylenedioxybenzyl |  |
|  | 2,3-methylenedioxybenzyl |  |
|  | 3,4,5-trimethoxybenzyl |  |
|  | 2-phenylethyl |  |
|  | 2-(2-methoxyphenyl)ethyl |  |
|  | 2-(3-methoxyphenyl)ethyl |  |
|  | 2-(4-methoxyphenyl)ethyl |  |
|  | 2-(2,3-dimethoxyphenyl)ethyl |  |
|  | 2-(3,4-dimethoxyphenyl)ethyl |  |
|  | 2-(2,3,4-trimethoxyphenyl)ethyl |  |
|  | 2-(3,4,5-trimethoxyphenyl)ethyl |  |
|  | 2-(2-chlorophenyl)ethyl |  |
|  | 2-(4-chlorophenyl)ethyl |  |
|  | 2-(3,4-dichlorophenyl)ethyl |  |
|  | 2-(3,4-methylenedioxyphenyl)ethyl |  |
|  | 3-phenylpropyl |  |
|  | 3-(4-methoxyphenyl)propyl |  |
|  | 3-(3,4-dimethoxyphenyl)propyl |  |
|  | 3-(3,4-methylenedioxyphenyl)propyl |  |
| (CO)O | Ph |  |
|  | —CH₂Ph |  |
| (CO)NH | —(CH₂)₇CH₃ |  |
|  | -Ph |  |
|  | —CH₂Ph |  |
| SO₂ | —(CH₂)₇CH₃ | 4-chlorophenyl |
|  | -Ph |  |
|  | —CH₂Ph |  |
| CO | cyclohexyl | 4-methoxyphenyl |
|  | cyclohexylmethyl |  |
|  | —CH₃ |  |
|  | —CH₂CH₃ |  |
|  | —(CH₂)₂CH₃ |  |
|  | —(CH₂)₃CH₃ |  |
|  | —(CH₂)₄CH₃ |  |
|  | —(CH₂)₅CH₃ |  |
|  | —(CH₂)₆CH₃ |  |
|  | —(CH₂)₇CH₃ |  |
|  | —(CH₂)₈CH₃ |  |
|  | —(CH₂)₉CH₃ |  |
|  | —(CH₂)₅OH |  |
|  | —(CH₂)₆OH |  |
|  | —(CH₂)₇OH |  |
|  | —(CH₂)₈OH |  |
|  | —(CH₂)₉OH |  |
|  | phenyl |  |
|  | 2-methoxyphenyl |  |
|  | 3-methoxyphenyl |  |
|  | 4-methoxyphenyl |  |
|  | 2-chlorophenyl |  |
|  | 3-chlorophenyl |  |
|  | 4-chlorophenyl |  |
|  | 2-fluorophenyl |  |
|  | 3-fluorophenyl |  |
|  | 4-fluorophenyl |  |
|  | 2-methylphenyl |  |
|  | 3-methylphenyl |  |
|  | 4-methylphenyl |  |
|  | 2-furyl |  |
|  | 3-furyl |  |
|  | 2-pyridyl |  |
|  | 3-pyridyl |  |
|  | 4-pyridyl |  |
|  | 2,3-dimethoxyphenyl |  |
|  | 2,4-dimethoxyphenyl |  |
|  | 2,5-dimethoxyphenyl |  |
|  | 2,6-dimethoxyphenyl |  |
|  | 3,4-dimethoxyphenyl |  |
|  | 3,5-dimethoxyphenyl |  |
|  | 2,3-dichlorophenyl |  |

TABLE 2-continued

[Structure: piperidine N-X²-R¹ connected at 4-position to pyrimidine bearing R³ and NH₂]

| X² | R¹ | R³ |
|---|---|---|
| | 2,4-dichlorophenyl | |
| | 2,5-dichlorophenyl | |
| | 2,6-dichlorophenyl | |
| | 3,4-dichlorophenyl | |
| | 2,4-dinitrophenyl | |
| | 3,4-methylenedioxyphenyl | |
| | 2,3-methylenedioxyphenyl | |
| | 1-naphthyl | |
| | 2-naphthyl | |
| | 2,3,4-trimethoxyphenyl | |
| | 2,3,6-trimethoxyphenyl | |
| | 2,4,5-trimethoxyphenyl | |
| | 2,4,6-trimethoxyphenyl | |
| | 3,4,5-trimethoxyphenyl | |
| | 2,3,5-trichlorophenyl | |
| | 2,4,6-trichlorophenyl | |
| | benzyl | |
| | 2-methoxybenzyl | |
| | 3-methoxybenzyl | |
| | 4-methoxybenzyl | |
| | 2-chlorobenzyl | |
| | 3-chlorobenzyl | |
| | 4-chlorobenzyl | |
| | 2-fluorobenzyl | |
| | 3-fluorobenzyl | |
| | 4-fluorobenzyl | |
| | 2-methylbenzyl | |
| | 3-methylbenzyl | |
| | 4-methylbenzyl | |
| | 2-pyridylmethyl | |
| | 3-pyridylmethyl | |
| | 2,5-dimethoxybenzyl | |
| | 3,4-dimethoxybenzyl | |
| | 3,5-dimethoxybenzyl | |
| | 2,4-dichlorobenzyl | |
| | 2,6-dichlorobenzyl | |
| | 3,4-dichlorobenzyl | |
| | 2,4-dinitrobenzyl | |
| | 3,4-methylenedioxybenzyl | |
| | 2,3-methylenedioxybenzyl | |
| | 3,4,5-trimethoxybenzyl | |
| | 2-phenylethyl | |
| | 2-(2-methoxyphenyl)ethyl | |
| | 2-(3-methoxyphenyl)ethyl | |
| | 2-(4-methoxyphenyl)ethyl | |
| | 2-(2,3-dimethoxyphenyl)ethyl | |
| | 2-(3,4-dimethoxyphenyl)ethyl | |
| | 2-(2,3,4-trimethoxyphenyl)ethyl | |
| | 2-(3,4,5-trimethoxyphenyl)ethyl | |
| | 2-(2-chlorophenyl)ethyl | |
| | 2-(4-chlorophenyl)ethyl | |
| | 2-(3,4-dichlorophenyl)ethyl | |
| | 2-(3,4-methylenedioxyphenyl)ethyl | |
| | 3-phenylpropyl | |
| | 3-(4-methoxyphenyl)propyl | |
| | 3-(3,4-dimethoxyphenyl)propyl | |
| | 3-(3,4-methylenedioxyphenyl)propyl | |
| (CO)O | Ph | |
| | —CH₂Ph | |
| (CO)NH | —(CH₂)₇CH₃ | |
| | -Ph | |
| | —CH₂Ph | |
| SO₂ | —(CH₂)₇CH₃ | 4-methoxyphenyl |
| | -Ph | |
| | —CH₂Ph | |
| CO | cyclohexyl | 4-methoxybenzyl |
| | cyclohexylmethyl | |
| | —CH₃ | |
| | —CH₂CH₃ | |
| | —(CH₂)₂CH₃ | |
| | —(CH₂)₃CH₃ | |
| | —(CH₂)₄CH₃ | |
| | —(CH₂)₅CH₃ | |
| | —(CH₂)₆CH₃ | |
| | —(CH₂)₇CH₃ | |
| | —(CH₂)₈CH₃ | |
| | —(CH₂)₉CH₃ | |
| | —(CH₂)₅OH | |
| | —(CH₂)₆OH | |
| | —(CH₂)₇OH | |
| | —(CH₂)₈OH | |
| | —(CH₂)₉OH | |
| | phenyl | |
| | 2-methoxyphenyl | |
| | 3-methoxyphenyl | |
| | 4-methoxyphenyl | |
| | 2-chlorophenyl | |
| | 3-chlorophenyl | |
| | 4-chlorophenyl | |
| | 2-fluorophenyl | |
| | 3-fluorophenyl | |
| | 4-fluorophenyl | |
| | 2-methylphenyl | |
| | 3-methylphenyl | |
| | 4-methylphenyl | |
| | 2-furyl | |
| | 3-furyl | |
| | 2-pyridyl | |
| | 3-pyridyl | |
| | 4-pyridyl | |
| | 2,3-dimethoxyphenyl | |
| | 2,4-dimethoxyphenyl | |
| | 2,5-dimethoxyphenyl | |
| | 2,6-dimethoxyphenyl | |
| | 3,4-dimethoxyphenyl | |
| | 3,5-dimethoxyphenyl | |
| | 2,3-dichlorophenyl | |
| | 2,4-dichlorophenyl | |
| | 2,5-dichlorophenyl | |
| | 2,6-dichlorophenyl | |
| | 3,4-dichlorophenyl | |
| | 2,4-dinitrophenyl | |
| | 3,4-methylenedioxyphenyl | |
| | 2,3-methylenedioxyphenyl | |
| | 1-naphthyl | |
| | 2-naphthyl | |
| | 2,3,4-trimethoxyphenyl | |
| | 2,3,6-trimethoxyphenyl | |
| | 2,4,5-trimethoxyphenyl | |
| | 2,4,6-trimethoxyphenyl | |
| | 3,4,5-trimethoxyphenyl | |
| | 2,3,5-trichlorophenyl | |
| | 2,4,6-trichlorophenyl | |
| | benzyl | |
| | 2-methoxybenzyl | |
| | 3-methoxybenzyl | |
| | 4-methoxybenzyl | |
| | 2-chlorobenzyl | |

TABLE 2-continued

[Structure: 4-(piperidin-1-yl with N-X²-R¹)-6-R³-pyrimidin-2-amine]

| X² | R¹ | R³ |
|---|---|---|
| | 3-chlorobenzyl | |
| | 4-chlorobenzyl | |
| | 2-fluorobenzyl | |
| | 3-fluorobenzyl | |
| | 4-fluorobenzyl | |
| | 2-methylbenzyl | |
| | 3-methylbenzyl | |
| | 4-methylbenzyl | |
| | 2-pyridylmethyl | |
| | 3-pyridylmethyl | |
| | 2,5-dimethoxybenzyl | |
| | 3,4-dimethoxybenzyl | |
| | 3,5-dimethoxybenzyl | |
| | 2,4-dichlorobenzyl | |
| | 2,6-dichlorobenzyl | |
| | 3,4-dichlorobenzyl | |
| | 2,4-dinitrobenzyl | |
| | 3,4-methylenedioxybenzyl | |
| | 2,3-methylenedioxybenzyl | |
| | 3,4,5-trimethoxybenzyl | |
| | 2-phenylethyl | |
| | 2-(2-methoxyphenyl)ethyl | |
| | 2-(3-methoxyphenyl)ethyl | |
| | 2-(4-methoxyphenyl)ethyl | |
| | 2-(2,3-dimethoxyphenyl)ethyl | |
| | 2-(3,4-dimethoxyphenyl)ethyl | |
| | 2-(2,3,4-trimethoxyphenyl)ethyl | |
| | 2-(3,4,5-trimethoxyphenyl)ethyl | |
| | 2-(2-chlorophenyl)ethyl | |
| | 2-(4-chlorophenyl)ethyl | |
| | 2-(3,4-dichlorophenyl)ethyl | |
| | 2-(3,4-methylenedioxyphenyl)ethyl | |
| | 3-phenylpropyl | |
| | 3-(4-methoxyphenyl)propyl | |
| | 3-(3,4-dimethoxyphenyl)propyl | |
| | 3-(3,4-methylenedioxyphenyl)propyl | |
| (CO)O | Ph | |
| | —CH₂Ph | |
| (CO)NH | —(CH₂)₇CH₃ | |
| | -Ph | |
| | —CH₂Ph | |
| SO₂ | —(CH₂)₇CH₃ | 4-methoxybenzyl |
| | -Ph | |
| | —CH₂Ph | |
| CO | cyclohexyl | 4-chlorobenyl |
| | cyclohexylmethyl | |
| | —CH₃ | |
| | —CH₂CH₃ | |
| | —(CH₂)₂CH₃ | |
| | —(CH₂)₃CH₃ | |
| | —(CH₂)₄CH₃ | |
| | —(CH₂)₅CH₃ | |
| | —(CH₂)₆CH₃ | |
| | —(CH₂)₇CH₃ | |
| | —(CH₂)₈CH₃ | |
| | —(CH₂)₉CH₃ | |
| | —(CH₂)₅OH | |
| | —(CH₂)₆OH | |
| | —(CH₂)₇OH | |
| | —(CH₂)₈OH | |
| | —(CH₂)₉OH | |
| | phenyl | |
| | 2-methoxyphenyl | |
| | 3-methoxyphenyl | |
| | 4-methoxyphenyl | |
| | 2-chlorophenyl | |
| | 3-chlorophenyl | |
| | 4-chlorophenyl | |
| | 2-fluorophenyl | |
| | 3-fluorophenyl | |
| | 4-fluorophenyl | |
| | 2-methylphenyl | |
| | 3-methylphenyl | |
| | 4-methylphenyl | |
| | 2-furyl | |
| | 3-furyl | |
| | 2-pyridyl | |
| | 3-pyridyl | |
| | 4-pyridyl | |
| | 2,3-dimethoxyphenyl | |
| | 2,4-dimethoxyphenyl | |
| | 2,5-dimethoxyphenyl | |
| | 2,6-dimethoxyphenyl | |
| | 3,4-dimethoxyphenyl | |
| | 3,5-dimethoxyphenyl | |
| | 2,3-dichlorophenyl | |
| | 2,4-dichlorophenyl | |
| | 2,5-dichlorophenyl | |
| | 2,6-dichlorophenyl | |
| | 3,4-dichlorophenyl | |
| | 2,4-dinitrophenyl | |
| | 3,4-methylenedioxyphenyl | |
| | 2,3-methylenedioxyphenyl | |
| | 1-naphthyl | |
| | 2-naphthyl | |
| | 2,3,4-trimethoxyphenyl | |
| | 2,3,6-trimethoxyphenyl | |
| | 2,4,5-trimethoxyphenyl | |
| | 2,4,6-trimethoxyphenyl | |
| | 3,4,5-trimethoxyphenyl | |
| | 2,3,5-trichlorophenyl | |
| | 2,4,6-trichlorophenyl | |
| | benzyl | |
| | 2-methoxybenzyl | |
| | 3-methoxybenzyl | |
| | 4-methoxybenzyl | |
| | 2-chlorobenzyl | |
| | 3-chlorobenzyl | |
| | 4-chlorobenzyl | |
| | 2-fluorobenzyl | |
| | 3-fluorobenzyl | |
| | 4-fluorobenzyl | |
| | 2-methylbenzyl | |
| | 3-methylbenzyl | |
| | 4-methylbenzyl | |
| | 2-pyridylmethyl | |
| | 3-pyridylmethyl | |
| | 2,5-dimethoxybenzyl | |
| | 3,4-dimethoxybenzyl | |
| | 3,5-dimethoxybenzyl | |
| | 2,4-dichlorobenzyl | |
| | 2,6-dichlorobenzyl | |
| | 3,4-dichlorobenzyl | |
| | 2,4-dinitrobenzyl | |
| | 3,4-methylenedioxybenzyl | |
| | 2,3-methylenedioxybenzyl | |
| | 3,4,5-trimethoxybenzyl | |
| | 2-phenylethyl | |

TABLE 2-continued

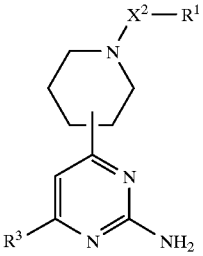

| X² | R¹ | R³ |
|---|---|---|
| | 2-(2-methoxyphenyl)ethyl | |
| | 2-(3-methoxyphenyl)ethyl | |
| | 2-(4-methoxyphenyl)ethyl | |
| | 2-(2,3-dimethoxyphenyl)ethyl | |
| | 2-(3,4-dimethoxyphenyl)ethyl | |
| | 2-(2,3,4-trimethoxyphenyl)ethyl | |
| | 2-(3,4,5-trimethoxyphenyl)ethyl | |
| | 2-(2-chlorophenyl)ethyl | |
| | 2-(4-chlorophenyl)ethyl | |
| | 2-(3,4-dichlorophenyl)ethyl | |
| | 2-(3,4-methylenedioxyphenyl)ethyl | |
| | 3-phenylpropyl | |
| | 3-(4-methoxyphenyl)propyl | |
| | 3-(3,4-dimethoxyphenyl)propyl | |
| | 3-(3,4-methylenedioxyphenyl)propyl | |
| (CO)O | Ph | |
| | —CH₂Ph | |
| (CO)NH | —(CH₂)₇CH₃ | |
| | -Ph | |
| | —CH₂Ph | |
| SO₂ | —(CH₂)₇CH₃ | 4-chlorobenzyl |
| | -Ph | |
| | —CH₂Ph | |
| CO | cyclohexyl | 2-phenylethyl |
| | cyclohexylmethyl | |
| | —CH₃ | |
| | —CH₂CH₃ | |
| | —(CH₂)₂CH₃ | |
| | —(CH₂)₃CH₃ | |
| | —(CH₂)₄CH₃ | |
| | —(CH₂)₅CH₃ | |
| | —(CH₂)₆CH₃ | |
| | —(CH₂)₇CH₃ | |
| | —(CH₂)₈CH₃ | |
| | —(CH₂)₉CH₃ | |
| | —(CH₂)₅OH | |
| | —(CH₂)₆OH | |
| | —(CH₂)₇OH | |
| | —(CH₂)₈OH | |
| | —(CH₂)₉OH | |
| | phenyl | |
| | 2-methoxyphenyl | |
| | 3-methoxyphenyl | |
| | 4-methoxyphenyl | |
| | 2-chlorophenyl | |
| | 3-chlorophenyl | |
| | 4-chlorophenyl | |
| | 2-fluorophenyl | |
| | 3-fluorophenyl | |
| | 4-fluorophenyl | |
| | 2-methylphenyl | |
| | 3-methylphenyl | |
| | 4-methylphenyl | |
| | 2-furyl | |
| | 3-furyl | |
| | 2-pyridyl | |
| | 3-pyridyl | |
| | 4-pyridyl | |
| | 2,3-dimethoxyphenyl | |
| | 2,4-dimethoxyphenyl | |
| | 2,5-dimethoxyphenyl | |
| | 2,6-dimethoxyphenyl | |
| | 3,4-dimethoxyphenyl | |
| | 3,5-dimethoxyphenyl | |

TABLE 2-continued

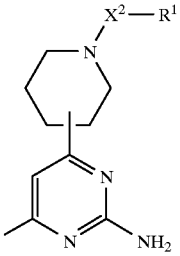

| X² | R¹ | R³ |
|---|---|---|
| | 2,3-dichlorophenyl | |
| | 2,4-dichlorophenyl | |
| | 2,5-dichlorophenyl | |
| | 2,6-dichlorophenyl | |
| | 3,4-dichlorophenyl | |
| | 2,4-dinitrophenyl | |
| | 3,4-methylenedioxyphenyl | |
| | 2,3-methylenedioxyphenyl | |
| | 1-naphthyl | |
| | 2-naphthyl | |
| | 2,3,4-trimethoxyphenyl | |
| | 2,3,6-trimethoxyphenyl | |
| | 2,4,5-trimethoxyphenyl | |
| | 2,4,6-trimethoxyphenyl | |
| | 3,4,5-trimethoxyphenyl | |
| | 2,3,5-trichlorophenyl | |
| | 2,4,6-trichlorophenyl | |
| | benzyl | |
| | 2-methoxybenzyl | |
| | 3-methoxybenzyl | |
| | 4-methoxybenzyl | |
| | 2-chlorobenzyl | |
| | 3-chlorobenzyl | |
| | 4-chlorobenzyl | |
| | 2-fluorobenzyl | |
| | 3-fluorobenzyl | |
| | 4-fluorobenzyl | |
| | 2-methylbenzyl | |
| | 3-methylbenzyl | |
| | 4-methylbenzyl | |
| | 2-pyridylmethyl | |
| | 3-pyridylmethyl | |
| | 2,5-dimethoxybenzyl | |
| | 3,4-dimethoxybenzyl | |
| | 3,5-dimethoxybenzyl | |
| | 2,4-dichlorobenzyl | |
| | 2,6-dichlorobenzyl | |
| | 3,4-dichlorobenzyl | |
| | 2,4-dinitrobenzyl | |
| | 3,4-methylenedioxybenzyl | |
| | 2,3-methylenedioxybenzyl | |
| | 3,4,5-trimethoxybenzyl | |
| | 2-phenylethyl | |
| | 2-(2-methoxyphenyl)ethyl | |
| | 2-(3-methoxyphenyl)ethyl | |
| | 2-(4-methoxyphenyl)ethyl | |
| | 2-(2,3-dimethoxyphenyl)ethyl | |
| | 2-(3,4-dimethoxyphenyl)ethyl | |
| | 2-(2,3,4-trimethoxyphenyl)ethyl | |
| | 2-(3,4,5-trimethoxyphenyl)ethyl | |
| | 2-(2-chlorophenyl)ethyl | |
| | 2-(4-chlorophenyl)ethyl | |
| | 2-(3,4-dichlorophenyl)ethyl | |
| | 2-(3,4-methylenedioxyphenyl)ethyl | |
| | 3-phenylpropyl | |
| | 3-(4-methoxyphenyl)propyl | |
| | 3-(3,4-dimethoxyphenyl)propyl | |
| | 3-(3,4-methylenedioxyphenyl)propyl | |
| (CO)O | Ph | |
| | —CH₂Ph | |
| (CO)NH | —(CH₂)₇CH₃ | |
| | -Ph | |
| | —CH₂Ph | |
| SO₂ | —(CH₂)₇CH₃ | 2-phenyl- |

TABLE 2-continued

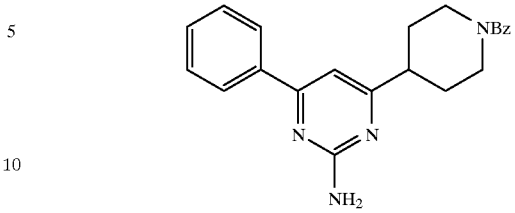

| X² | R¹ | R³ |
|---|---|---|
| | -Ph | ethyl |
| | —CH₂Ph | |
| CO | 3,4-methylene | 4-iodobenzyl |
| | | 4-fluorobenzyl |
| | | 4-methylthio-benzyl |
| | | 4-methylsulfinyl-benzyl |
| | | 4-methylsulfonyl-benzyl |
| | | 4-aminobenzyl |
| | | 4-pyridyl methyl |

Hereinafter the present invention will be described in more detail by referring to the following Examples but is not deemed to be limited thereto. In the chemical formulae illustrated hereinbelow, the symbols "Bz" and "Ac" are used to mean benzoyl and acetyl, respectively. Melting points are uncorrected.

EXAMPLE 1

Synthesis of 2-amino-4-(1-benzoyl-4-piperidinyl)-6-phenylpyrimidine (1) 1-Benzoyl-4-[1-(1,3-dioxo-3-phenylpropyl)]piperidine

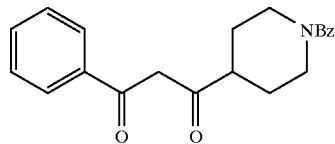

Ethyl 1-benzoylisonipecotate (30 g, 0.115 mol) and acetophenone (13.82 g, 0.115 mol) were dissolved in 320 ml of tetrahydrofuran (THF). To the solution was added sodium hydride (60% dispersion in mineral oil) (4.6 g, 0.115 mol). The mixture was heated at about 60° C. for about 3.5 hours under a nitrogen atmosphere. The reaction mixture was then neutralized with 1N hydrochloric acid and the solvent was removed in vacuo. The residue was partitioned between ethyl acetate and water. The organic layer was dried over sodium sulfate, and the solvent was removed in vacuo. The residue was purified by silica gel column chromatography (hexane:ethyl acetate=8:2). Crystallization from diethyl ether gave the titled compound (11.86 g).

Melting point: 104–105° C. $^1$H-NMR (CDCl₃): δ 1.77 (4H, m), 2.62 (1H, m), 2.99 (2H, m), 3.88 (1H, m), 4.78 (1H, m), 6.21 (1H, s), 7.49 (8H, m), 7.88 (2H, dd, J=1.3, J=6.6), 16.21 (1H, s) (2) 2-Amino-4-(1-benzoyl-4-piperidinyl)-6-phenylpyrimidine

A mixture of 1-benzoyl-4-[1-(1,3-dioxo-3-phenylpropyl)] piperidine (11 g, 0.033 mol), guanidine hydrochloride (6.3 g, 0.066 mol) and potassium carbonate (9.12 g, 0.066 mol) in pyridine (50 ml) was stirred at about 100° C. for about 6 hours. Potassium carbonate (4.56 g, 0.033 mol) and guanidine hydrochloride (3.15 g, 0.033 mol) were further added to the reaction mixture and stirred for about 10 hours at the same temperature. Thereafter dichloromethane and water were added to the reaction mixture followed by extraction. The organic layer was dried over sodium sulfate, and the solvent was removed in vacuo. The residue was purified by silica gel column chromatography (hexane:ethyl acetate= 1:1). Crystallization from isopropyl alcohol gave the titled compound (8.60 g).

Melting point: 147–148° C. $^1$H-NMR (CDCl₃): δ 1.88 (4H, m), 2.77–3.44 (3H, m), 3.93 (1H, m), 4.89 (1H, m), 5.05 (2H, brs), 6.93 (1H, s), 7.45 (8H, m), 7.97 (2H, m)

The resulting free amine compound (600 mg) was dissolved in methanol and acidified with 1 N hydrogen chloride-diethyl ether solution. The solvent was then removed in vacuo. The residue was triturated with methanol-diethyl ether to give the hydrochloride (582 mg) of the titled compounds.

Melting point: 132–13° C.

EXAMPLE 2

Synthesis of 2-amino-4-(1-benzoyl-4-piperidinyl)-6-(4-methoxyphenylmethyl)pyrimidine (1) 1-Benzoyl-4-piperidinecarbonyl chloride A mixture of 1-benzoylisonipecotic acid (60 g, 0.257 mol) thionyl chloride (38 ml) and chloroform (360 ml) was refluxed for about 3 hours. Thereafter the reaction mixture was concentrated in vacuo. Toluene was added to the residue and the mixture was concentrated in vacuo to remove an excess of thionyl chloride. The titled compound was obtained as a crude oil.

(2) 1-Benzoyl-4-{1-[4-(4-methoxyphenyl)-1,3-dioxobutyl]}piperidine

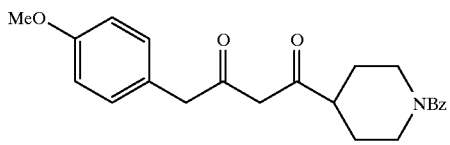

Diisopropylamine (72 ml, 0.514 mol) was dissolved in THF (510 ml). Under a nitrogen atmosphere n-butyl lithium-hexane solution (310 ml, 1.66 mmol/ml) was added dropwise to the solution over a period of about 1.5 hours at about 0° C. After stirring at the same temperature for about 30 minutes, the mixture was cooled to about −78° C. and 4-methoxyphenylacetone (84.4 g, 1.03 mol) was added dropwise over a period of about 1.5 hours and stirred for about 30 minutes. A solution of 1-benzoyl-4-piperidinecarbonyl chloride of Example 2 (1) in THF (510 ml) was added dropwise to the mixture over a period of about 2 hours at the same temperature.

Thirty minutes later conc. hydrochloric acid was added to the reaction mixture. Ethyl acetate and water were then added to the mixture for extraction. The organic layer was washed with water and dried over magnesium sulfate, and then the solvent was removed in vacuo. The residue was purified by silica gel column chromatography (hexane:ethyl acetate=6:4) to give the titled compound (35.5 g) as an oil.

$^1$H-NMR (CDCl$_3$): δ 1.70 (4H, m), 2.38 (1H, m), 2.86 (2H, m), 3.65 (2H, s), 3.75 (1H, m), 3.82 (3H, s), 4.73 (1H, m), 5.43 (1H, s), 6.90 (1H, d, J=7.6), 6.97 (1H, d, J=7.6), 7.18 (1H, d, J=7.6), 7.28 (1H, d, J=7.6),7.40 (5H, m), 15.45 (1H, s)

In this reaction 35.5 g of 1-benzoyl-4-{1-[2-(4-methoxyphenyl)-1,3-dioxobutyl]} piperidine was also obtained as a crystal.

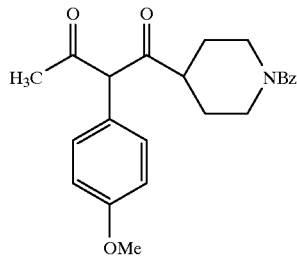

Melting point: 134–137° C. $^1$HNMR (CDCl$_3$): δ 1.56–1.72 (4H, m), 1.88 (3H, s), 2.42 (1H, m), 2.65 (2H, m), 3.70 (1H, m), 3.85 (3H, s), 4.67 (1H, m), 6.92 (2H, d, J=7.9), 7.06 (2H, d, J=7.9), 7.37 (5H, m), 16.86 (1H, s)

(3) 2-Amino-4-(1-benzoyl-4-piperidinyl)-6-(4-methoxyphenylmethyl)pyrimidine

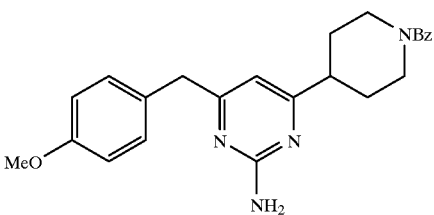

By a procedure similar to that described in Example 1(2) and crystallization from ethanol, the titled compound (15.3 g) was prepared from 1-benzoyl-4-{1-[4-(4-methoxyphenyl)-1,3-dioxobutyl]}piperidine (33 g, 0.084 mol).

Melting point: 170–171° C. $^1$H-NMR (CDCl$_3$): δ 1.75 (4H, m), 2.65 (1H, m), 2.93(2H, m), 3.80 (3H, s), 3.83 (2H, s), 3.85(1H, m), 4.80 (1H, m), 4.94 (2H, brs), 6.26 (1H, s), 6.86 (2H, d, J=8.6), 7.16 (2H, d, J=8.6), 7.40 (5H, m)

The titled compound (250 mg) in methanol was acidified with 1N hydrogen chloride-diethyl ether solution. The solvent was then removed in vacuo. The residue was triturated with tetrahydrofuran-diethyl ether to give the hydorochloride (270 mg) of the titled compound.

Melting point: 169–170° C.

EXAMPLE 3

Synthesis of 2-amino-4-(1-benzoyl-4-piperidinyl)-5-(4-methoxyphenyl)-6-methylpyrimidine

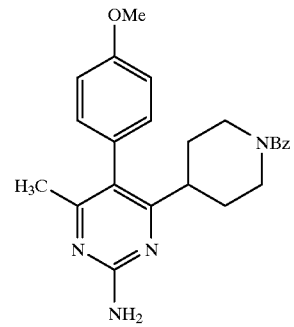

By a procedure similar to that described in Example 1(2) and crystallization from ethanol, the titled compound (2.14 g) was prepared from 1-benzoyl-4-{1-[2-(4-methoxyphenyl)-1,3-dioxobutyl]}piperidine(30 g, 0.076 mol).

Melting point: 226–227° C. $^1$H-NMR (CDCl$_3$): δ 1.63–1.98 (4H, m), 2.52–2.81 (3H, m), 2.08 (3H, s), 3.78 (1H, m), 3.87(3H, s), 4.71 (1H, m), 4.90 (2H, brs), 7.00 (4H, m), 7.39 (5H, m).

The titled compound (50 mg) in methanol was acidified with hydrogen chloride-diethyl ether solution. The solvent was then removed in vacuo. The residue was triturated with tetrahydrofuran-diethyl ether to give the hydrochloride (50 mg) of the titled compound.

EXAMPLE 4

Synthesis of 2-amino-4-(1-benzoyl-4-piperidinyl)-6-(2-phenylethyl)pyrimidine (1) 1-Benzoyl-4-[1-(1,3-dioxo-5-phenylpentyl)]piperidine

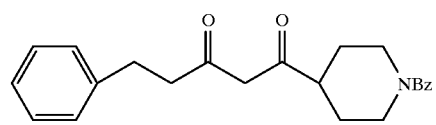

By a procedure similar to that described in Example 2 (1) and (2), the titled compound (29.9 g) as an oil was prepared from 1-benzoylisonipecotic acid (50 g, 0.214 mol) and benzylacetone (38.06 g, 0.257 mol).

$^1$H-NMR (CDCl$_3$): δ 1.63 (3H, m), 2.43 (1H, m), 2.63 (2H, t, J=7.3), 2.91 (5H, m), 3.83 (1H, m), 4.71 (1H, m), 5.46 (1H, s), 7.30 (10H, m), 15.48 (1H, brs)

(2) 2-Amino-4-(1-benzoyl-4-piperidinyl)-6-(2-phenylethyl)pyrimidine

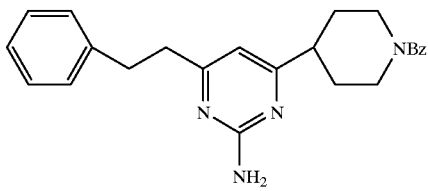

By a procedure similar to that described in Example 1(2) and crystallization from ethanol, the titled compound (23.8 g) was prepared from 1-benzoyl-4-[1-(1,3-dioxo- 5-phenyl-pentyl)]piperidine (29 g, 0.080 mol).

Melting point: 104–106° C. ¹H-NMR (CDCl₃): δ 1.78 (4H, m), 2.67 (1H, m), 2.84–3.01 (6H, m), 3.85 (1H, m), 4.80 (1H, m), 4.93 (2H, brs), 6.27 (1H, s), 7.17–7.42 (10H, m)

The titled compound (400 mg) in methanol was acidified with 1N hydrogen chloride-diethyl ether solution. The solvent was then removed in vacuo. The residue was triturated with tetrahydrofuran-diethyl ether to give of the hydrochloride (437 mg) of the titled compound.

Melting point: 216–217° C.

EXAMPLE 5

Synthesis of 2-amino-4-(1-benzoyl-4-piperidinyl)-6-(4-methoxyphenyl)pyrimidine (1) 1-Benzoyl-4-{1-[3-(4-methoxyphenyl)-1,3-dioxopropyl]}piperidine

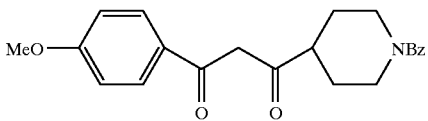

By a procedure similar to that described in Example 2(1) and (2) and crystallization from diethyl ether, the titled compound (11.67 g) was prepared from 1-benzoylisonipecotic acid (15.16 g, 0.065 mol) and 4'-methoxyacetophenone (19.52 g, 0.13 mol).

Melting point: 226–227° C. ¹H-NMR (CDCl₃): δ 1.76 (4H, m), 2.58 (1H, m), 2.91 (2H, m), 3.88 (4H, m), 4.78 (1H, m), 6.14 (1H, s), 6.95 (2H, d, J=8.6), 7.42 (5H, m), 7.87 (2H, d, J=8.6), 16.38 (1H, s)

(2) 2-Amino-4-(1-benzoyl-4-piperidinyl)-6-(4-methoxyphenyl)pyrimidine

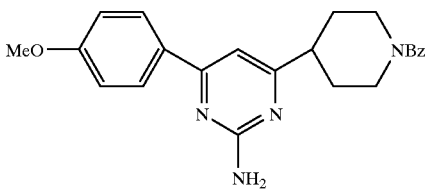

By a procedure similar to that described in Example 1(2) and crystallization from ethanol, the titled compound (7.81 g) was prepared from 1-benzoyl-4-{1-[3-(4-methoxyphenyl)-1,3-dioxopropyl]}piperidine (10 g, 0.027 mol).

Melting point: 165–166° C. ¹H-NMR (CDCl₃): δ 1.88 (4H, m), 2.79 (1H, m), 3.00(2H, m), 3.87 (4H, m), 4.90 (1H, m),5.02 (2H, s), 6.87 (1H, s), 6.98 (2H, d, J=8.6), 7.43 (5H, m), 7.96(2H, d, J=8.6).

The titled compound (110 mg) in chloroform was acidified with 1N-hydrogen chloride-diethyl ether solution. The solvent was removed in vacuo. The residue was triturated with chloroform-diethyl ether to give the hydrochloride (100 mg) of the titled compound.

Melting point: 249–253° C.

EXAMPLE 6

Synthesis of 2-amino-4-(1-benzoyl-4-piperidinyl)-6-(4-chlorophenyl)pyrimidine (1) 1-Benzoyl-4-{1-[3-(4-chlorophenyl)-1,3-dioxopropyl]}piperidine

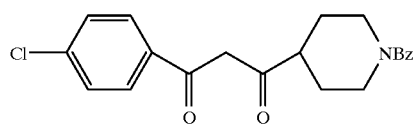

By a procedure similar to that described in Example 2(1) and (2) and crystallization from diethyl ether, the titled compound (11.92 g) was prepared from 1-benzoylisonipecotic acid (15.16 g, 0.065 mol) and 4'-chloroacetophenone (20.98 g, 0.13 mol).

Melting point: 129–130° C. ¹H-NMR (CDCl₃): δ 1.77 (4H, m), 2.62 (1H, m), 2.95 (2H, m), 3.88 (1H, m), 4.78 (1H, m), 6.16 (1H, s), 7.44 (7H, m), 7.83(2H, d, J=8.6), 16.16 (1H, s).

(2) 2-Amino-4-(1-benzoyl-4-piperidinyl)-6-(4-chlorophenyl)pyrimidine

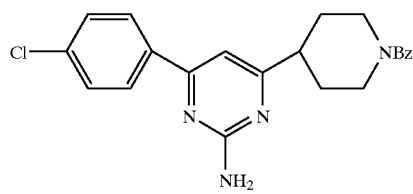

By a procedure similar to that described in Example 1(2) and crystallization from isopropanol, the titled compound (7.25 g) was prepared from 1-benzoyl-4-{1-[3-(4-chlorophenyl)-1,3-dioxopropyl]}piperidine(10 g, 0.027 mol).

Melting point: 210–211° C. ¹H-NMR (CDCl₃): δ 1.87 (4H, m), 2.81 (1H, m),3.00 (2H, m), 3.90 (1H, m), 4.87 (1H, m), 5.08 (2H, s), 6.89 (1H, s),7.44 (7H, m), 7.94 (2H, d, J=8.6).

The titled compound (110 mg) in chloroform was acidified with 1N-hydrogen chloride-diethyl ether solution. The solvent was removed in vacuo. The residue was triturated with chloroform-diethyl ether to give the hydrochloride (85 mg) of the titled compound.

Melting point: 238–239° C.

EXAMPLE 7

Synthesis of 2-amino-4-(1-benzoyl-4-piperidinyl)-6-(4-chlorophenylmelthyl)pyrimidine (1) 1-Benzoyl-4-{1-[4-(4-chlorophenyl)-1,3-dioxobutyl]}piperidine

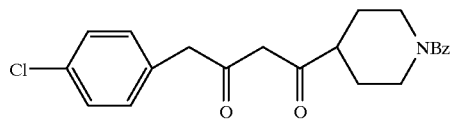

By a procedure similar to that described in Example 2(1) and (2), the title compound (9.86 g) was prepared from 1-benzoylisonipecotic acid (27.64 g, 0.119 mol) and 4'-chlorophenylacetone (40 g, 0.237 mol).

$^1$H-NMR (CDCl$_3$): δ 1.55–1.90 (4H, m), 2.41 (1H, m), 2.92 (2H, m), 3.58 (2H, s), 3.78(1H, m), 4.71 (1H, m), 5.44 (1H, s), 7.17(2H, d, J=8.6), 7.27 (2H, d, J=8.6),7.40 (5H, m), 15.37 (1H, s).

(2) 2-Amino-4-(1-benzoyl-4-piperidinyl)-6-(4-chlorophenylmethyl)pyrimidine

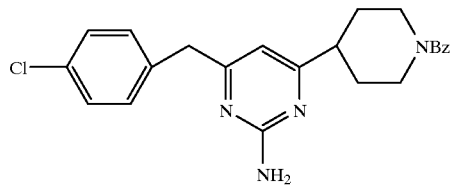

By a procedure similar to that described in Example 1(2) and crystallization from methanol, the titled compound (5.54 g) was prepared from 1-benzoyl-4-{1-[4-(4-chlorophenyl)-1,3-dioxobutyl]}piperidine (9.0 g, 0.023 mol).

$^1$H-NMR (CDCl$_3$): δ 1.76 (4H, m), 2.66 (1H, m), 2.86 (2H, m), 3.85 (2H, s), 3.90 (1H, m), 4.80 (1H, m), 4.99 (2H, brs), 6.26(1H, s), 7.18 (2H, d, J=8.3), 7.28(2H, d, J=8.3), 7.40 (5H, m). The titled compound (180 mg) in chloroform was acidified with 1N-hydrogen chloride-diethyl ether solution. The solvent was removed in vacuo. The residue was triturated with chloroform-diethyl ether to give the hydrochloride (194 mg) of the titled compound.

Melting point: 148–150° C.

EXAMPLE 8

Synthesis of 2-amino-4-(1-benzoyl-4-piperidinyl) quinazoline (1) 1-Benzoyl-4-cyanopiperidine

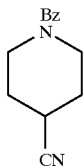

By a procedure similar to that described later in Reference Example 1 and crystallization from isopropanol, the titled compound (73.5 g) was prepared from 4-cyanopiperidine(40 g, 0.363 mol).

$^1$H-NMR (CDCl3): δ 1.91 (4H, m), 2.93 (1H, m), 3.20–4.10 (4H, m), 7.40 (5H, m)

(2) 1-Benzoyl-4-(2-aminobenzoyl)piperidine

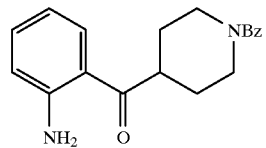

To an ice cold solution of boron trichloride (26.3 ml, 0.303 mol) in 300 ml of 1,2-dichloroethane was added dropwise aniline (28.21 g, 0.303 mol) over a period of about 15 minutes under a nitrogen atmosphere. Then to the solution was added portionwise 1-benzoyl-4-cyanopiperidine (50 g, 0.233 mol) and aluminum chloride (40.39 g, 0.303 mol) successively. After stirring at room temperature for about 15 minutes, the mixture was refluxed for about 14 hours. After 1N hydrochloric acid aqueous solution was added to the reaction mixture at about ice cooling temperature, the mixture was refluxed for about an hour. To the reaction mixture 3N sodium hydroxide was added to make basic. The resulting slurry was filtered over Celite. The filtrate was extracted with dichloromethane. The organic layer was dried over sodium sulfate, and the solvent was removed in vacuo. The residue was crystallized from ethanol to give 51.4 g of the titled compound.

Melting point: 138–138.5° C. $^1$H-NMR (CDCl$_3$): δ 1.64–1.90 (4H, m), 3.07 (2H, m),3.56 (1H, m), 3.92 (1H, m), 4.75 (1H, m), 6.31 (2H, brs), 6.64 (2H, t, J=7.6), 7.25–7.41 (6H, m), 7.74 (1H, d, J=7.6)

(3) 2-Amino-4-(1-benzoyl-4-piperidinyl)quinazoline

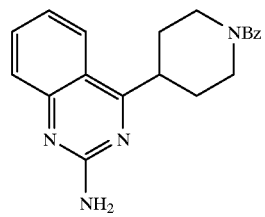

The titled compound was prepared by warming a mixture of 1-benzoyl-4-(2-aminobenzoyl)piperidine hydrochloride (17 g, 0.049 mol) and cyanamide (4.12 g, 0.098 mol). At about 50° C., vigorous exothermic reaction occurred. After the reaction was finished, the reaction mixture was cooled, water was added to the reaction mixture, and then added sodium hydrogencarbonate to make the mixture basic. The mixture was then extracted with dichloromethane. The organic layer was washed with aqueous solution of saturated sodium chloride, and then dried over sodium sulfate and evaporated in vacuo. The residue was purified by silica gel column chromatography (hexane:ethyl acetate=1:1) to give the titled compound (15.9 g) as a foam.

$^1$H-NMR (CDCl$_3$): δ 1.80–2.10 (4H, m), 3.20 (2H, m), 3.70 (1H, m), 3.96 (1H, m), 4.89 (1H, m), 5.13 (2H, brs), 7.26–7.71 (9H, m)

EXAMPLE 9

Synthesis of 2-amino-4-(1-benzoyl-4-piperidinyl)-6-methoxyquinazoline (1) 1-Benzoyl-4-(2-amino-5-methoxybenzoyl)piperidine

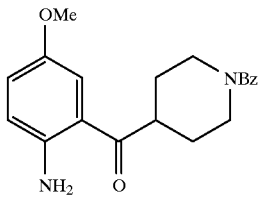

By a procedure similar to that described in Example 8(2), the title compound (8.12 g) was prepared from 4-methoxyaniline (10.26 g, 0.083 mol) and 1-benzoyl-4-cyanopiperidine (21.53 g, 0.10 mol).

$^1$H-NMR (CDCl$_3$): δ 1.60–1.95 (4H, m), 2.95 (2H, m), 3.41 (1H, m), 3.69 (3H, s), 3.75(1H, m), 4.65 (1H, m), 5.95 (2H, brs), 6.57 (1H, d, J=8.9), 6.90 (1H, dd, J=8.9, J=3.0), 7.12 (1H, d, J=3.0), 7.30 (5H, m).

(2) 2-Amino-4-(1-benzoyl-4-piperidinyl)-6-methoxyquinazoline

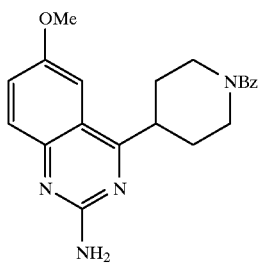

By a procedure similar to that described in Example 8(3), the titled compound (4.15 g) was prepared from 1-benzoyl-4-(2-amino-5-methoxybenzoyl)piperidine hydrochloride (4.51 g, 0.012 mol).

Melting point: 172–173° C. $^1$H-NMR (CDCl$_3$): δ 1.88–2.08 (4H, m), 3.07 (2H, m), 3.61 (1H, m), 3.92 (3H, s), 3.95 (1H, m), 5.00 (3H, m), 7.19 (1H, d, J=2.4), 7.27–7.50 (6H, m), 7.56 (1H, d, J=9.2).

EXAMPLE 10

Synthesis of 2-amino-4-(1-benzoyl-4-piperidinyl)-6-chloroquinazoline (1) 1-Benzoyl-4-(2-amino-5-chlorobenzoyl)piperidine

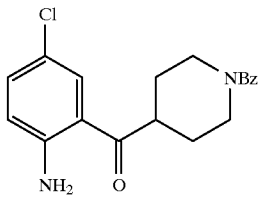

By a procedure similar to that described in Example 8(2), the titled compound (808 mg) was prepared from 4-chloroaniline (2.18 g, 0.017 mol) and 1-benzoyl-4-cyanopiperidine (4.03 g, 0.018 mol).

$^1$H-NMR (CDCl$_3$): δ 1.76–1.99 (4H, m), 2.98 (2H, m), 3.46 (1H, m), 3.83 (1H, m), 4.72 (1H, m), 6.40 (2H, brs), 6.61 (1H, d, J=8.9), 7.17 (1H, dd, J=8.9, J=2.2), 7.40 (5H, m), 7.64 (1H, d, J=2.2).

(2) 2-Amino-4-(1-benzoyl-4-piperidinyl)-6-chloroquinazoline

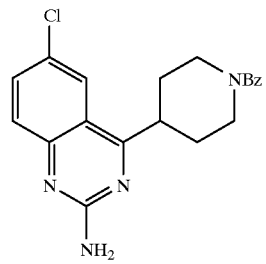

By a procedure similar to that described in Example 8(3), the titled compound (477 mg) was prepared from 1-benzoyl-4-(2-amino-5-methoxybenzoyl)-piperidine hydrochloride (800 mg, 2.1 mmol).

Melting point: 155–158° C. $^1$H-NMR (CDCl$_3$): δ 1.80–2.12 (4H, m), 3.14 (2H, m), 3.61 (1H, m), 3.96 (1H, m), 4.91 (1H, m), 5.15 (2H, s), 7.42–7.65 (7H, m), 7.90 (1H, d, J=2.0).

EXAMPLE 11

Synthesis of 4-(1-acetyl-4-piperidinyl)-2-aminoquinazoline (1) 2-Amino-4-(4-piperidinyl)quinazoline

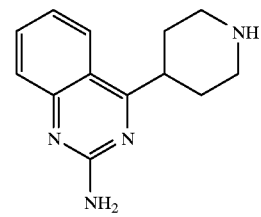

A mixture of 2-amino-4-(1-benzoyl-4-piperidinyl) quinazoline (24 g, 0.072 mol) obtained in Example 8 (3), ethanol (250 ml) and 6N sodium hydroxide aqueous solution (250 ml) was refluxed for about 7 hours under a nitrogen atmosphere. Thereafter ethanol was removed from the reaction mixture in vacuo. The residue was extracted with dichloromethane. The organic layer was washed with saturated sodium chloride aqueous solution, and then dried over magnesium sulfate and evaporated in vacuo. The residue was crystallized from isopropyl alcohol to give 13.0 g of the titled compound.

Melting point: 184–186° C. $^1$H-NMR (CDCl$_3$): δ 1.78–1.96 (5H, m), 2.85 (2H, ddd, J=3.3, J=11.9, J=11.9), 3.26 (2H, dd, J=3.3, J=11.9), 3.56 (1H, m), 5.14 (2H, brs), 7.27 (1H, dd, J=8.3, J=5.9), 7.57–7.69 (2H, m), 7.96 (1H, d, J=8.3)

(2) 4-(1-Acetyl-4-piperidinyl)-2-aminoquinazoline

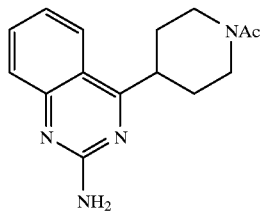

To an ice-cold solution of 2-amino-4-(4-piperidyl)quinazoline (500 mg, 2.19 mmol) and triethylamine (233 mg, 2.3 mmol) in N,N-dimethylformamide (10 ml) was added dropwise acetic anhydride (0.22 ml, 2.30 mmol) under a nitrogen atmosphere. The reaction mixture was stirred for about 3 hours and was evaporated. The residue was partitioned between dichloromethane and saturated sodium hydrogencarbonate aqueous solution. The organic layer was washed with water and then dried over sodium sulfate and evaporated in vacuo. The residue was crystallized from ethanol. Recrystallization from methanol gave the titled compound(452 mg).

Melting point: 239–240° C. $^1$H-NMR (CDCl$_3$): δ 1.96 (4H, m), 2.16 (3H, s), 2.77 (1H, m), 3.30 (1H, m), 3.66 (1H, m), 4.00 (1H, m), 4.79 (1H, m), 5.12 (2H, brs), 7.28 (1H, m), 7.65 (2H, m), 7.94 (1H, d, J=7.9)

The titled compound (290 mg) in methanol was acidified with 1N hydrogen chloride-diethyl ether solution. The solvent was then removed in vacuo. The residue was crystallized from isopropyl alcohol to give the hydrochloride (324 mg) of the titled compound.

Melting point: 275° C. (decomposed)

EXAMPLE 12

Synthesis of 2-amino-4-[1-(3,4-methylenedioxyphenylacetyl)-4-piperidinyl]quinazoline

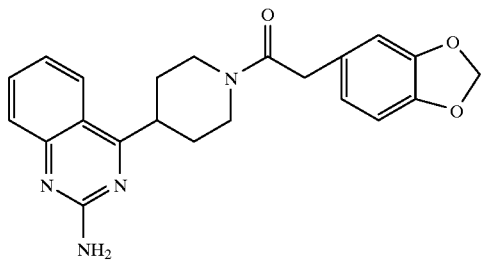

To a suspension of 3,4-methylenedioxyphenylacetic acid (569 mg, 3.16 mmol) in chloroform (6 ml) was added thionyl chloride (1.2 ml). The mixture was refluxed for about 3 hours, and was evaporated. Toluene was added to the residue and the mixture was evaporated to remove the excess of thionyl chloride. To the residue was added dichloromethane (3 ml) to give a dichloromethane solution of 3,4-methylenedioxyphenylacetyl chloride. To an ice-cold mixture of 2-amino-4-(4-piperidinyl)quinazoline (600 mg, 2.63 mmol) and triethylamine (319 mg, 3.16 mmol) in dichloromethane (16 ml) was added dropwise the solution of 3,4-methylenedioxyphenylacetyl chloride prepared above under a nitrogen atmosphere. The mixture was stirred for about two hours and to the reaction mixture was added dichloromethane and saturated sodium hydrogencarbonate aqueous solution followed by extraction. The organic layer was washed with water, and then dried over sodium sulfate and evaporated in vacuo. The residue was purified by silica gel column chromatography (dichloromethane:methanol=30:1). Crystallization from methanol gave the titled compound (617 mg).

Melting point: 167–168° C. $^1$H-NMR (CDCl$_3$): δ 1.89 (4H, m), 2.83 (1H, m), 3.21(1H, m), 3.59 (1H, m), 3.70 (2H, s), 4.05 (1H, m), 4.79 (1H, m), 5.10 (2H, brs), 5.95 (2H, s), 6.75 (3H, m), 7.27 (1H, m), 7.59 (1H, d, J=7.6), 7.67 (1H, m), 7.90 (1H, d, J=7.6)

The titled compound (260 mg) in methanol was acidified with 1N hydrogen chloride-diethyl ether solution The solvent was then removed in vacuo. Crystallization from ethanol gave the hydrochloride (280 mg) of the titled compound.

Melting point: 157–160° C.

EXAMPLE 13

Synthesis of 2-amino-4-[1-(3,4-dihydroxyphenylacetyl)-4-piperidinyl]quinazoline

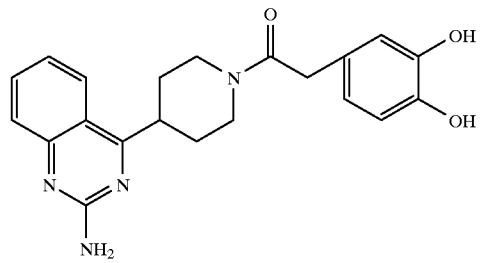

To an ice-cold solution of 2-amino-4-(4-piperidinyl)quinazoline (600 mg, 2.63 mmol) obtained in example 11(1), 3,4-dihydroxyphenylacetic acid (530 mg, 3.16 mmol) and 4-dimethylaminopyridine (386 mg, 3.16 mmol) in dimethylformamide (20 ml) was added 1-ethyl-3-(N,N'-dimethylaminopropyl)carbodiimide hydrochloride (605 mg, 3.16 mmol) under a nitrogen atmosphere. The mixture was stirred overnight at room temperature. The solvent was removed in vacuo and the residue was crystallized from methanol to give the titled compound (599 mg).

Melting point: 250–253° C. $^1$H-NMR (DMSO-d$_6$): δ 1.72 (4H, m), 2.79 (1H, m), 3.17–3.58 (3H, m), 3.76 (1H, m), 4.06 (1H, m), 4.54 (1H, m), 6.51 (1H, d, J=7.9), 6.66 (4H, m), 7.20 (1H, dd, J=6.9, J=7.3), 7.41 (1H, d, J=7.3), 7.64 (1H, dd, J=6.9, J=7.6), 8.07 (1H, d, J=7.6), 8.79 (2H, brs).

The titled compound (200 mg) in methanol was acidified with 1N-hydrogen chloride-diethylether solution. The solvent was removed in vacuo. Crystallization from ethanol gave the hydrochloride (150 mg) of the titled compound.

EXAMPLES 14 to 267

(1) 2-Amino-4-phenyl-6-(4-piperidinyl)pyrimidine

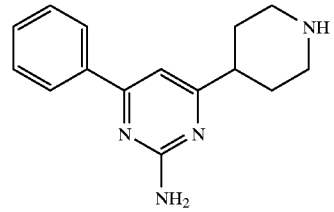

By a procedure similar to that described in Example 11(1) and crystallization from methanol, the titled compound (4.8 g) was prepared from 2-amino-4-(1-benzyl-4-piperidinyl)-6-phenylpyrimidine (7 g, 20 mmol) obtained in Example 1 (2).

Melting point: 165–170° C. $^1$H-NMR (CDCl$_3$): δ 1.73 (3H, m), 1.92 (2H, m), 2.66 (1H, m), 2.75 (2H, dt, J=2.6, J=12.2), 3.12 (2H, m), 5.04 (2H, brs), 6.94 (1H, s), 7.46 (3H, m), 7.97 (2H, m)

(2) 2-Amino-4-(4-methoxyphenylmethyl)-6-(4-piperidinyl) pyrimidine

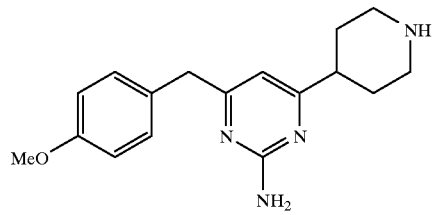

By a procedure similar to that described in Example 11(1) and crystallization from isopropyl alcohol-diethyl ether, the titled compound (8.81 g) was prepared from 2-amino-4-(1-benzoyl-4-piperidinyl)-6-(4-methoxyphenyl-methyl) pyrimidine (15 g, 37 mmol) obtained in Example 2 (3).

Melting point: 112–113° C. $^1$H-NMR (CDCl$_3$): δ 1.57 (3H, m), 1.79 (2H, m), 2.50 (1H, m), 2.67 (2H, dt, J=12.2, J=2.3), 3.14 (2H, m), 3.80 (3H, s), 3.83 (2H, s),4.96 (2H, brs), 6.28 (1H, s), 6.85 (2H, d,J=8.9), 7.16 (2H, d, J=8.9)

(3) 2-Amino-4-(2-phenylethyl)-6-(4-piperidinyl)pyrimidine

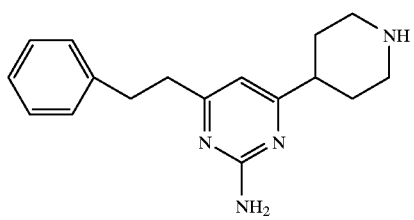

By a procedure similar to that described in Example 11(1) and crystallization from isopropyl alcohol-diethyl ether, the titled compound (10.8 g) was prepared from 2-amino-4-(1-benzyl-4-piperidinyl)-6-(2-phenylethyl)pyrimidine (22 g, 57 mmol) obtained in Example 4(2).

Melting point: 205° C.(decomposed) $^1$H-NMR (DMSO-d$_6$): δ 1.84 (4H, m), 2.73 (3H, m), 2.92 (4H, m), 3.28 (2H, d, J=12.5), 6.36 (1H, s), 6.50 (2H, s), 7.23 (5H, m), 8.99 (1H, brs)

(4) 2-Amino-4-methyl-5-(4-methoxyphenyl)-6-(4-piperidinyl)pyrimidine

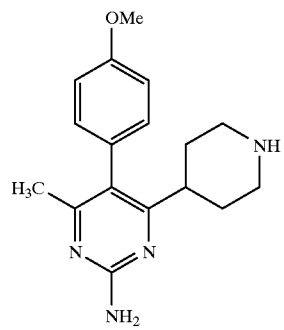

By a procedure similar to that described in Example 11(1) and crystallization from isopropanoldiethyl ether, the titled compound (1.24 g) was prepared from 2-amino-4-(1-benzoyl-4-piperidinyl)-5-(4-methoxyphenyl)-6-methylpyrimidine (1.9 g, 4.7 mmol) obtained in Example 3.

Melting point: 191–192° C. $^1$H-NMR (CDCl$_3$): δ 1.71 (5H, m), 2.06 (3H, s), 2.45 (3H, m), 3.04 (2H, m), 3.87 (3H, s), 4.87 (2H, brs), 6.99 (4H, m).

(5) 2-Amino-4-(4-methoxyphenyl)-6-(4-piperidinyl) pyrimidine

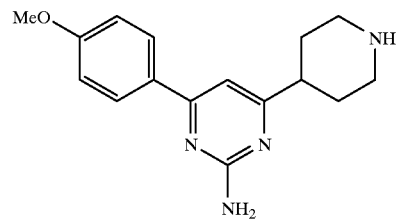

By a procedure similar to that described in Example 11(1) and crystallization from isopropanol, the title compound (3.73 g) was prepared from 2-amino-4-(1-benzoyl-4-piperidinyl)-6-(4-methoxyphenyl)pyrimidine(7.0 g, 0.018 mol) obtained in Example 5(2).

Melting point: 185–187° C. $^1$H-NMR (CDCl$_3$): δ 1.73 (3H, m), 1.92 (2H, m), 2.64 (1H, m), 2.74 (2H, m), 3.21 (2H, m), 3.87 (3H, s), 5.03 (2H, brs), 6.89 (1H, s), 6.98 (2H, d, J=8.6), 7.96 (2H, d, J=8.6).

(6) 2-Amino-4-(4-chlorophenyl)-6-(4-piperidinyl)-pyrimidine

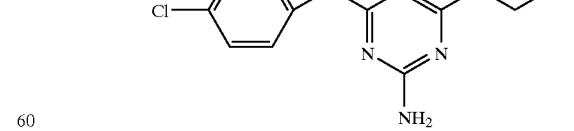

By a procedure similar to that described in Example 11(1) and crystallization from isopropanol, the titled compound (4.47 g) was prepared from 2-amino-4-(1-benzoyl-4-piperidinyl)-6-(4-chlorophenyl)pyrimidine (7.0 g, 0.018 mol) obtained in Example 6(2).

Melting point: 205–207° C. $^1$H-NMR (CDCl$_3$): δ 1.72 (3H, m), 1.91 (2H, m), 2.74 (3H, m), 3.21 (2H, m), 5.07(2H, brs), 6.90 (1H, s), 7.43 (2H, d, J=8.6), 7.93 (2H, d, J=8.6).

(7) 2-Amino-4-(4-chlorophenylmethyl)-6-(4-piperidinyl) pyrimidine

By a procedure similar to that described in Example 11(1) and crystallization from ethanol-diethyl ether, the title compound (3.01 g) was prepared from 2-amino-4-(-benzoyl-4-piperidinyl)-6-(4-chlorophenylmethyl) pyrimidine (5.3 g, 0.013 mol) obtained in Example 7(2).

Melting point: 147–147.5° C. $^1$H-NMR (CDCl$_3$): δ 1.60 (3H, mn), 1.80 (2H, mn), 2.51 (1H, mn), 2.68 (2H, dt, J=2.6, 12.2), 3.15 (2H, m), 3.84 (2H, s), 5.00 (2H, brs), 6.27 (1H, s), 7.17 (2H, d, J=8.6), 7.27 (2H, d, J=8.6).

(8) 2-Amino-6-methoxy-4-(4-piperidinyl)quinazoline

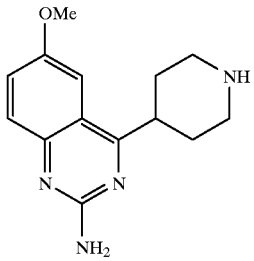

By a procedure similar to that described in Example 11(1), the titled compound (2.60 g) was prepared from 2-amino-4-(1-benzoyl-4-piperidinyl)-6-methoxyquinazoline (4.15 g, 0.011 mol) obtained in Example 9(2).

Melting point: 213–216° C.

(9) 2-Amino-6-chloro-4-(4-piperidinyl)-quinazoline

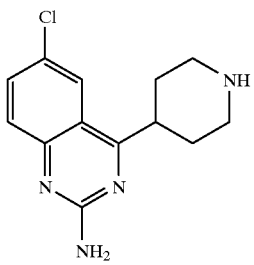

By a procedure similar to that described in Example 11(1), the title compound (440 mg) was prepared from 2-amino-4-(1-benzoyl-4-piperidinyl)-6-chloroquinazoline (477 mg, 1.2 mmol) obtained in Example 10(2).

$^1$H-NMR (CDCl$_3$): δ 1.85–2.00 (4H, m), 2.85 (2H, m), 3.25 (2H, m), 3.45 (1H, m), 5.10 (2H, brs), 7.58 (2H, s), 7.90 (1H, d, J=2.3).

(10) The compounds shown in Tables 3–5 were prepared by a procedure similar to that described in Example 12 and Example 13 treating the piperidyl derivatives obtained hereinabove such as 2-amino-4-(4-piperidinyl)quinazoline, 2-amino-6-methoxy-4-(4-piperidinyl)-quinazoline, 2-amino-6-chloro-4-(4-piperidinyl)-quinazoline, 2-amino-4-phenyl-6-(4-piperidinyl)pyrimidine, 2-amino-4-(4-methoxyphenyl)-6-(4-piperidinyl)pyrimidine, 2-amino-4-(4-chlorophenyl)-6-(4-piperidinyl)-pyrimidine, 2-amino-4-methyl-5-(4-methoxyphenyl)-6-(4-piperidinyl)pyrimidine, 2-amino-4-(4-methoxyphenylmethyl)-6-(4-piperidinyl)pyrimidine, 2-amino-4-(4-chlorophenylmethyl)-6-(4-piperidinyl)pyrimidine, 2-amino-4-(2-phenylethyl)-6-(4-piperidinyl)pyrimidine with various acid chlorides or carboxylic acids.

The acid chlorides may be prepared from the corresponding carboxylic acids in a conventional method well known to a skilled person in the art of organic chemistry, or some of them are commercially available.

TABLE 3

| Example No | R$^1$ | R$^6$ | Yield (%) | M.P. (° C.) |
|---|---|---|---|---|
| 14 | Cyclohexyl | H | 65 | 203–204 |
| 15 | Cyclohexylmethyl | | 77 | 195–196 |
| 16 | —CH$_2$CH$_3$ | | 65 | 229–230 |
| 17 | —(CH$_2$)$_2$CH$_3$ | | 62 | 222–223 |
| 18 | —(CH$_2$)$_3$CH$_3$ | | 65 | 216–217 |
| 19 | —(CH$_2$)$_4$CH$_3$ | | 72 | 152–155 |
| 20 | —(CH$_2$)$_5$CH$_3$ | | 84 | amorphous |
| 21 | —(CH$_2$)$_6$CH$_3$ | | 77 | amorphous |
| 22 | —(CH$_2$)$_7$CH$_3$ | | 68 | amorphous |
| 23 | —(CH$_2$)$_8$CH$_3$ | | 84 | 87–90 |
| 24 | —(CH$_2$)$_9$CH$_3$ | | 90 | 91–92 |
| 25 | i-Propyl | | 85 | 217–218 |
| 26 | t-Butyl | | 98 | 249–253 |
| 27 | —(CH$_2$)$_6$NHBoc | | 95 | amorphous |
| 28 | —(CH$_2$)$_7$NHBoc | | 72 | amorphous |
| 29 | —(CH$_2$)$_{10}$NHBoc | | 96 | amorphous |
| 30 | —(CH$_2$)$_9$OH | | 80 | 117–118 |
| 31 | —CH$_2$OCH$_3$ | | 48 | 180–181 |
| 32 | 2-methoxyphenyl | | 84 | 254–256 |
| 33 | 3-methoxyphenyl | | 87 | amorphous |
| 34 | 4-methoxyphenyl | | 80 | 172–172.5 |
| 35 | 2-chlorophenyl | | 60 | amorphous |
| 36 | 3-chlorophenyl | | 86 | amorphous |
| 37 | 4-chlorophenyl | | 93 | 200.5–202 |
| 38 | 2-nitrophenyl | | 97 | amorphous |
| 39 | 3-nitrophenyl | H | 99 | amorphous |
| 40 | 4-nitrophenyl | | 87 | 203–204 |
| 41 | 2-fluorophenyl | | 96 | 193–195 |
| 42 | 3-fluorophenyl | | 99 | amorphous |
| 43 | 4-fluorophenyl | | 83 | amorphous |
| 44 | 2-methylphenyl | | 88 | 213–214 |
| 45 | 3-methylphenyl | | 86 | 178–179 |
| 46 | 4-methylphenyl | | 86 | 230–231 |
| 47 | 2-furyl | | 69 | 217–218 |
| 48 | 3-furyl | | 59 | 215–216 |
| 49 | 2-pyridyl | | 60 | 235–236 |
| 50 | 3-pyridyl | | 96 | 177–179 |
| 51 | 4-pyridyl | | 94 | 220–222 |
| 52 | 2,3-dimethoxyphenyl | | 85 | 205–207 |
| 53 | 2,4-dimethoxyphenyl | | 24 | 250–252 |
| 54 | 2,5-dimethoxyphenyl | | 69 | 201–203 |
| 55 | 2,6-dimethoxyphenyl | | 76 | 232–234 |
| 56 | 3,4-dimethoxyphenyl | | 71 | 173–175 |
| 57 | 3,5-dimethoxyphenyl | | 86 | 173–174 |
| 58 | 2,3-dichlorophenyl | | 79 | 256–258 |
| 59 | 2,4-dichlorophenyl | | 92 | 196–197 |
| 60 | 2,5-dichlorophenyl | | 97 | 125–128 |
| 61 | 2,6-dichlorophenyl | | 20 | 232–234 |
| 62 | 3,4-dichlorophenyl | | 100 | 192–193 |
| 63 | 3,5-dichlorophenyl | | 93 | 144–146 |
| 64 | 2,4-dinitrophenyl | H | 62 | 204–206 |
| 65 | 3,4-methylenedioxyphenyl | | 45 | 197–198 |
| 66 | 1-naphthyl | | 84 | 214–215 |
| 67 | 2-naphthyl | | 81 | 230–231 |
| 68 | 2,3,4-trimethoxyphenyl | | 57 | amorphous |
| 69 | 2,3,6-trimethoxyphenyl | | 57 | 230–231.5 |
| 70 | 2,4,5-trimethoxyphenyl | | 31 | 105–108 |
| 71 | 2,4,6-trimethoxyphenyl | | 29 | 125–127 |
| 72 | 3,4,5-trimethoxyphenyl | | 88 | 199–202 |
| 73 | 2,3,5-trichlorophenyl | | 87 | 241–242 |
| 74 | 2,3,6-trichlornphenyl | | 33 | 225–227 |
| 75 | 2,4,6-trichlorophenyl | | 40 | 213–214 |

TABLE 3-continued

Structure: piperidine with N-COR¹ substituent, 4-position connected to quinazoline (with R⁶ at 6-position and 2-NH₂)

| Example No | R¹ | R⁶ | Yield (%) | M.P. (°C.) |
|---|---|---|---|---|
| 76 | Benzyl | | 53 | 225–226 |
| 77 | 2-methoxybenzyl | | 97 | amorphous |
| 78 | 3-methoxybenzyl | | 100 | amorphous |
| 79 | 4-methoxybenzyl | | 90 | 220–221 |
| 80 | 2-chlorobenzyl | | 99 | 187–188 |
| 81 | 3-chlorobenzyl | | 92 | 190–191 |
| 82 | 4-chlorobenzyl | | 89 | 206–207 |
| 83 | 2-fluorobenzyl | | 98 | 204–205 |
| 84 | 3-fluorobenzyl | | 89 | 207.5–209 |
| 85 | 4-fluorobenzyl | | 96 | 196–198 |
| 86 | 2-nitrobenzyl | | 79 | 202–203 |
| 87 | 3-nitrobenzyl | | 99 | amorphous |
| 88 | 4-nitrobenzyl | H | 94 | 205–206 |
| 89 | 2-pyridylmethyl | | 77 | 168–170 |
| 90 | 3-pyridylmethyl | | 99 | 232–235 |
| 91 | 2,5-dimethoxybenzyl | | 94 | 147–148 |
| 92 | 3,4-dimethoxybenzyl | | 98 | 158–159 |
| 93 | 3,5-dimethoxybenzyl | | 95 | 108–110 |
| 94 | 2,4-dichlorobenzyl | | 84 | 224–225 |
| 95 | 2,6-dichlorobenzyl | | 80 | 202–203 |
| 96 | 3,4-dichlorobenzyl | | 98 | 149–150 |
| 97 | 2,4-dinitrobenzyl | | 69 | 229–231 |
| 98 | 2,3,6-trichlorobenzyl | | 80 | 208–209 |
| 99 | 3,4,5-trimethoxybenzyl | | 49 | 188–189 |
| 100 | 2-phenylethyl | | 69 | amorphous |
| 101 | 2-(3,4-methylene-dioxyphenyl)ethyl | | 71 | 160–163 |
| 102 | 3-phenylpropyl | | 58 | amorphous |
| 103 | —(CH₂)₅CH₃ | OCH₃ | 82 | 124–125 |
| 104 | —(CH₂)₆CH₃ | | 90 | 138–139 |
| 105 | —(CH₂)₇CH₃ | | 82 | 104–106 |
| 106 | —(CH₂)₈CH₃ | | 74 | 84–86 |
| 107 | —(CH₂)₉CH₃ | | 81 | 94–96 |
| 108 | 2-methoxyphenyl | | 100 | 196–197 |
| 109 | 3-methoxyphenyl | | 98 | amorphous |
| 110 | 4-methoxyphenyl | | 100 | 201–202 |
| 111 | 2-chlorophenyl | | 100 | 201–202 |
| 112 | 3-chlorophenyl | OCH₃ | 100 | 186–187 |
| 113 | 4-chlorophenyl | | 88 | 218–221 |
| 114 | 2-nitrophenyl | | 100 | 218–220 |
| 115 | 3-nitrophenyl | | 95 | 240–242 |
| 116 | 4-nitrophenyl | | 60 | 210–212 |
| 117 | 3,4-methylenedioxyphenyl | | 71 | 260 dec. (hydrochloride) |
| 118 | 2-methoxybenzyl | | 97 | amorphous |
| 119 | 3-methoxybenzyl | | 64 | 150–152 |
| 120 | 4-methoxybenzyl | | 67 | 165–167 |
| 121 | 2-chlorobenzyl | | 100 | 173–174 |
| 122 | 3-chlorobenzyl | | 80 | 172–173 |
| 123 | 4-chlorobenzyl | | 100 | 179–180 |
| 124 | 2-nitrobenzyl | | 93 | 215–218 |
| 125 | 3-nitrobenzyl | | 89 | 195–196.5 |
| 126 | 4-nitrobenzyl | | 100 | 198–199 |
| 127 | —(CH₂)₆CH₃ | Cl | 62 | 135–136 |
| 128 | —(CH₂)₇CH₃ | | 52 | 225–228 |
| 129 | —(CH₂)₈CH₃ | | 56 | 230–233 |
| 130 | 3,4-methylenedioxyphenyl | | 41 | 250 dec. (hydrochloride) |
| 131 | 4-methoxybenzyl | | 60 | 193–195 |
| 132 | 4-chlorobenzyl | | 60 | 188–192 |
| 133 | 4-nitrobenzyl | | 26 | 233 dec. |

TABLE 4

Structure: piperidine with N-COR¹ substituent, 4-position connected to dihydropyrimidine (with R³ substituent and 2-NH₂)

| Example No | R¹ | R³ | Yield (%) | M.P. (°C.) |
|---|---|---|---|---|
| 134 | Cyclohexyl | Ph | 88 | amorphous |
| 135 | Cyclohexylmethyl | | 76 | amorphous |
| 136 | —(CH₂)₆CH₃ | | 89 | 112–113 |
| 137 | —(CH₂)₇CH₃ | | 100 | 140–141 (hydrochloride) |
| 138 | —(CH₂)₈CH₃ | | 100 | amorphous |
| 139 | 2-furyl | | 77 | 122–123 |
| 140 | 3,4-methylenedioxyphenyl | | 77 | 201–202 |
| 141 | Benzyl | | 74 | 141–142 |
| 142 | 4-methoxybenzyl | | 100 | amorphous |
| 143 | 4-chlorobenzyl | | 100 | 157–158 |
| 144 | 4-nitrobenzyl | | 100 | amorphous |
| 145 | 3,4-methylenedioxybenzyl | | 68 | amorphous |
| 146 | 3,4,5-trimethoxybenzyl | | 48 | 98–100 |
| 147 | —(CH₂)₆CH₃ | 4-chloro-phenyl | 93 | 118–120 |
| 148 | —(CH₂)₇CH₃ | | 92 | 97–98 |
| 149 | —(CH₂)₈CH₃ | | 94 | 108–109 |
| 150 | 3,4-methylenedioxyphenyl | | 84 | 103–106 |
| 151 | 4-methoxybenzyl | 4-chloro-phenyl | 99 | 178.5–180 |
| 152 | 4-chlorobenzyl | | 89 | 183–184 |
| 153 | 4-nitrobenzyl | | 94 | 200–202 |
| 154 | —(CH₂)₆CH₃ | 4-methoxy-phenyl | 93 | 118–120 |
| 155 | —(CH₂)₇CH₃ | | 92 | 97–98 |
| 156 | —(CH₂)₈CH₃ | | 94 | 108–109 |
| 157 | 3,4-methylenedioxyphenyl | | 84 | 103–106 |
| 158 | 4-methoxybenzyl | | 99 | 178.5–180 |
| 159 | 4-chlorobenzyl | | 89 | 183–184 |
| 160 | 4-nitrobenzyl | | 94 | 200–202 |
| 161 | Cyclohexyl | 4-methoxy-benzyl | 76 | 159–160 |
| 162 | —CH₃ | | 89 | 203–205 |
| 163 | —CH₂CH₃ | | 93 | 133–135 |
| 164 | —(CH₂)₂CH₃ | | 98 | 140–141 |
| 165 | —(CH₂)₃CH₃ | | 94 | 100–103 |
| 166 | —(CH₂)₄CH₃ | | 100 | 120–121 |
| 167 | —(CH₂)₅CH₃ | | 100 | 108–109 |
| 168 | —(CH₂)₆CH₃ | | 98 | 101–103 |
| 169 | —(CH₂)₇CH₃ | | 100 | 114–116 |
| 170 | —(CH₂)₈CH₃ | | 100 | 102–104 |
| 171 | —(CH₂)₉CH₃ | | 100 | 88–90 |
| 172 | i-Propyl | | 100 | 163–163.5 |
| 173 | t-Butyl | | 96 | 151–152 |
| 174 | —(CH₂)₂Cl | | 91 | 131–134 |
| 175 | —(CH₂)₂Br | | 96 | 90–91 |
| 176 | —(CH₂)₂NHBoc | 4-methoxy-benzyl | 100 | amorphous |
| 177 | —(CH₂)₂OH | | 59 | amorphous |
| 178 | 2-methoxyphenyl | | 100 | 161–162 |
| 179 | 3-methoxyphenyl | | 100 | 149–151 |
| 180 | 4-methoxyphenyl | | 100 | 169–170.5 |
| 181 | 2-chlorophenyl | | 100 | 170–171.5 |
| 182 | 3-chlorophenyl | | 100 | 141–142 |
| 183 | 4-chlorophenyl | | 100 | 188–189 |
| 184 | 2-nitrophenyl | | 100 | 161–162 |
| 185 | 3-nitrophenyl | | 100 | 153–155 (hydrochloride) |
| 186 | 4-nitrophenyl | | 100 | amorphous (hydrochloride) |
| 187 | 2-fluorophenyl | | 100 | 181–183 |
| 188 | 3-fluorophenyl | | 100 | 168–170.5 |
| 189 | 4-fluorophenyl | | 94 | 176–177 |
| 190 | 2-methylphenyl | | 99 | 147–148.5 |
| 191 | 3-methylphenyl | | 93 | 175–176 |

TABLE 4-continued

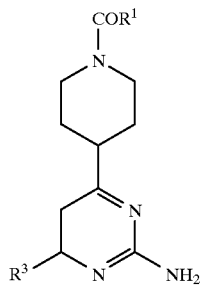

| Example No | R¹ | R³ | Yield (%) | M.P. (° C.) |
|---|---|---|---|---|
| 192 | 4-methylphenyl | | 99 | 183–184 |
| 193 | 2-furyl | | 83 | 124–125 |
| 194 | 2-pyridyl | | 81 | 157–158 |
| 195 | 3-pyridyl | | 45 | 153.5–154.5 |
| 196 | 4-pyridyl | | 100 | 148–150 |
| 197 | 2,3-dimethoxyphenyl | | 86 | 147–148 |
| 198 | 2,4-dimethoxyphenyl | | 39 | 194–196 |
| 199 | 2,5-dimethoxyphenyl | | 59 | 135–136 |
| 200 | 2,6-dimethoxyphenyl | | 100 | 144–145 |
| 201 | 3,4-dimethoxyphenyl | 4-methoxybenzyl | 99 | 159–160 |
| 202 | 3,5-dimethoxyphenyl | | 100 | 198–200 |
| 203 | 2,3-dichlorophenyl | | 100 | 157–158 |
| 204 | 2,4-dichlorophenyl | | 100 | 147–148 |
| 205 | 2,5-dichlorophenyl | | 100 | 155–156 |
| 206 | 2,6-dichlorophenyl | | 85 | 178–179 |
| 207 | 3,4-dichlorophenyl | | 98 | 195–196 |
| 208 | 3,5-dichlorophenyl | | 100 | 154–155 |
| 209 | 2,4-dinitrophenyl | | 89 | 116–119 |
| 210 | 3,4-methylenedioxyphenyl | | 96 | 170–171 |
| 211 | 1-naphtyl | | 78 | 161–162 |
| 212 | 2-naphtyl | | 79 | 220–221.5 |
| 213 | 2,3,4-trimethoxyphenyl | | 50 | 123–125 |
| 214 | 2,3,6-trimethoxyphenyl | | 90 | amorphous |
| 215 | 2,4,5-trimethoxyphenyl | | 35 | 189–190 |
| 216 | 2,4,6-trimethoxyphenyl | | 73 | amorphous |
| 217 | 3,4,5-trimethoxyphenyl | | 94 | amorphous |
| 218 | 2,3,5-trichlorophenyl | | 100 | 189–190 |
| 219 | 2,3,6-trichlorophenyl | | 89 | amorphous |
| 220 | 2,4,6-trichlorophenyl | | 100 | 159–160 |
| 221 | Benzyl | | 68 | 140–140.5 |
| 222 | 2-methoxybenzyl | | 96 | 134–136 |
| 223 | 3-methoxybenzyl | | 57 | 179–180 |
| 224 | 4-methoxybenzyl | | 100 | 129–130 |
| 225 | 2-chlorobenzyl | | 100 | 190–193 |
| 226 | 3-chlorobenzyl | 4-methoxybenzyl | 97 | 178–181 |
| 227 | 4-chlorobenzyl | | 92 | 158–159.5 |
| 228 | 2-flurobenzyl | | 100 | 170–171 |
| 229 | 3-fluorobenzyl | | 100 | 156–158.5 |
| 230 | 4-fluorobenzyl | | 99 | 159–160 |
| 231 | 2-nitrobenzyl | | 100 | 198–200 |
| 232 | 3-nitrobenzyl | | 100 | 162–164 |
| 233 | 4-nitrobenzyl | | 94 | 149–150 |
| 234 | 2-pyridylmethyl | | 74 | 131–132 |
| 235 | 3-pyridylmethyl | | 48 | 109–112 |
| 236 | 2,5-dimethoxybenzyl | | 97 | 130–132 |
| 237 | 3,4-dimethoxybenzyl | | 100 | amorphous |
| 238 | 3,5-dimethoxybenzyl | | 91 | amorphous |
| 239 | 2,4-dichlorobenzyl | | 100 | 182–184 |
| 240 | 2,6-dichlorobenzyl | | 99 | amorphous |
| 241 | 3,4-dichlorobenzyl | | 93 | 150–151 |
| 242 | 2,4-dinitrobenzyl | | 96 | 131–132 |
| 243 | 3,4-methylenedioxybenzyl | | 86 | 155–156 |
| 244 | 2,3,6-trichlorobenzyl | | 100 | amorphous |
| 245 | 3,4,5-trimethoxybenzyl | | 96 | amorphous |
| 246 | 2-(3,4-methylenedioxyphenyl)ethyl | | 71 | 123–125 |
| 288 | 1,3-benzodioxol-4-yl | | 82 | 167–167.5 |
| 289 | 5-benzimidazolyl | | 81 | amorphous |
| 290 | 5-indolyl | | 93 | amorphous |
| 291 | 1,4-benzodioxan-6-yl | | 92 | 187–188 |
| 292 | 3,4-difluorophenyl | | 69 | 159–160 |
| 293 | 5-benzo[b]furyl | | 77 | 188–188.5 |
| 294 | 6-benzo[b]furyl | | 88 | 186–187 |
| 295 | 4-benzo[b]furyl | | 90 | 173–174 |
| 296 | 2,3-dihydrobenzo[b]furan-5-yl | | 98 | 162–164 |
| 297 | 5-benzoxazolyl | | 88 | 178–179 |
| 298 | 6-benzoxazolyl | | 83 | 185–186 |
| 299 | 6-benzothiazolyl | | 75 | 153–154 |
| 300 | 4-hydroxy-3-methoxyphenyl | | 88 | 131–135 (hydrochloride) |
| 301 | 3-hydroxy-4-methoxyphenyl | | 96 | amorphous (hydrochloride) |
| 247 | —(CH₂)₆CH₃ | 4-chlorobenzyl | 70 | 142–143 |
| 248 | —(CH₂)₇CH₃ | | 79 | 137.5–138.5 |
| 249 | —(CH₂)₈CH₃ | | 70 | 136–137 |
| 250 | 3,4-methylenedioxyphenyl | | 85 | 162–163 |
| 251 | 4-methoxybenzyl | | 82 | 132–133 |
| 252 | 4-chlorobenzyl | | 77 | 163–164 |
| 253 | 3,4-methylenedioxybenzyl | | 89 | 203–204 |
| 254 | Cyclohexyl | 2-phenylethyl | 78 | 120–121 |
| 255 | —(CH₂)₆CH₃ | | 99 | 83–84 |
| 256 | —(CH₂)₇CH₃ | | 94 | 72–73 |
| 257 | —(CH₂)₈CH₃ | | 92 | 77–78 |
| 258 | 2-furyl | | 84 | 109–110 |
| 259 | 3,4-methylenedioxyphenyl | | 85 | 158–158.5 |
| 260 | Benzyl | | 47 | amorphous |
| 261 | 4-methoxybenzyl | | 81 | 135–136 |
| 262 | 4-chlorobenzyl | | 80 | 144–145.5 |
| 263 | 4-nitrobenzyl | | 91 | 169–170 |

TABLE 5

| Example No. | R¹ | Yield (%) | M.P. (° C.) |
|---|---|---|---|
| 264 | Cyclohexyl | 74 | 225–226 |
| 265 | 2-furyl | 82 | 236–237 |
| 266 | 3,4-methylenedioxyphenyl | 97 | 220–222 |
| 267 | Benzyl | 61 | 196–197 |

EXAMPLE 268–277

The urethane and sulfonamide derivatives in Tables 6 and 7 were prepared by a procedure similar to that described in Example 12, treating various chloroformates or sulfonyl chlorides instead of acid chlorides with piperidyl derivatives, i.e., 2-amino-4-(4-piperidinyl)quinazoline and 2-amino-4-(4-methoxyphenylmethyl)-6-(4-piperidinyl)pyrimidine.

TABLE 6

[Structure: X¹—R¹ attached to N of piperidine, connected to 4-position of 2-aminoquinazoline]

| Example No. | $X^2$ | $R^1$ | Yield (%) | M.P. (° C.) |
|---|---|---|---|---|
| 268 | —(CO)O— | -Ph | 93 | amorphous |
| 269 | | —CH₂Ph | 90 | 148–150 |
| 270 | —SO₂— | —(CH₂)₇CH₃ | 57 | 144–145 |
| 271 | | -Ph | 89 | 212–214 |
| 272 | | —CH₂Ph | 48 | 234–235 |

TABLE 7

[Structure: X²—R¹ attached to N of piperidine, connected to 4-position of 2-amino-6-(4-methoxybenzyl)pyrimidine]

| Example No. | $X^2$ | $R^1$ | Yield (%) | M.P. (° C.) |
|---|---|---|---|---|
| 273 | —(CO)O— | -Ph | 72 | 164–166 |
| 274 | | —CH₂Ph | 61 | 160–161 |
| 275 | —SO₂— | —(CH₂)₇CH₃ | 55 | 135–136 |
| 276 | | -Ph | 84 | 156–157.5 |
| 277 | | —CH₂Ph | 60 | 177–178 |

EXAMPLE 278

Synthesis of 2-amino-4-(1-phenylcarbamoyl-4-piperidinyl)quinazoline

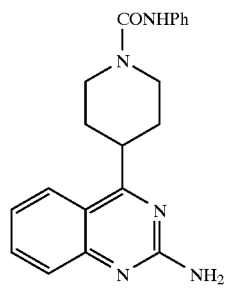

To a solution of 2-amino-4-(4-piperidinyl)quinazoline (100 mg, 0.44 mmol) obtained in Example 11(1) and tri-ethylamine (133 mg, 1.3 mmol) in dichloromethane (50 ml) was added phenyl isocyanate (50 mg, 0.42 mmol) under a nitrogen atmosphere. The mixture was stirred for about 3 hours at room temperature. The reaction mixture was washed with saturated sodium hydrogencarbonate aqueous solution. The organic layer was dried over sodium sulfate and evaporated in vacuo. The residue was purified by silicagel column chromatography (chloroform:methanol=99:1) to give the titled compound (127 mg).

Melting point: 178–180° C.

EXAMPLE 279

Synthesis of 2-amino-4-(1-octylcarbamoyl-4-piperidinyl)quinazoline

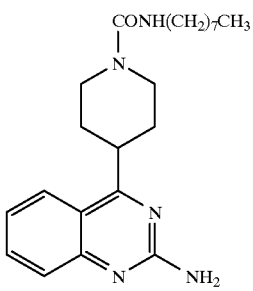

By a procedure similar to that described in Example 278, the titled compound (122 mg) was prepared from 2-amino-4-(4-piperidinyl)quinazoline (100 mg, 0.44 mmol) obtained in Example 11(1).

Melting point: 85–87° C.

EXAMPLE 280

Synthesis of 2-amino-4-(1-benzyl-carbamoyl-4-piperidinyl)quinazoline

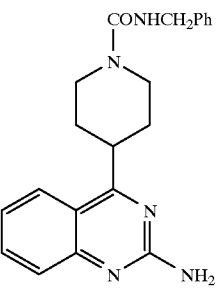

By a procedure similar to that described in Example 278, the titled compound (132 mg) was prepared from of 2-amino-4-(4-piperidinyl)quinazoline (100 mg, 0.44 mmol) obtained in Example 11(1).

Melting point: 217–218° C.

EXAMPLE 281

Synthesis of 2-amino-4-(4-methoxyphenylmethyl)-6-(1-phenylcarbamoyl-4-piperidinyl)pyrimidine

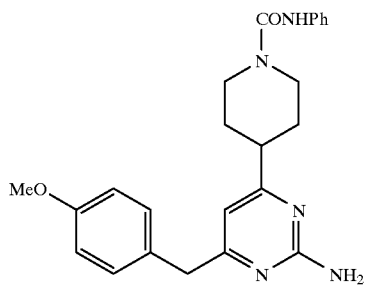

By a procedure similar to that described in Example 278, the titled compound (108 mg) was prepared from 2-amino-4-(4-methoxyphenylmethyl)-6-(4-piperidinyl)pyrimidine (100 mg, 0.34 mmol).

Melting point: 178–180° C.

EXAMPLE 282

Synthesis of 2-amino-4-(4-methoxyphenylmethyl)-6-(1-octylcarbamoyl-4-piperidinyl)pyrimidine

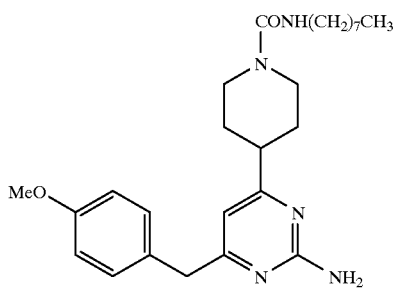

By a procedure similar to that described in Example 278, the titled compound (120 mg) was prepared from of 2-amino-4-(4-methoxyphenylmethyl)-6-(4-piperidinyl)pyrimidine(100 mg, 0.34 mmol).

Melting point: 104–106° C.

EXAMPLE 283

Synthesis of 2-amino-4-(1-benzylcarbamoyl-4-piperidinyl)-6-(4-methoxyphenylmethyl)pyrimidine

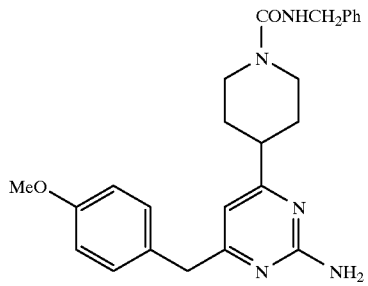

By a procedure similar to that described in Example 278, the titled compound (119 mg) was prepared from of 2-amino-4-(4-methoxyphenylmethyl)-6-(4-piperidinyl)pyrimidine (100 mg, 0.34 mmol).

Melting point: 128–131° C.

EXAMPLE 284

Synthesis of 2-amino-4-[1-(7-aminoheptanoyl)-4-piperidinyl]quinazoline

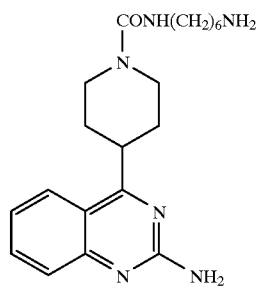

To a solution of 2-amino-4-[1-(7-t-butoxycarbonylaminoheptanoyl)-4-piperidinyl]quinazoline (160 mg) obtained in Example 27 in tetrahydrofuran (1 ml) was added 4N hydrogen chloride-dioxane solution (1 ml). The reaction mixture was stirred for about 1 hour at room temperature and was evaporated. The residue was triturated with diethyl ether to give the title compound (131 mg) as hydrochloride.

Melting point: 230–233° C.

EXAMPLE 285

Synthesis of 2-amino-4-[1-(8-aminooctanoyl)-4-piperidinyl]quinazoline

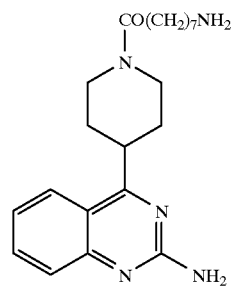

By a procedure similar to that described in Example 284, the titled compound (91 mg) as hydrochloride was prepared from 2-amino-4-[1-(8-t-butoxycarbonylaminooctanoyl)-4-piperidinyl]quinazoline (100 mg) obtained in Example 28.

Melting point: 222–224° C.

EXAMPLE 286

Synthesis of 2-amino-4-[1-(11-aminoundecanoyl)-4-piperidinyl]quinazoline

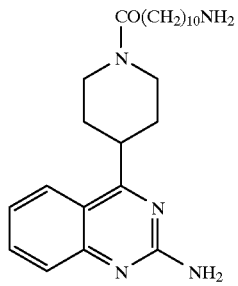

By a procedure similar to that described in Example 284, the titled compound (130 mg) as hydrochloride was prepared from 2-amino-4-[1-(11-t-butoxycarbonyl-aminoundecanoyl)-4-piperidinyl]quinazoline (170 mg) obtained in Example 29.

Melting point: 163–165° C.

EXAMPLE 287

Synthesis of 2-amino-4-[1-(3-aminopropanoyl)-4-piperidinyl]-6-(4-methoxyphenylmethyl)pyrimidine

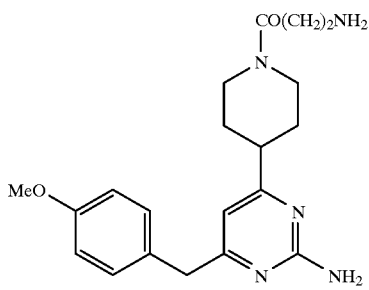

By a procedure similar to that described in Example 284, the titled compound (127 mg) as hydrochloride was prepared from 2-amino-4-[1-(3-t-butoxycarbonylamino-propanoyl)-4-piperidinyl]-6-(4-methoxyphenylmethyl) pyrimidine (170 mg) obtained in Example 176.

Melting point: amorphous

EXAMPLE 302

Synthesis of 2-amino-4-[1-(3,4-dihydroxybenzoyl)-4-piperidinyl]-6-(4-methoxyphenylmethyl) pyrimidine (1) 2-Amino-4-[1-(3,4-dibenzyloxybenzoyl)-4-piperidinyl]-6-(4-methoxyphenylmethyl) pyrimidine

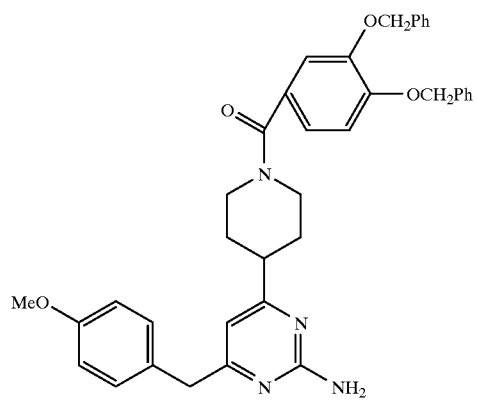

To a solution of 2-amino-4-(4-methoxyphenylmethyl)-6-(4-piperidinyl)pyrimidine (160 mg, 0.54 mmol), 3,4-dibenzyloxybenzoic acid (179 mg, 0.54 mmol) and 1-hydroxybenzotriazole (72 mg, 0.54 mmol) in dichloromethane (150 ml) were added 1-ethyl-3-(N, N'-dimethylaminopropyl)carbodiimide hydrochloride (103 mg, 0.54 mmol) at room temperature under nitrogen atmosphere. After stirring for about 30 minutes, the mixture was washed successively with saturated sodium hydrogen carbonate solution and brine. The organic layer was dried over anhydrous sodium sulfate and then evaporated. The residue was purified by column chromatography (chloroform:methanol=99:1) to give the titled compound (477 mg).

$^1$H-NMR (CDCl$_3$): δ 1.77 (4H, m), 2.59 (1H, m), 2.84 (2H, m), 3.78 (3H, s), 3.82 (2H, s), 3.90 (1H, m), 4.70 (1H, m), 5.11 (2H, s), 5.17 (2H, s), 5.18 (2H,s), 6.24 (1H, s), 6.84–7.00 (5H, m), 7.14–7.44 (12H, m).

(2) 2-Amino-4-[1-(3,4-dihydroxybenzoyl)-4-piperidinyl]-6-(4-methoxyphenylmethyl) pyrimidine

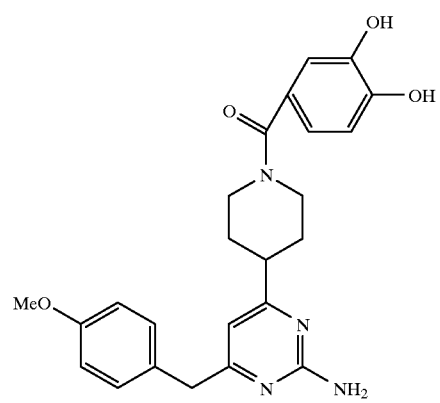

2-Amino-4-[1-(3,4-dibenzyloxybenzoyl)-4-piperidinyl]-6-(4-methoxyphenylmethyl)pyrimidine (293 mg, 0.48 mmol) was dissolved in a mixture of methanol (3 ml) and ethyl acetate (3 ml), and hydrogenated under 1 atm in the presence of 10% palladium on carbon (80 mg) for about 3 hours. The catalyst was filtered off and washed with methanol. The filtrate was concentrated in vacuo and the residue was purified by column chromatography (chloroform:methanol=97:3) to give the titled compound (155 mg).

$^1$H-NMR (CDCl$_3$): δ 1.74 (4H, m), 2.62 (1H, m), 2.87 (2H, m), 3.77 (3H, s), 3.82 (2H, s), 3.87 (1H, m), 4.65 (1H, m), 5.35 (2H, s), 6.25 (1H, s), 6.79 (5H, m), 7.14 (2H, d, J=8.6), 7.26 (2H, s).

EXAMPLE 303

Synthesis of 2-amino-4-(4-bromophenylmethyl)-6-[1-(3,4-methylenedioxybenzoyl)-4-piperidinyl] pyrimidine (1) 1-(3,4-Methylenedioxybenzoyl)isonipecotic acid

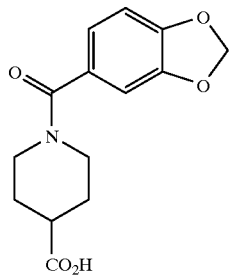

To an ice cold solution of isonipecotic acid (119.77 g, 0.927 mol) and potassium carbonate (256.32 g, 1.855mol) in water (900 ml) was added dropwise piperonyloyl chloride (155.6 g, 0.843 mol) in tetrahydrofuran (900 mol) with vigorous stirring over about 2 hours. The reaction temperature was kept below about 10° C. during the addition and the mixture was then stirred for about 30 minutes. The reaction mixture was acidified with conc. hydrochloric acid and extracted with chloroform. The organic layer was washed with water and dried over anhydrous magnesium sulfate, then evaporated. The residue was crystallized from methanol to give the titled compound (210.81 g)

$^1$H-NMR (CDCl$_3$): δ 1.49(2H, m), 1.81(2H, m), 2.51(1H, m), 2.99(2H, m), 3.98(2H, m), 6.07(2H, s), 6.88(1H, dd, J=1.3, J=7.9), 6.95(2H, m), 12.29(1H, s).

(2) Ethyl 3-[1-(3,4-methylenedioxybenzoyl)-4-piperidinyl)]-3-oxopropionate

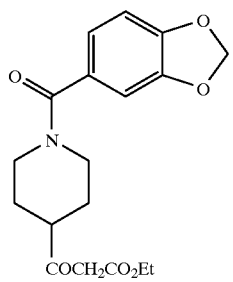

To a THF solution(2 L) of 1-(3,4-methylenedioxybenzoyl)isonipecotic acid (110 g, 0.397 mol) was added carbonyldiimidazole (70.8 g, 0.437 mol) in several portions at room temperature under nitrogen atmosphere. After stirring for about 3.5 hours, magnesium ethyl malonate (125.12 g, 0.437 mol) was added and refluxed for about 3 hours. The solvent was removed under reduced pressure. The residue was partitioned between ethyl acetate (3 L) and saturated sodium hydrogen carbonate (1.5 L). The organic layer was washed with brine twice and dried over anhydrous magnesium sulfate, then evaporated. The residue was purified by column chromatography (hexane:ethyl acetate=1:1) to give the titled compound as colorless oil (132.40 g).

Magnesium ethyl malonate was prepared as follows: To a stirred THF solution (1 L) of monoethyl malonate (183.18 g, 1.39 mol) was added magnesium ethoxide (79.54 g, 0.70 mol) in several portions. After about 4 hours, the solvent was removed under reduced pressure and the residue was reevaporated with toluene to give magnesium ethyl malonate (190.82 g).

(3) 4-{1-[4-(4-Bromophenyl)-1,3-dioxobutyl]}-1-(3,4-methylenedioxybenzoyl) piperidine

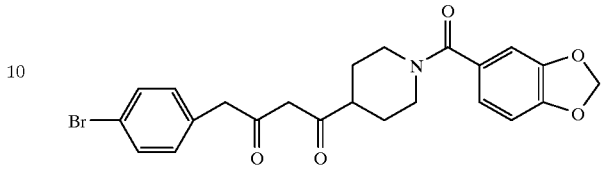

To an ice cooled solution of ethyl 3-[1-(3,4-methylenedioxybenzoyl)-4-piperidinyl) ]-3-oxo-propionate (7 g, 20 mmol) in tetrahydrofuran (35 ml) was added sodium hydride (60% oil dispersion, 1.68 g, 42 mmol) in several portions under nitrogen atmosphere. The reaction temperature was kept below about 5° C. during addition and To the mixture 4-bromophenylacetyl chloride (5.18 g, 0.22 mmol) in tetrahydrofuran (15 ml) was added dropwise over about one hour at about 5° C. After stirring about further 30 minutes, the mixture was acidified by 4N-hydrochloric acid and was extracted with ethyl acetate. The organic layer was washed with water and dried over anhydrous sodium sulfate, then evaporated to give a diketoester as a crude oil. The diketoester was used following reaction without further purification. The mixture of diketoester, water (1.6 ml) and dimethylsulfoxide (18 ml) was heated at about 1° C. for about 7.5 hours. The mixture was poured into water and extracted with ethyl acetate. The organic layer was washed with water and dried over anhydrous sodium sulfate, then evaporated. The residue was purified by flash column chromatography (hexane:ethyl acetate=1:1) to give the titled compound (5.54 g) as an oil.

$^1$H-NMR (CDCl$_3$): δ 1.63(2H, m), 1.81(2H, m), 2.42(1H, m), 2.91(2H, m,), 3.57(2H, s), 3.9–4.9(2H,m), 5.43(1H, s), 6.00(2H, s), 6.86(3H, m), 7.10(2H, d, J=8.6), 7.47(2H, d, J=8.6), 15.37(1H, s).

(4) 2-Amino-4-(4-bromophenylmethyl)-6-[1-(3,4-methylenedioxybenzoyl)-4-piperidinyl]pyrimidine

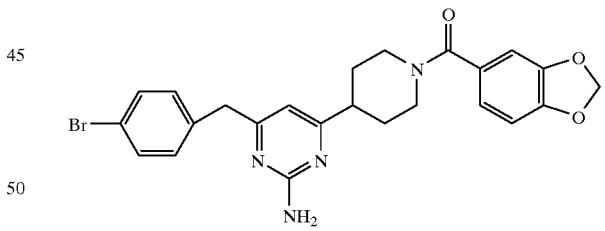

A mixture of 4-{1-[4-(4-bromophenyl)-1,3-dioxobutyl]}-1-(3,4-methylenedioxybenzoyl) piperidine (5.3 g, 11.2 mmol), guanidine carbonate (2.02 g, 11.2 mmol) and pyridine (25 ml) was heated at about 110° C. for about 8 hours. The mixture was evaporated in vacuo and the residue was partitioned between chloroform and saturated sodium hydrogen carbonate aqueous solution. The organic layer was washed with brine and dried over anhydrous sodium sulfate, then evaporated. Crystallization from ethanol gave the titled compound (3.88 g).

Melting point: 162–162.5° C. $^1$H-NMR (CDCl$_3$): δ 1.65–1.84(4H, m), 2.66(1H, m), 2.92(2H, m), 3.83(2H, s), 4–4.8(2H,m), 4.96(2H, s), 6.00(2H, s), 6.26(1H, s), 6.82(1H, d, J=8.3), 6.93(2H, m), 7.12(2H, d, J=8.6), 7.44(2H, d, J=8.25).

The free amine (300 mg) was dissolved in chloroform and treated with 1N hydrogen chloride-diethyl ether solution (1 ml). The solvent was removed in vacuo. The residue was dissolved in small amount of isopropanol and triturated with ether to give the hydrochloride (300 mg) of the titled compound.

EXAMPLE 304–314

The amide compounds shown in Table 8 were prepared by a similar method described in Example 303 using a reaction of ethyl 3-[1-(3,4-methylenedioxybenzoyl)-4-piperidinyl)]-3-oxo-propionate with various carboxylic acids.

TABLE 8

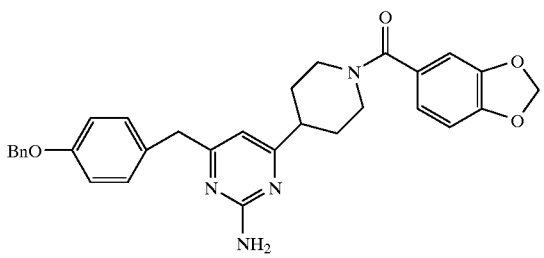

| Example No. | $R^6$ | Yield (%) | M.P. (° C.) |
| --- | --- | --- | --- |
| 304 | Benzyl | 39 | 115–118 (hydrochloride) |
| 305 | 3-methoxybenzyl | 68 | amorphous (hydrochloride) |
| 306 | 3,4-dimethoxybenzyl | 55 | 150–151 |
| 307 | 2,5-dimethoxybenzyl | 60 | 150–152 |
| 308 | 3,5-dimethoxybenzyl | 52 | 146–149 (hydrochloride) |
| 309 | 3,4,5-trimethoxybenzyl | 26 | 154–155 |
| 310 | 2-chlorobenzyl | 21 | amorphous (hydrochloride) |
| 311 | 3,4-dichlorobenzyl | 31 | 169–170 |
| 312 | 2,4-dichlorobenzyl | 32 | 205–206 |
| 313 | 2,6-dichlorobenzyl | 35 | 213–214 |
| 314 | 3,4-methylenedioxybenzyl | 58 | amorphous (hydrochloride) |

EXAMPLE 315

Synthesis of 2-amino-4-(4-hydroxyphenylmethyl)-6-[1-(3,4-methylenedioxybenzoyl)-4-piperidinyl] pyrimidine (1) 2-Amino-4-(4-benzyloxyphenylmethyl)-6-[1-(3,4-methylenedioxybenzoyl)-4-piperidinyl] pyrimidine

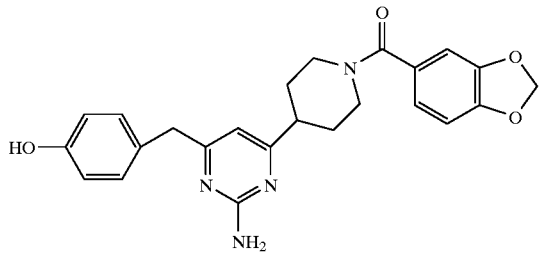

According to similar procedures described in Example 303 (3) and (4), the titled compound (570 mg) was prepared by treating ethyl 3-[1-(3,4-methylenedioxybenzoyl)-4-piperidinyl)]-3-oxopropionate(2.0 g) with 4-benzyloxyphenylacetyl chloride (1.66 g).

$^1$H-NMR (CDCl$_3$): δ 1.77 (4H, m), 2.65 (1H, m), 2.91 (2H, m), 3.83 (2H, s), 4–4.8 (2H, m), 4.93 (2H, s), 5.05 (2H, s), 5.99 (2H, s), 6.27 (1H, s), 6.81 (2H, d, J=8.1), 6.92 (3H, m), 7.15 (2H, d, J=8.6), 7.38 (5H, m).

(2) 2-Amino-4-(4-hydroxyphenylmethyl)-6-[1-(3,4-methylenedioxybenzoyl)-4-piperidinyl] pyrimidine

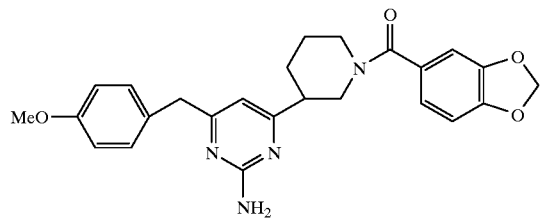

2-Amino-4-(4-benzyloxyphenylmethyl)-6-[1-(3,4-methylenedioxybenzoyl)-4-piperidinyl]pyrimidine (570 mg, 1.09 mmol) was dissolved in acetic acid (5 ml) and hydrogenated under 1 atm in the presence of 10% palladium on carbon (360 mg) for about 3.5 hours. The catalyst was filtered off. The filtrate was poured into aqueous sodium hydrogen carbonate and extracted with chloroform. The organic layer was concentrated in vacuo and the residue was purified by column chromatography (chloroform:methanol= 97:3) to give the titled compound (256 mg) as a foam.

$^1$H-NMR (CDCl$_3$): δ 1.85 (4H, m), 2.67 (1H m), 2.90 (2H, m), 3.80 (2H, s), 4.0–4.8 (2H, m), 5.10 (2H, s), 5.99 (2H, s), 6.30 (1H, s), 6.72 (2H, d, J=8.6), 6.81 (1H, d, J=8.3), 6.93 (2H, m), 7.02 (2H, d, J=8.6), 7.26 (1H, s).

The free amine (256 mg) was dissolved in chloroform and treated with 1N hydrogen chloride-diethyl ether solution (0.6 ml). The solvent was removed in vacuo. The residue was dissolved in small amount of isopropanol and triturated with ether to give the hydrochloride (240 mg) of the titled compound.

Melting point: 176–179° C.

EXAMPLE 316

Synthesis of 2-amino-4-(4-methoxyphenylmethyl)-6-[1-(3,4-methylenedioxybenzoyl)-3-piperidinyl] pyrimidine By a procedure similar to that described in Example 303, the titled compound (2.85 g, total yield of 44%) was prepared using nipecotic acid and 4-methoxyphenylacetyl chloride instead of isonipecotic acid and 4-bromophenylacetyl chloride respectively.

Melting Point:199–201° C. $^1$H-NMR (CDCl$_3$): δ 1.4–1.8 (3H, m), 1.97 (1H, m), 2.61 (1H, m), 2.97 (2H, m), 3.74 (1H, m), 3.80 (3H, s), 3.81 (2H, s), 4.6 (1H, m), 4.96 (2H, s), 5.99 (2H, s), 6.26 (1H, s), 6.85 (5H, m), 7.15 (2H, d, J=8.9).

EXAMPLE 317

Synthesis of 2-amino-4-(4-methoxyphenylmethyl)-6-[1-(3,4-methylenedioxybenzoyl)-3-piperidinyl] pyrimidine

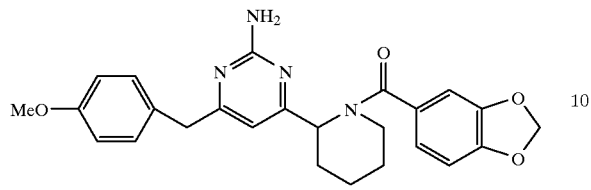

By a procedure similar to that described in Example 303, the titled compound (38 mg, total yield of 6%) was prepared using pipecolic acid and 4-methoxyphenylacetyl chloride instead of isonipecotic acid and 4-bromophenylacetyl chloride respectively.

Melting Point: 125–127° C. $^1$H-NMR (CDCl$_3$): δ 1.38–1.69 (5H, m), 2.53 (1H, m), 2.86 (1H, m), 3.6 (1H, m), 3.80 (3H, s), 3.86 (2H, s), 4.6 (0.5H, m, rotamer), 5.00 (2H, s), 5.68 (0.5H, m, rotamer), 5.98 (2H, s), 6.33 (1H, s), 6.76 (3H, m), 6.87 (2H, d, J=8.6), 7.16(2H, d, J=8.6).

EXAMPLE 318

Inhibitory activity of TNF α Production

BALB/c mice (female, 5–7 weeks old, Charles River Japan, Tokyo, Japan) were injected i.p. with 1 ml of 2.4% thioglycollate broth. After 4 days, the mice were sacrificed. Peritoneal exudated cells (PEC's) were collected from the peritoneal cavity by washing with minimum essential medium (MEM, Handai biseibutubyou kenkyukai, Osaka, Japan) containing 5 U/ml heparin, 1% fetal bovine serum (FBS, Filtron, Victoria, Australia) and antibiotics. The cells were washed two times with MEM, suspended with MEM containing 10% FBS (complete MEM, cMEM) and seeded into 96-well culture plates (Costar, Cambridge, Mass., USA) at 2×105 cells/well. The cells were incubated for 1 hour at 37° C. in a humidified 5% CO$_2$ incubator and washed two times to remove non-adherent cells.

TNF α was induced by 10 μg/ml of LPS (*E. coli* O111B4, DIFCO, Detroit, Mich., USA) the cells were cultured for 18 hours at 37° C. A compound of the present invention was dissolved in DMSO and added to the culture simultaneously with LPS. The final DMSO concentration was below 0.1%. The TNF α concentration in supernatant and recombinant mouse TNF α standard (rm-TNF α, Genzyme, Mass., USA) were incubated overnight at 4° C. in a 96-well plate coated with anti-mouse TNF α monoclonal antibody (PharMingen, San Diego, Calif., USA) that previously had been blocked with 10% FBS. Each well of the plate first was incubated at room temperature with biotinylated anti-mouse TNF α polyclonal antibodies (PharMingen) for 45 minutes, then with peroxidase-conjugated streptavidin (Kirkegaard & Perry Laboratories Inc., Gaitherburg, Md., USA) for 30 minutes. After each incubation, the plate was washed 4 to 8 times with PBS containing 0.2% Tween 20. TMB (Kirkegaard & Perry Laboratories Inc.) was the peroxidase substrate used and, the absorbance of each well was quantified at 450 nm by a microplatereader (Molecular Devices Corp., CA, USA). TNF α levels in the supernatant were quantified with rm-TNF α as the standard.

Inhibitory activity of TNF α production was also quantified using human peripheral blood mononuclear cells (PBMC) instead of PEC's. Results are shown in table 9, 10, 11, 12, 13, 14, 15, 16, 17, 18, 19 and 20.

TABLE 9

Inhibitory activity of compound on TNF α Production from mouse macrophages

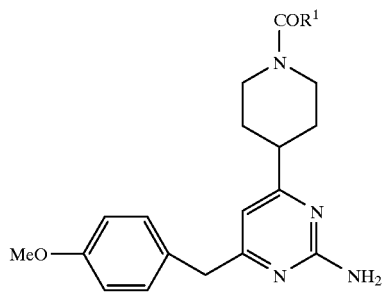

| Exp. No. | R$^1$ | % inhibition at 30 μM |
|---|---|---|
| 162 | —CH$_3$ | 61 |
| 163 | —CH$_2$CH$_3$ | 79 |
| 164 | —(CH$_2$)$_2$CH$_3$ | 43 |
| 165 | —(CH$_2$)$_3$CH$_3$ | 41 |
| 166 | —(CH$_2$)$_4$CH$_3$ | 48 |
| 167 | —(CH$_2$)$_5$CH$_3$ | 52 |
| 168 | —(CH$_2$)$_6$CH$_3$ | 49 |
| 169 | —(CH$_2$)$_7$CH$_3$ | 12 |
| 170 | —(CH$_2$)$_8$CH$_3$ | 11 |
| 171 | —(CH$_2$)$_9$CH$_3$ | 13 |
| 173 | t-Butyl | 31 |
| 174 | —(CH$_2$)$_2$Cl | 54 |
| 176 | —(CH$_2$)$_2$NHBoc | 60 |
| 287 | —(CH$_2$)$_2$NH$_2$ | 40 |
| 177 | —(CH$_2$)$_2$OH | 46 |
| 175 | —(CH$_2$)$_2$Br | 48 |
| 178 | 2-methoxyphenyl | 76 |
| 179 | 3-methoxyphenyl | 82 |
| 180 | 4-methoxyphenyl | 70 |
| 181 | 2-chlorophenyl | 26 |
| 182 | 3-chlorophenyl | 46 |
| 183 | 4-chlorophenyl | 54 |
| 184 | 2-nitrophenyl | 73 |
| 185 | 3-nitrophenyl | 69 |
| 186 | 4-nitrophenyl | 67 |
| 194 | 2-pyridyl | 9 |
| 195 | 3-pyridyl | 29 |
| 196 | 4-pyridyl | 57 |
| 197 | 2,3-dimethoxyphenyl | 29 |
| 198 | 2,4-dimethoxyphenyl | 29 |
| 201 | 3,4-dimethoxyphenyl | 46 |
| 204 | 2,4-dichlorophenyl | 84 |
| 205 | 2,5-dichlorophenyl | 51 |
| 207 | 3,4-dichlorophenyl | 76 |
| 211 | 1-naphthyl | 80 |
| 210 | 3,4-methylenedioxyphenyl | 75 |
| 213 | 2,3,4-trimethoxyphenyl | 43 |
| 214 | 2,3,6-trimethoxyphenyl | 13 |
| 217 | 3,4,5-trimethoxyphenyl | 44 |
| 218 | 2,3,5-trichlorophenyl | 55 |
| 219 | 2,3,6-trichlorophenyl | 75 |
| 220 | 2,4,6-trichlorophenyl | 75 |
| 222 | 2-methoxybenzyl | 36 |
| 223 | 3-methoxybenzyl | 82 |
| 224 | 4-methoxybenzyl | 73 |
| 225 | 2-chlorobenzyl | 43 |
| 226 | 3-chlorobenzyl | 69 |
| 227 | 4-chlorobenzyl | 63 |
| 233 | 4-nitrobenzyl | 54 |
| 237 | 3,4-dimethoxybenzyl | 87 |
| 238 | 3,5-dimethoxybenzyl | 96 |
| 239 | 2,4-dichlorobenzyl | 99 |
| 241 | 3,4-dichlorobenzyl | 95 |
| 243 | 3,4-methylenedioxybenzyl | 93 |
| 242 | 2,4-dinitrobenzyl | 31 |
| 244 | 2,3,6-trichlorobenzyl | 98 |
| 274 | —CO$_2$CH$_2$Ph | 49 |

TABLE 9-continued

Inhibitory activity of compound on TNF α Production from mouse macrophages

[Structure: 2-amino-4-(4-methoxybenzyl)-6-(1-COR¹-piperidin-4-yl)pyrimidine]

| Exp. No. | R¹ | % inhibition at 30 μM |
|---|---|---|
| 283 | —CONHCH₂Ph | 81 |
| 277 | —SO₂CH₂Ph | 32 |

TABLE 10

Inhibitory activity of compound on TNF α Production from mouse macrophages

[Structure: 2-amino-4-(4-chlorobenzyl)-6-(1-COR¹-piperidin-4-yl)pyrimidine]

| Exp. No. | R¹ | % inhibition at 30 μM |
|---|---|---|
| 247 | —(CH₂)₆CH₃ | 21 |
| 248 | —(CH₂)₇CH₃ | −6 |
| 249 | —(CH₂)₆CH₃ | −29 |
| 251 | 4-methoxybenzyl | 98 |
| 252 | 4-chlorobenzyl | 96 |
| 7 | Phenyl | 58 |
| 250 | 3,4-methylenedioxyphenyl | 91 |
| 253 | 3,4-methylenedioxybenzyl | 74 |

TABLE 11

Inhibitory activity of compound on TNF α Production from mouse macrophages

[Structure: 2-amino-4-(2-phenylethyl)-6-(1-COR¹-piperidin-4-yl)pyrimidine]

| Exp. No. | R¹ | % inhibition at 30 μM |
|---|---|---|
| 255 | —(CH₂)₆CH₃ | 47 |
| 256 | —(CH₂)₇CH₃ | 75 |
| 257 | —(CH₂)₈CH₃ | 90 |
| 261 | 4-methoxybenzyl | 42 |
| 262 | 4-chlorobenzyl | 43 |
| 263 | 4-nitrobenzyl | 37 |

TABLE 12

Inhibitory activity of compound on TNF α Production from mouse macrophages

[Structure: 2-amino-4-phenyl-6-(1-COR¹-piperidin-4-yl)pyrimidine]

| Exp. No. | R¹ | % inhibition at 30 μM |
|---|---|---|
| 136 | —(CH₂)₆CH₃ | 48 |
| 137 | —(CH₂)₇CH₃ | 67 |
| 138 | —(CH₂)₈CH₃ | 70 |
| 142 | 4-methoxybenzyl | 55 |
| 143 | 4-chlorobenzyl | 55 |
| 144 | 4-nitrobenzyl | 6 |
| 140 | 3,4-methylenedioxyphenyl | 72 |

TABLE 13

Inhibitory activity of compound on TNF α Production from mouse macrophages

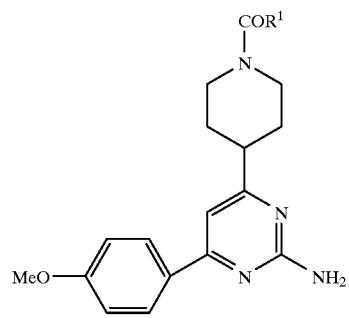

| Exp. No. | R[1] | % inhibition at 30 μM |
|---|---|---|
| 154 | —(CH$_2$)$_6$CH$_3$ | 86 |
| 155 | —(CH$_2$)$_7$CH$_3$ | 76 |
| 156 | —(CH$_2$)$_8$CH$_3$ | 74 |
| 158 | 4-methoxybenzyl | 61 |
| 159 | 4-chlorobenzyl | 75 |
| 160 | 4-nitrobenzyl | 57 |
| 157 | 3,4-methylenedioxyphenyl | 84 |
| 5 | Phenyl | 57 |

TABLE 14

Inhibitory activity of compound on TNF α Production from mouse macrophages

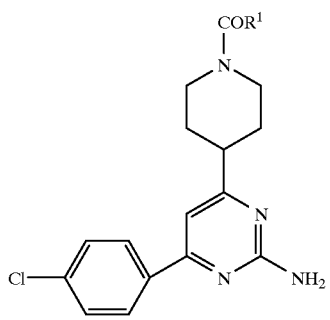

| Exp. No. | R[1] | % inhibition at 30 μM |
|---|---|---|
| 147 | (CH$_2$)$_6$CH$_3$ | 55 |
| 148 | —(CH$_2$)$_7$CH$_3$ | 68 |
| 149 | —(CH$_2$)$_8$CH$_3$ | 57 |
| 151 | 4-methoxybenzyl | 70 |
| 152 | 4-chlorobenzyl | 90 |
| 153 | 4-nitrobenzyl | 92 |
| 150 | 3,4-methylenedioxyphenyl | 100 |
| 6 | Phenyl | 78 |

TABLE 15

Inhibitory activity of compound on TNF α Production from mouse macrophages

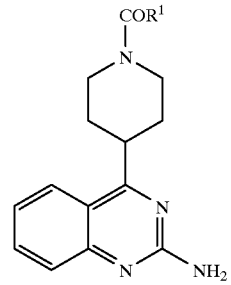

| Exp. No. | R[1] | % inhibition at 30 μM |
|---|---|---|
| 16 | —CH$_2$CH$_3$ | 4 |
| 17 | —(CH$_2$)$_2$CH$_3$ | 8 |
| 19 | —(CH$_2$)$_4$CH$_3$ | 10 |
| 20 | —(CH$_2$)$_5$CH$_3$ | 63 |
| 21 | —(CH$_2$)$_6$CH$_3$ | 74 |
| 22 | —(CH$_2$)$_7$CH$_3$ | 64 |
| 23 | —(CH$_2$)$_8$CH$_3$ | 67 |
| 24 | —(CH$_2$)$_9$CH$_3$ | 70 |
| 26 | t-Butyl | 19 |
| 30 | —(CH$_2$)$_9$OH | 64 |
| 284 | —(CH$_2$)$_6$NH$_2$ | 3 |
| 285 | —(CH$_2$)$_7$NH$_2$ | 27 |
| 286 | —(CH$_2$)$_{10}$NH$_2$ | 67 |
| 27 | —(CH$_2$)$_6$NHBoc | 95 |
| 28 | —(CH$_2$)$_7$NHBoc | 100 |
| 29 | —(CH$_2$)$_{10}$NHBoc | 100 |
| 32 | 2-methoxyphenyl | 30 |
| 33 | 3-methoxyphenyl | 18 |
| 35 | 2-chlorophenyl | 72 |
| 36 | 3-chlorophenyl | 42 |
| 37 | 4-chlorophenyl | 4 |
| 38 | 2-nitrophenyl | 30 |
| 39 | 3-nitrophenyl | 12 |
| 40 | 4-nitrophenyl | 15 |
| 50 | 3-pyridyl | 18 |
| 51 | 4-pyridyl | 28 |
| 52 | 2,3-dimethoxyphenyl | 20 |
| 53 | 2,4-dimethoxyphenyl | 54 |
| 56 | 3,4-dimethoxyphenyl | −28 |
| 59 | 2,4-dichlorophenyl | 56 |
| 60 | 2,5-dichlorophenyl | 73 |
| 62 | 3,4-dichlorophenyl | 55 |
| 66 | 1-naphthyl | 32 |
| 68 | 2,3,4-trimethoxyphenyl | 8 |
| 69 | 2,3,6-trimethoxyphenyl | −95 |
| 72 | 3,4,5-trimethoxyphenyl | 32 |
| 73 | 2,3,5-trichlorophenyl | 23 |
| 74 | 2,3,6-trichlorophenyl | 88 |
| 75 | 2,4,6-trichlorophenyl | 92 |
| 77 | 2-methoxybenzyl | 27 |
| 78 | 3-methoxybenzyl | 10 |
| 79 | 4-methoxybenzyl | −3 |
| 80 | 2-chlorobenzyl | 28 |
| 81 | 3-chlorobenzyl | 56 |
| 82 | 4-chlorobenzyl | 59 |
| 88 | 4-nitrobenzyl | 26 |
| 92 | 3,4-dimethoxybenzyl | 68 |
| 93 | 3,5-dimethoxybenzyl | 60 |
| 96 | 3,4-dichlorobenzyl | 100 |
| 94 | 2,4-dichlorobenzyl | 78 |
| 97 | 2,4-dinitrobenzyl | 45 |
| 98 | 2,3,6-trichlorobenzyl | 43 |
| 269 | —CO$_2$CH$_2$Ph | 77 |
| 280 | —CONHCH$_2$Ph | 34 |
| 272 | —SO$_2$CH$_2$Ph | 5 |

TABLE 16

Inhibitory activity of compound on TNF α Production from mouse macrophages

[Structure: 4-methoxyquinazolin-2-amine with piperidine-COR¹ substituent]

| Exp. No. | R¹ | % inhibition at 30 μM |
|---|---|---|
| 103 | —(CH₂)₅CH₃ | 44 |
| 104 | —(CH₂)₆CH₃ | 50 |
| 105 | —(CH₂)₇CH₃ | 54 |
| 106 | —(CH₂)₈CH₃ | 54 |
| 110 | 4-methoxyphenyl | 21 |
| 113 | 4-chlorophenyl | −1 |
| 116 | 4-nitrophenyl | 23 |
| 117 | 3,4-methylenedioxyphenyl | 54 |
| 120 | 4-methoxybenzyl | 31 |
| 123 | 4-chlorobenzyl | 28 |
| 126 | 4-nitrobenzyl | 43 |

TABLE 17

Inhibitory activity of compound on TNF α Production from mouse macrophages

[Structure: 6-chloroquinazolin-2-amine with piperidine-COR¹ substituent]

| Exp. No. | R¹ | % inhibition at 30 μM |
|---|---|---|
| 127 | —(CH₂)₆CH₃ | 48 |
| 128 | —(CH₂)₇CH₃ | 79 |
| 129 | —(CH₂)₈CH₃ | 48 |
| 130 | 3,4-methylenedioxyphenyl | 100 |
| 131 | 4-methoxybenzyl | 23 |
| 132 | 4-chlorobenzyl | 55 |
| 133 | 4-nitrobenzyl | 35 |

TABLE 18

Inhibitory activity of compound on TNF α production from PBMC

[Structure: pyrimidin-2-amine with R³ substituent and piperidine-benzodioxole carbonyl]

| Exp. No. | R³ | % inhibition at 30 μM |
|---|---|---|
| 210 | 4-methoxybenzyl | 80 |
| 140 | Ph | 35 |
| 150 | 4-chlorophenyl | 11 |
| 157 | 4-methoxyphenyl | 37 |
| 304 | Benzyl | 83 |
| 305 | 3-methoxybenzyl | 80 |
| 306 | 3,4-dimethoxybenzyl | 85 |
| 307 | 2,5-dimethoxybenzyl | 81 |
| 308 | 3,5-dimethoxybenzyl | 87 |
| 309 | 3,4,5-trimethoxybenzyl | 65 |
| 253 | 4-chlorobenzyl | 71 |
| 310 | 2-chlorobenzyl | 83 |
| 311 | 3,4-dichlorobenzyl | 69 |
| 312 | 2,4-dichlorobenzyl | 57 |
| 313 | 2,6-dichlorobenzyl | 91 |
| 314 | 3,4-methylenedioxybenzyl | 84 |
| 303 | 4-bromobenzyl | 92 |
| 315 | 4-hydroxybenzyl | 86 |
| 259 | —(CH₂)₂Ph | 68 |

TABLE 19

Inhibitory activity of compound on TNF α production from PBMC

[Structure: pyrimidin-2-amine with 4-methoxybenzyl and piperidine-COR¹]

| Exp. No. | R¹ | % inhibition at 30 μM |
|---|---|---|
| 289 | 5-benzoimidazolyl | 93 |
| 290 | 5-indolyl | 101 |
| 291 | 1,4-benzodioxan-6-yl | 88 |
| 292 | 3,4-difluorophenyl | 66 |
| 300 | 4-hydroxy-3-methoxyphenyl | 80 |
| 301 | 3-hydroxy-4-methoxyphenyl | 88 |
| 302 | 3,4-dihydroxybenzyl | 86 |

TABLE 20

Inhibitory activity of compound on TNF α production from PBMC

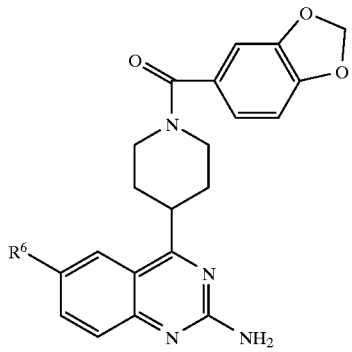

| Exp. No. | $R^6$ | % inhibition at 30 μM |
|---|---|---|
| 65 | H | 46 |
| 117 | $CH_3O$ | 43 |
| 130 | Cl | 57 |

EXAMPLE 319

Determination of the effect of a compound of the invention on HIV-1 LTR-driven CAT gene expression Materials and methods Plasmids:

p469, HIV-1 LTR driven CAT and pSV-Tat, Tat-expression vector were kindly provided from Dr. Gary J. Nabel (Nature Vol. 326, 711(1987))

Medium:

RPMI 1640 medium (Life Technologies, Grand Island, N.Y., USA) was supplemented with heat-inactivated fetal calf serum (FBS; Sigma, St. Louis, Mo., USA).

Cells:

Human T lymphoma cell line, Jurkat, was cultured in medium described above Transfection;

Introduction of plasmid DNA into cells was carried out according to the method described in Chiang, J. Li et al., Proc. Natl. Acad. Sci. Vol. 92, 5461–5464 (1995). Briefly, the cells were suspended with the medium at $2 \times 10^7$ cells/ml followed by addition 1 μg of p469 and 0.5 μg of DEAE-dextran (Sigma). In some experiments the cells were co-transfected with 0.5 μg of pSV-Tat. After 10 minutes incubation at room temperature with occasionally mixing, the cells were pulsed with electroporation apparatus at 140 V. The cells were re-suspended with the fresh medium and cultured for 20 hours at 37° C.

Determination of the effect of a compound of the invention on HIV-1 LTR-driven CAT gene expression.

A compound tested was dissolved in dimethylsulfoxide at 100 mM as a stock solution. The aliquots of the stock solution were kept frozen at −20° C. Jurkat cells transfected with p469 were treated with 10 ng/ml of phorbol 12-myristate 13-acetate (PMA; Sigma) to activate HIV-1-LTR directed CAT gene transcription in the presence of the compound. In the case of cells transfected with p469 and pSV-Tat, they were simply treated with the compound. After the cells were cultured for an additional 24 hours at 37° C., the cells were washed 2 times with phosphate-buffered saline and lysed in 50 mM Tris-HCl plus 15% glycerol with repeated cycles of freeze and thaw. The cell lysates were clarified by centrifugation followed by determination of protein concentration by Bradford method (Bio-Rad, Hercules, Calif., USA). Measurement of a CAT activity in cell lysates was carried out according to a similar method described in Fridovich-Keil J. L. et. al., Cell Growth and Differentiation, Vol. 2, 67–76(1991). Equal amount (30 μg of protein) of cell lysates was incubated at 37° C. with 35 μg of acetyl co-enzyme A (GIBCO/BRL, Grand Island, Mo., USA) and 0.1 μCi of 14C-chloramphenicol (Dupont, NEN Boston, Mass., USA) in 42 ml solution for 2 hours. Acetyl-14C-chloramphenicol was extracted with 9 volumes of ethyl acetate and fractionated on a TLC gel with 1:19 (v/v) in methanol/chloroform. The CAT activity was detected by autoradiography and quantified by an Imaging Densitometer (model GS-700; Bio-Rad). Results are shown in Table 21, 22 and 23.

TABLE 21

Inhibitory activity of compounds on PMA or Tat induced HIV-1 LTR-CAT gene expression in Jurkat cells

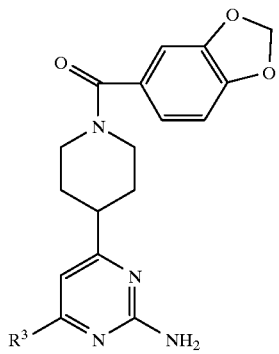

| Exp. No. | $R^3$ | % inhibition at 5 μM (PMA) | % inhibition at 5 μM (Tat) |
|---|---|---|---|
| 210 | 4-methoxybenzyl | 81 | 66 |
| 140 | Ph | 100 | NT |
| 150 | 4-chlorophenyl | 54 | NT |
| 157 | 4-methoxyphenyl | 81 | NT |
| 304 | benzyl | NT | 44 |
| 305 | 3-methoxybenzyl | NT | 72 |
| 306 | 3,4-dimethoxybenzyl | 75 | 22 |
| 307 | 2,5-dimethoxybenzyl | 97 | 66 |
| 308 | 3,5-dimethoxybenzyl | NT | 70 |
| 309 | 3,4,5-trimethoxybenzyl | NT | 62 |
| 253 | 4-chlorobenzyl | 72 | 65 |
| 310 | 2-chlorobenzyl | NT | 67 |
| 311 | 3,4-dichlorobenzyl | NT | 63 |
| 312 | 2,4-dichlorobenzyl | NT | 65 |
| 313 | 2,6-dichlorobenzyl | NT | 69 |
| 314 | 3,4-methylenedioxybenzyl | NT | 76 |
| 303 | 4-bromobenzyl | NT | 65 |
| 259 | $—(CH_2)_2Ph$ | 25 | 51 |

NT: not tested

TABLE 22

Inhibitory activity of compounds on PMA or Tat induced HIV-1 LTR-CAT gene expression in Jurkat cells

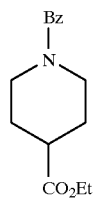

| Exp. No. | R⁶ | % inhibition at 5 μM (PMA) | % inhibition at 5 μM (Tat) |
|---|---|---|---|
| 65 | H | 94 | 81 |
| 117 | CH₃O | 92 | 36 |
| 130 | Cl | 67 | NT |

NT: not tested

TABLE 23

Inhibitory activity of compounds on PMA or Tat induced HIV-1 LTR-CAT gene expression in Jurkat cells

| Exp. No. | | % inhibition at 5 μM (MPA) | % inhibition at 5 μM (Tat) |
|---|---|---|---|
| 266 | 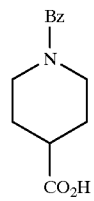 | 100 | NT |

NT: not tested

EXAMPLE 320

Formulation (1) Tablet

An active ingredient (100 mg), lactose (70 mg), corn starch (15 mg), low substituted hydroxypropylcellulose (8 mg), polyvinylpyrrolidone (6 mg) and magnesium stearate (1 mg) are mixed and are formulated to give a 200 mg of tablet.

An active ingredient (100 mg), D-mannitol (60 mg), crystalline cellulose (25 mg), carmellose calcium (8 mg), hydroxypropylmethylcellulose (6 mg), and magnesium striate (1 mg) are mixed and are formulated to give a 200 mg of tablet.

(2) Capsule

An active ingredient (100 mg), D-mannitol (110 mg), low substituted hydroxypropylcellulose (8 mg), and magnesium stearate (2 mg) are mixed and are filled into a capsule to give 220 mg of capsule formulation.

An active ingredient (100 mg), D-mannitol (43.5 mg), carmellose calcium (5 mg), and magnesium stearate (1.5 mg) are mixed and are filled into a capsule to give 150 mg of capsule formulation.

Reference Example 1

Synthesis of ethyl 1-benzoylisonipecotate

To an ice cold solution of ethyl isonipecotate (60 g, 0.382 mol) and triethylamine (38.65 g, 0.382 mol) in tetrahydrofuran (360 ml) was added dropwise benzoyl chloride (53.7 g, 0.382 mol) over a period of about 2 hours under nitrogen atmosphere. The reaction mixture was stirred for about 2 hours at the same temperature, and was filtered. The filtrate was evaporated in vacuo. The residue was partitioned between dichloromethane and water. The organic layer was dried over magnesium sulfate, and evaporated in vacuo. Crystallization from isopropyl alcohol gave the titled compound (90.9 g).

Melting point: 71–72° C. ¹H-NMR (CDCl₃): δ 1.27 (3H, t, J=7.3), 1.70 (4H, m), 2.57 (1H, m), 3.05 (2H, m), 3.75 (1H, m), 4.16 (2H, q, J=7.3), 4.54 (1H, m), 7.40 (5H, m)

Reference Example 2

Synthesis of 1-benzoylisonipecotic acid

To an ice cold solution of isonipecotic acid (90 g, 0.697 mol) and potassium carbonate (81 g, 1.31 mol) in water (1.3 liter) was added dropwise benzoyl chloride (81 ml, 0.697 mol) over a period of about an hour at about 5° C. The mixture was stirred at room temperature overnight. The reaction mixture was acidified with 6N hydrochloric acid and extracted with dichloromethane. The organic layer was washed with water and then dried over magnesium sulfate and the solvent was evaporated in vacuo. Crystallization from isopropyl alcohol-diethyl ether to give the titled compound (154.4 g).

Melting point: 143–144° C.

Reference Example 3

Synthesis of 4-cyanopiperidine

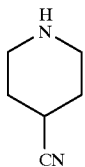

To vigorously stirred isonipecotamide (75 g, 0.585 mol) was added dropwise phosphorus oxychloride (182 ml) over a period of about 30 minutes. The reaction mixture was refluxed for about further 2 hours, the reaction mixture was evaporated in vacuo. The residue was poured onto ice (about 600 g) to decompose an excess of phosphorus oxychloride. The aqueous solution was neutralized with sodium hydrogencarbonate and then made basic with 2N sodium hydroxide. The aqueous layer was extracted 4 times with chloroform (500 ml each). The organic layer was dried over sodium sulfate, and evaporated in vacuo. The residue was distilled in vacuo (b.p. 70° C., 3 mmHg) to give the titled compound (50.9 g) as an oil.

The piperidinylpyrimidine derivatives of the present invention exhibit an excellent TNF α inhibiting activity and are useful as TNF α inhibitors. The piperidinylpyrimidine derivatives of the present invention not only will normalize the abnormal TNF α production indicating immunopathy caused by viral infection but also will inhibit the proliferation of HIV. And they also inhibited HIV-LTR transcriptional activation in vitro. Therefore, the piperidinylpyrimidine derivatives of the present invention are expected to be effective for the treatment of AIDS.

The piperidinylpyrimidine derivatives of the present invention are also expected to be useful for the treatment of diseases wherein a TNF α level reportedly is increased in blood and/or tissue, e.g., osteoarthritis, rheumatoid arthritis, multiple sclerosis, Kawasaki disease, inflammatory bowel diseases such as ulcerative colitis or Crohn's disease, Behçet disease, systemic lupus erythematosus, graft versus host disease (GvHD), multiple organ failure, malaria, meningitis, hepatitis, non-insulin-dependent diabetes mellitus, asthma, adult respiratory distress syndrome (ARDS), tuberculosis, atherosclerosis, Alzheimer's disease, etc.

We claim:

1. A method of inhibiting the production or secretion of tumor necrosis factor in a patient who has elevated levels of tumor necrosis factor, comprising administering to said patient a pharmaceutically effective amount of a compound of formula (1):

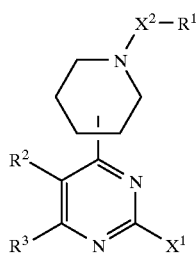

(1)

wherein $X^1$ is amino or hydroxy;

$X^2$ is carbonyl (—(CO)—), carbonyloxy (—(CO)O—), carbonylamino (—(CO)NH—) or sulfonyl (—(SO$_2$)—);

$R^1$ is:
(a) alkyl having 1 to 10 carbon atoms,
(b) cycloalkyl having a saturated carbocyclic ring containing 3 to 7 carbon atoms,
(c) aryl having up to 10 carbon atoms,
(d) aryl having up to 10 carbon atoms and one or more substituents selected from the group consisting of:
  (1) halogen,
  (2) alkyl having 1 to 10 carbon atoms,
  (3) alkoxy having 1 to 6 carbon atoms,
  (4) nitro,
  (5) cyano,
  (6) carboxy,
  (7) hydroxy,
  (8) amino,
  (9) trifluoromethyl,
  (10) alkylamino having 1 to 4 carbon atoms,
  (11) dialkylamino having 2 to 8 carbon atoms,
  (12) alkanoyl having 1 to 6 carbon atoms,
  (13) alkanoylamino having 1 to 6 carbon atoms,
  (14) sulfamoyl,
  (15) alkylaminosulfonyl, wherein the alkylamino thereof has 1 to 4 carbon atoms,
  (16) dialkylaminosulfonyl, wherein the dialkylamino thereof has 2 to 8 carbon atoms and
  (17) alkoxycarbonyl, wherein the alkoxy thereof has 1 to 6 carbon atoms, or
  (18) substituents which are combined to form methylenedioxy, ethylenedioxy or dihydroxyfuran,
(e) unsaturated aromatized monocyclic or bicyclic heterocycle comprising not more than 9 carbon atoms and 1 to 3 hetero atoms selected from the group consisting of nitrogen, oxygen and sulfur or
(f) —(CH$_2$)$_m$-A, wherein m is an integer selected from the group consisting of 1, 2, 3, 4, 5, 6, 7, 8, 9 and 10, and A is:
  (1) halogen,
  (2) cycloalkyl having a saturated carbocyclic ring containing 3 to 7 carbon atoms,
  (3) hydroxy,
  (4) amino,
  (5) cyano,
  (6) nitro,
  (7) carboxy,
  (8) alkoxy having 1 to 6 carbon atoms,
  (9) alkylthio having 1 to 6 carbon atoms,
  (10) alkoxycarbonyl, wherein the alkoxy thereof has 1 to 6 carbon atoms,
  (11) aryloxycarbonyl having 7 to 13 carbon atoms,
  (12) alkyloxycarbonylamino, wherein the alkyloxy thereof has 1 to 6 carbon atoms,
  (13) alkylamino having 1 to 4 carbon atoms,
  (14) dialkylamino having 2 to 8 carbon atoms,
  (5) saturated monocyclic heterocycle comprising not more than 6 carbon atoms and one or two hetero atoms selected from the group consisting of nitrogen, oxygen and sulfur,
  (16) aryl having up to 10 carbon atoms,
  (17) aryl having up to 10 carbon atoms and one or more substituents selected from the group consisting of:
    (i) halogen,
    (ii) alkyl having 1 to 10 carbon atoms, (iii) alkoxy having 1 to 6 carbon atoms,
(iv) nitro,
(v) cyano,
(vi) carboxy,
(vii) hydroxy,
(viii) amino,
(ix) trifluoromethyl,
(x) alkylamino having 1 to 4 carbon atoms,
(xi) dialkylamino having 2 to 8 carbon atoms,
(xii) alkanoyl having 1 to 6 carbon atoms,
(xiii) alkanoylamino having 1 to 6 carbon atoms,
(xiv) sulfamoyl,
(xv) alkylaminosulfonyl, wherein the alkylamino thereof has 1 to 4 carbon atoms,
(xvi) dialkylaminosulfonyl, wherein the dialkylamino thereof has 2 to 8 carbon atoms and
(xvii) alkoxycarbonyl, wherein the alkoxy thereof has 1 to 6 carbon atoms, or
(xviii) substituents which are combined to form methylenedioxy, ethylenedioxy or dihydroxyfuran or
(18) unsaturated aromatized monocyclic or bicyclic heterocycle comprising not more than 9 carbon atoms and 1 to 3 hetero atoms selected from the group consisting of nitrogen, oxygen and sulfur;

$R^2$ is hydrogen, alkyl having 1 to 10 carbon atoms or aryl having up to 10 carbon atoms; and $R^3$ is:
(a) alkyl having 1 to 10 carbon atoms,
(b) aryl having up to 10 carbon atoms,
(c) aryl having up to 10 carbon atoms and one or more substituents selected from the group consisting of:
  (1) halogen,
  (2) alkyl having 1 to 10 carbon atoms,
  (3) alkoxy having 1 to 6 carbon atoms,
  (4) nitro,
  (5) cyano,
  (6) carboxy,
  (7) hydroxy,
  (8) amino,
  (9) trifluoromethyl,
  (10) alkylamino having 1 to 4 carbon atoms,
  (11) dialkylamino having 2 to 8 carbon atoms,
  (12) alkanoyl having 1 to 6 carbon atoms,
  (13) alkanoylamino having 1 to 6 carbon atoms,
  (14) sulfamoyl,
  (15) alkylaminosulfonyl, wherein the alkylamino thereof has 1 to 4 carbon atoms,
  (16) dialkylaminosulfonyl, wherein the dialkylamino thereof has 2 to 8 carbon atoms and
  (17) alkoxycarbonyl, wherein the alkoxy thereof has 1 to 6 carbon atoms, or
  (18) substituents which are combined to form methylenedioxy, ethylenedioxy or dihydroxyfuran,
(d) unsaturated aromatized monocyclic or bicyclic heterocycle comprising not more than 9 carbon atoms and 1 to 3 hetero atoms selected from the group consisting of nitrogen, oxygen and sulfur or
(e) —$(CH_2)_{m1}$-$A^1$, wherein m1 is an integer selected from the group consisting of 1, 2, 3 and 4, and $A^1$ is:
  (1) halogen,
  (2) cycloalkyl having a saturated carbocyclic ring containing 3 to 7 carbon atoms,
  (3) hydroxy,
  (4) amino,
  (5) cyano,
  (6) nitro,
  (7) carboxy,
  (8) alkoxy having 1 to 6 carbon atoms,
  (9) alkylthio having 1 to 6 carbon atoms,
  (10) alkoxycarbonyl, wherein the alkoxy thereof has 1 to 6 carbon atoms,
  (11) aryloxycarbonyl having 7 to 13 carbon atoms,
  (12) alkyloxycarbonylamino, wherein the alkyloxy thereof has 1 to 6 carbon atoms,
  (13) alkylamino having 1 to 4 carbon atoms,
  (14) dialkylamino having 2 to 8 carbon atoms,
  (15) saturated monocyclic heterocycle comprising not more than 6 carbon atoms and one or two hetero atoms selected from the group consisting of nitrogen, oxygen and sulfur,
  (16) aryl having up to 10 carbon atoms,
  (17) aryl having up to 10 carbon atoms and one or more substituents selected from the group consisting of:
    (i) halogen,
    (ii) alkyl having 1 to 10 carbon atoms,
    (iii) alkoxy having 1 to 6 carbon atoms,
    (iv) nitro,
    (v) cyano,
    (vi) carboxy,
    (vii) hydroxy,
    (viii) amino,
    (ix) trifluoromethyl,
    (x) alkylamino having 1 to 4 carbon atoms,
    (xi) dialkylamino having 2 to 8 carbon atoms,
    (xii) alkanoyl having 1 to 6 carbon atoms,
    (xiii) alkanoylamino having 1 to 6 carbon atoms,
    (xiv) sulfamoyl,
    (xv) alkylaminosulfonyl, wherein the alkylamino thereof has 1 to 4 carbon atoms,
    (xvi) dialkylaminosulfonyl, wherein the dialkylamino thereof has 2 to 8 carbon atoms and
    (xvii) alkoxycarbonyl, wherein the alkoxy thereof has 1 to 6 carbon atoms, or
    (xviii) substituents which are combined to form methylenedioxy, ethylenedioxy or dihydroxyfuran or
  (18) unsaturated aromatized monocyclic or bicyclic heterocycle comprising not more than 9 carbon atoms and 1 to 3 hetero atoms selected from the group consisting of nitrogen, oxygen and sulfur, or a pharmaceutically acceptable salt thereof.

2. A compound represented by formula (1-a), (1-a)

wherein $X^1$ is amino or hydroxy;

$X^2$ is carbonyl (—(CO)—), carbonyloxy (—(CO)O—), carbonylamino (—(CO)NH—), or sulfonyl(—(SO$_2$)—);

$R^1$ is:
(a) alkyl having 1 to 10 carbon atoms,
(b) cycloalkyl having a saturated carbocyclic ring containing 3 to 7 carbon atoms,
(c) aryl having up to 10 carbon atoms,
(d) aryl having up to 10 carbon atoms and one or more substituents selected from the group consisting of
  (1) halogen,
  (2) alkyl having 1 to 10 carbon atoms,
  (3) alkoxy having 1 to 6 carbon atoms,
  (4) nitro,
  (5) cyano,
  (6) carboxy,
  (7) hydroxy,
  (8) amino,
  (9) trifluoromethyl,
  (10) alkylamino having 1 to 4 carbon atoms,
  (11) dialkylamino having 2 to 8 carbon atoms,
  (12) alkanoyl having 1 to 6 carbon atoms,
  (13) alkanoylamino having 1 to 6 carbon atoms,
  (14) sulfamoyl,
  (15) alkylaminosulfonyl, wherein the alkylamino thereof has 1 to 4 carbon atoms,
  (16) dialkylaminosulfonyl, wherein the dialkylamino thereof has 2 to 8 carbon atoms and
  (17) alkoxycarbonyl, wherein the alkoxy thereof has 1 to 6 carbon atoms, or
  (18) substituents which are combined to from methylenedioxy, ethylenedioxy or dihydroxyfuran,
(e) unsaturated aromatized monocyclic or bicyclic heterocycle comprising not more than 9 carbon atoms and 1 to 3 hetero atoms selected from the group consisting of nitrogen, oxygen and sulfur, or
(f) —(CH$_2$)$_m$-A, wherein m is an integer selected from the group consisting of 1, 2, 3, 4, 5, 6, 7, 8, 9 and 10, and A is:
  (1) halogen,
  (2) cycloalkyl having a saturated carbocyclic ring containing 3 to 7 carbon atoms,
  (3) hydroxy,
  (4) amino,
  (5) cyano,
  (6) nitro,
  (7) carboxy,
  (8) alkoxy having 1 to 6 carbon atoms,
  (9) alkylthio having 1 to 6 carbon atoms,
  (10) alkoxycarbonyl, wherein the alkoxy thereof has 1 to 6 carbon,
  (11) aryloxycarbonyl having 7 to 13 carbon atoms,
  (12) alkyloxycarbonylamino, wherein the alkyloxy thereof has 1 to 6 carbon atoms,
  (13) alkylamino having 1 to 4 carbon atoms,
  (14) dialkylamino having 2 to 8 carbon atoms,
  (15) saturated monocyclic heterocycle comprising not more than 6 carbon atoms and one or two hetero atoms selected from the group consisting of nitrogen, oxygen and sulfur,
  (16) aryl having up to 10 carbon atoms,
  (17) aryl having up to 10 carbon atoms and one or more substituents selected from the group consisting of:
    (i) halogen,
    (ii) alkyl having 1 to 10 carbon atoms,
    (iii) alkoxy having 1 to 6 carbon atoms,
    (iv) nitro,
    (v) cyano,
    (vi) carboxy,
    (vii) hydroxy,
    (viii) amino,
    (ix) trifluoromethyl,
    (x) alkylamino having 1 to 4 carbon atoms,
    (xi) dialkylamino having 2 to 8 carbon atoms,
    (xii) alkanoyl having 1 to 6 carbon atoms,
    (xiii) alkanoylamino having 1 to 6 carbon atoms,
    (xiv) sulfamoyl,
    (xv) alkylaminosulfonyl, wherein the alkylamino thereof has 1 to 4 carbon atoms,
    (xvi) dialkylaminosulfonyl, wherein the dialkylamino thereof has 2 to 8 carbon atoms and
    (xvii) alkoxycarbonyl, wherein the alkoxy thereof has 1 to 6 carbon atoms, or
    (xviii) substituents which are combined to form methylenedioxy, ethylenedioxy, or dihydroxyfuran or
  (18) unsaturated aromatized monocyclic or bicyclic heterocycle comprising not more than 9 carbon atoms and 1 to 3 hetero atoms selected from the group consisting of nitrogen, oxygen and sulfur;
$R^2$ is hydrogen, alkyl having 1 to 10 carbon atoms or aryl having up to 10 carbon atoms; and
$R^3$ is:
(a) alkyl having 1 to 10 carbon atoms,
(b) aryl having up to 10 carbon atoms,
(c) aryl having up to 10 carbon atoms and one or more substituents selected from the group consisting of:
  (1) halogen atom,
  (2) alkyl having 1 to 10 carbon atoms,
  (3) alkoxy having 1 to 6 carbon atoms,
  (4) nitro,
  (5) cyano,
  (6) carboxy,
  (7) hydroxy,
  (8) amino,
  (9) trifluoromethyl,
  (10) alkylamino having 1 to 4 carbon atoms,
  (11) dialkylamino having 2 to 8 carbon atoms,
  (12) alkanoyl having 1 to 6 carbon atoms,
  (13) alkanoylamino having 1 to 6 carbon atoms,
  (14) sulfamoyl,
  (15) ukylaminosuyflny, wherein the alkylamino thereof has 1 to 4 carbon atoms,
  (16) dialkylaminosulfonyl, wherein the dialkylamino thereof has 2 to 8 carbon atoms and
  (17) alkoxycarbonyl, wherein the alkoxy thereof has 1 to 6 carbon atoms, or
  (18) substituents which are combined to form methylenedioxy, ethylenedioxy or dihydroxyfuran,
(d) unsaturated aromatized monocyclic or bicyclic heterocycle comprising not more than 9 carbon atoms and 1 to 3 hetero atoms selected from the group consisting of nitrogen, oxygen and sulfur, or
(e) —(CH$_2$)m$_1$-A$^1$, wherein m1 is an integer selected from the group consisting of 1, 2, 3 and 4, and A$^1$ is:
  (1) halogen,
  (2) cycloalkyl having a saturated carbocyclic ring containing 3 to 7 carbon atoms,
  (3) hydroxy,
  (4) amino,
  (5) cyano,
  (6) nitro,
  (7) carboxy,
  (8) alkoxy having 1 to 6 carbon atoms, (9) alkylthio having 1 to 6 carbon atoms,
(10) alkoxycarbonyl, wherein the alkoxy thereof has 1 to 6 carbon atoms,
(11) aryloxycarbonyl having 7 to 13 carbon atoms,
(12) alkyloxycarbonylamino, wherein the alkyloxy thereof has 1 to 6 carbon atoms,
(13) alkylamino having 1 to 4 carbon atoms,
(14) dialkylamino having 2 to 8 carbon atoms,
(15) saturated monocyclic heterocycle comprising not more than 6 carbon atoms and one or two hetero atoms selected from the group consisting of nitrogen, oxygen and sulfur,
(16) aryl having up to 10 carbon atoms,
(17) aryl having up to 10 carbon atoms and one or more substituents selected from the group consisting of:
  (i) halogen,
  (ii) alkyl having 1 to 10 carbon atoms,
  (iii) alkoxy having 1 to 6 carbon atoms,
  (iv) nitro,
  (v) cyano,
  (vi) carboxy,
  (vii) hydroxy,
  (viii) amino,
  (ix) trifluoromethyl,
  (x) alkylamino having 1 to 4 carbon atoms,
  (xi) dialkylamino having 2 to 8 carbon atoms,
  (xii) alkanoyl having 1 to 6 carbon atoms,
  (xiii) alkanoylamino having 1 to 6 carbon atoms,
  (xiv) sulfamoyl,
  (xv) alkylaminosulfonyl, wherein the alkylamino thereof has 1 to 4 carbon atoms,
  (xvi) dialkylaminosulfonyl, wherein the dialkylamino thereof has 2 to 8 carbon atoms and
  (xvii) alkoxycarbonyl, wherein the alkoxy thereof has 1 to 6 carbon atoms, or
  (xviii) substituents which are combined to form methylenedioxy, ethylenedioxy or dihydroxyfuran or
(18) unsaturated aromatized monocyclic or bicyclic heterocycle comprising not more than 9 carbon atoms and 1 to 3 hetero atoms selected from the group consisting of nitrogen, oxygen and sulfur,
or a pharmaceutically acceptable salt thereof.

3. The compound of claim 2, wherein $X^1$ is amino.

4. The compound of claim 2,
wherein
$X^1$ is amino;
$X^2$ is carbonyl (—(CO)—), carbonyloxy (—(CO)O—) or carbonylamino (—(CO)NH—);
$R^1$ is
  (a) cycloalkyl having a saturated carbocyclic ring containing 3 to 7 carbon atoms,
  (b) aryl having up to 10 carbon atoms,
  (c) aryl having up to 10 carbon atoms and one or more substituents selected from the group consisting of:
    (1) halogen,
    (2) alkyl having 1 to 10 carbon atoms,
    (3) alkoxy having 1 to 6 carbon atoms,
    (4) nitro,
    (5) cyano,
    (6) carboxy,
    (7) hydroxy,
    (8) amino,
    (9) trifluoromethyl,
    (10) alkylamino having 1 to 4 carbon atoms,
    (11) dialkylamino having 2 to 8 carbon atoms,
    (12) alkanoyl having 1 to 6 carbon atoms,
    (13) alkanoylamino having 1 to 6 carbon atoms,
    (14) sulfamoyl,
    (15) alkylaminosulfonyl, wherein the alkylamino thereof has 1 to 4 carbon atoms,
    (16) dialkylaminosulfonyl, wherein the dialkylamino thereof has 2 to 8 carbon atoms and
    (17) alkoxycarbonyl, wherein the alkoxy thereof has 1 to 6 carbon atoms, or
    (18) substituents which are combined to form methylenedioxy, ethylenedioxy or dihydroxyfuran,
  (d) unsaturated aromatized monocyclic or bicyclic heterocycle comprising not more than 9 carbon atoms and 1 to 3 hetero atoms selected from the group consisting of nitrogen, oxygen and sulfur or
  (e) —(CH$_2$)$_m$-A, wherein m is an integer selected from the group of 1, 2, 3, 4, 5, 6, 7, 8, 9 and 10, and A is:
    (1) halogen,
    (2) cycloalkyl having a saturated carbocyclic ring containing 3 to 7 carbon atoms,
    (3) hydroxy,
    (4) amino,
    (5) cyano,
    (6) nitro,
    (7) carboxy,
    (8) alkoxy having 1 to 6 carbon atoms,
    (9) alkylthio having 1 to 6 carbon atoms,
    (10) alkoxycarbonyl, wherein the alkoxy portion has 1 to 6 carbon atoms,
    (11) aryloxycarbonyl having 7 to 13 carbon atoms,
    (12) alkyloxycarbonylamino, wherein the alkyloxy portion has 1 to 6 carbon atoms,
    (13) alkylamino having 1 to 4 carbon atoms,
    (14) dialkylamino having 2 to 8 carbon atoms,
    (15) saturated monocyclic heterocycle comprising not more than 6 carbon atoms and one or two hetero atoms selected from the group consisting of nitrogen, oxygen and sulfur,
    (16) aryl having up to 10 carbon atoms,
    (17) aryl having up to 10 carbon atoms and one or more substituents selected from the group consisting of
      (i) halogen,
      (ii) alkyl having 1 to 10 carbon atoms,
      (iii) alkoxy having 1 to 6 carbon atoms,
      (iv) nitro,
      (v) cyano,
      (vi) carboxy,
      (vii) hydroxy,
      (viii) amino,
      (ix) trifluoromethyl,
      (x) alkylamino having 1 to 4 carbon atoms,
      (xi) dialkylamino having 2 to 8 carbon atoms,
      (xii) alkanoyl having 1 to 6 carbon atoms,
      (xiii) alkanoylamino having 1 to 6 carbon atoms,
      (xiv) sulfamoyl,
      (xv) alkylaminosulfonyl, wherein the alkylamino thereof has 1 to 4 carbon atoms,
      (xvi) dialkylaminosulfonyl, wherein the dialkylamino thereof has 2 to 8 carbon atoms and
      (xvii) alkoxycarbonyl, wherein the alkoxy thereof has 1 to 6 carbon atoms, or
      (xviii) substituents which are combined to form methylenedioxy, ethylenedioxy or dihydroxyfuran, or
    (18) unsaturated aromatized monocyclic or bicyclic heterocycle comprising not more than 9 carbon atoms and 1 to 3 hetero atoms selected from the group consisting of nitrogen, oxygen and sulfur;

$R^2$ is hydrogen, alkyl having 1 to 10 carbon atoms or aryl having up to 10 carbon atoms; and $R^3$ is
(a) alkyl having 1 to 10 carbon atoms,
(b) aryl having up to 10 carbon atoms,
(c) aryl having up to 10 carbon atoms and one or more substituents selected from the group consisting of:
  (1) halogen,
  (2) alkyl having 1 to 10 carbon atoms,
  (3) alkoxy having 1 to 6 carbon atoms,
  (4) nitro,
  (5) cyano,
  (6) carboxy,
  (7) hydroxy,
  (8) amino,
  (9) trifluoromethyl,
  (10) alkylamino having 1 to 4 carbon atoms,
  (11) dialkylamino having 2 to 8 carbon atoms,
  (12) alkanoyl having 1 to 6 carbon atoms,
  (13) alkanoylamino having 1 to 6 carbon atoms,
  (14) sulfamoyl,
  (15) alkylaminosulfonyl, wherein the alkylamino thereof has 1 to 4 carbon atoms,
  (16) dialkylaminosulfonyl, wherein the dialkylamino thereof has 2 to 8 carbon atoms and
  (17) alkoxycarbonyl, wherein the alkoxy thereof has 1 to 6 carbon atoms, or
  (18) substituents which are combined together to form methylenedioxy, ethylenedioxy or dihydroxyfuran,
(d) unsaturated aromatized monocyclic or bicyclic heterocycle comprising not more than 9 carbon atoms and 1 to 3 hetero atoms selected from the group consisting of nitrogen, oxygen and sulfur atom or
(e) —$(CH_2)_{m1}$-$A^1$, wherein m1 is an integer selected from the group consisting of 1, 2, 3 and 4, and $A^1$ is:
  (1) halogen,
  (2) cycloalkyl having a saturated carbocyclic ring containing 3 to 7 carbon atoms,
  (3) hydroxy,
  (4) amino,
  (5) cyano,
  (6) nitro,
  (7) carboxy,
  (8) alkoxy having 1 to 6 carbon atoms,
  (9) alkylthio alkoxy having 1 to 6 carbon atoms,
  (10) alkoxycarbonyl, wherein the alkoxy thereof has 1 to 6 carbon atoms,
  (11) aryloxycarbonyl having 7 to 13 carbon atoms,
  (12) alkyloxycarbonylamino, wherein the alkyloxy thereof has 1 to 6 carbon atoms,
  (13) alkylamino having 1 to 4 carbon atoms,
  (14) dialkylamino having 2 to 8 carbon atoms,
  (15) saturated monocyclic heterocycle comprising not more than 6 carbon atoms and one or two hetero atoms selected from the group consisting of nitrogen, oxygen and sulfur,
  (16) aryl having up to 10 carbon atoms,
  (17) aryl having up to 10 carbon atoms and one or more substituents selected from the group consisting of:
    (i) halogen,
    (ii) alkyl having 1 to 10 carbon atoms,
    (iii) alkoxy having 1 to 6 carbon atoms,
    (iv) nitro,
    (v) cyano,
    (vi) carboxy,
    (vii) hydroxy
    (viii) amino,
    (ix) trifluoromethyl,
    (x) alkylamino having 1 to 4 carbon atoms,
    (xi) dialkylamino having 2 to 8 carbon atoms,
    (xii) alkanoyl having 1 to 6 carbon atoms,
    (xiii) alkanoylamino having 1 to 6 carbon atoms,
    (xiv) sulfamoyl,
    (xv) alkylaminosulfonyl, wherein the alkylamino thereof has 1 to 4 carbon atoms,
    (xvi) dialkylaminosulfonyl, wherein the dialkylamino thereof has 2 to 8 carbon atoms and
    (xvii) alkoxycarbonyl, wherein the alkoxy thereof has 1 to 6 carbon atoms, or
    (xviii) substituents which are combined to form methylenedioxy, ethylenedioxy or dihydroxyfuran, or
  (18) unsaturated aromatized monocyclic or bicyclic heterocycle comprising not more than 9 carbon atoms and 1 to 3 hetero atoms selected from the group consisting of nitrogen, oxygen and sulfur atom.

5. The compound of claim 4, wherein $X^2$ is carbonyl (—(CO)—) or carbonylamino (—(CO)NH—).

6. The compound of claim 4, wherein $X^2$ is carbonyl (—(CO)—).

7. A compound represented by formula (1-e)

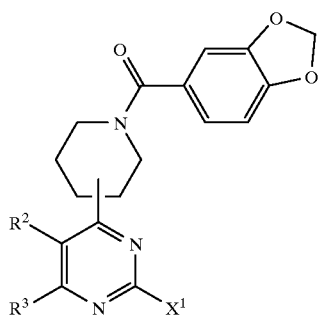

(1-e)

wherein $X^1$ is amino or hydroxy;

$R^2$ is hydrogen, alkyl having 1 to 10 carbon atoms or aryl having up to 10 carbon atoms; and $R^3$ is:
(a) alkyl having 1 to 10 carbon atoms,
(b) aryl having up to 10 carbon atoms,
(c) aryl having up to 10 carbon atoms and one or more substituents selected from the group consisting of:
  (1) halogen,
  (2) alkyl having 1 to 10 carbon atoms,
  (3) alkoxy having 1 to 6 carbon atoms,
  (4) nitro,
  (5) cyano,
  (6) carboxy,
  (7) hydroxy,
  (8) amino,
  (9) trifluoromethyl,
  (10) alkylamino having 1 to 4 carbon atoms,
  (11) dialkylamino having 2 to 8 carbon atoms,
  (12) alkanoyl having 1 to 6 carbon atoms,
  (13) alkanoylamino having 1 to 6 carbon atoms,

(14) sulfamoyl,
(15) alkylaminosulfonyl, wherein the alkylamino thereof has 1 to 4 carbon atoms,
(16) dialkylaminosulfonyl, wherein the dialkylamino thereof has 2 to 8 carbon atoms and
(17) alkoxycarbonyl, wherein the alkoxy thereof has 1 to 6 carbon atoms, or
(18) substituents which are combined to form methylenedioxy, ethylenedioxy or dihydroxyftiran,
(d) unsaturated aromatized monocyclic or bicyclic heterocycle comprising not more than 9 carbon atoms and 1 to 3 hetero atoms selected from the group consisting of nitrogen, oxygen and sulfur or
(e) —$(CH_2)_{m1}$-$A^1$, wherein m1 is an integer selected from the group consisting of 1, 2, 3 and 4, and $A^1$ is:
(1) halogen,
(2) cycloalkyl having a saturated carbocyclic ring containing 3 to 7 carbon atoms,
(3) hydroxy,
(4) amino,
(5) cyano,
(6) nitro,
(7) carboxy,
(8) alkoxy having 1 to 6 carbon atoms,
(9) alkylthio having 1 to 6 carbon atoms,
(10) alkoxycarbonyl, wherein the alkoxy thereof has 1 to 6 carbon atoms,
(11) aryloxycarbonyl having 7 to 13 carbon atoms,
(12) alkyloxycarbonylamino, wherein the alkyloxy thereof has 1 to 6 carbon atoms,
(13) alkylamino having 1 to 4 carbon atoms,
(14) dialkylamino having 2 to 8 carbon atoms,
(15) saturated monocyclic heterocycle comprising not more than 6 carbon atoms and one or two hetero atoms selected from the group consisting of nitrogen, oxygen and sulfur,
(16) aryl having up to 10 carbon atoms,
(17) aryl having up to 10 carbon atoms and one or more substituents selected from the group consisting of:
(i) halogen,
(ii) alkyl having 1 to 10 carbon atoms,
(iii) alkoxy having 1 to 6 carbon atoms,
(iv) nitro,
(v) cyano,
(vi) carboxy,
(vii) hydroxy,
(viii) amino,
(ix) trifluoromethyl,
(x) alkylamino having 1 to 4 carbon atoms,
(xi) dialkylamino having 2 to 8 carbon atoms,
(xii) alkanoyl having 1 to 6 carbon atoms,
(xiii) alkanoylamino having 1 to 6 carbon atoms,
(xiv) sulfamoyl,
(xv) alkylaminosulfonyl, wherein the alkylamino thereof has 1 to 4 carbon atoms,
(xvi) dialkylaminosulfonyl, wherein the dialkylamino thereof has 2 to 8 carbon atoms and
(xvii) alkoxycarbonyl, wherein the alkoxy thereof has 1 to 6 carbon atoms, or
(xviii) substituents which are combined to form methylenedioxy, ethylenedioxy or dihydroxyfuran or
(18) unsaturated aromatized monocyclic or bicyclic heterocycle comprising not more than 9 carbon atoms and 1 to 3 hetero atoms selected from the group consisting of nitrogen, oxygen and sulfur, or a pharmaceutically acceptable salt thereof.

8. A compound represented by formula (1-b)

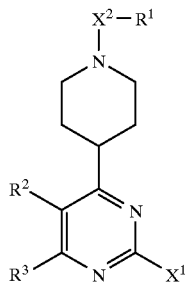

(1-b)

wherein $X^1$ is amino;

$X^2$ is carbonyl (—(CO)—), carbonyloxy (—(CO)O—) or carbonylamino (—(CO)NH—);

$R^1$ is:
(a) alkyl having 1 to 10 carbon atoms,
(b) cycloalkyl having a saturated carbocyclic ring containing 3 to 7 carbon atoms,
(c) aryl having up to 10 carbon atoms,
(d) aryl having up to 10 carbon atoms and one or more substituents selected from the group consisting of:
(1) halogen,
(2) alkyl having 1 to 10 carbon atoms,
(3) alkoxy having 1 to 6 carbon atoms,
(4) nitro,
(5) cyano,
(6) carboxy,
(7) hydroxy,
(8) amino,
(9) trifluoromethyl,
(10) alkylamino having 1 to 4 carbon atoms,
(11) dialkylamino having 2 to 8 carbon atoms,
(12) alkanoyl having 1 to 6 carbon atoms,
(13) alkanoylamino having 1 to 6 carbon atoms,
(14) sulfamoyl,
(15) alkylaminosulfonyl, wherein the alkylamino thereof has 1 to 4 carbon atoms,
(16) dialkylaminosulfonyl, wherein the dialkylamino thereof has 2 to 8 carbon atoms and
(17) alkoxycarbonyl, wherein the alkoxy thereof has 1 to 6 carbon atoms, or
(18) substituents which are combined to form methylenedioxy, ethylenedioxy or dihydroxyfuran,
(e) unsaturated aromatized monocyclic or bicyclic heterocycle comprising not more than 9 carbon atoms and 1 to 3 hetero atoms selected from the group consisting of nitrogen, oxygen and sulfur or
(f) —$(CH_2)_m$-A, wherein m is an integer selected from the group consisting of 1, 2, 3, 4, 5, 6, 7, 8, 9 and 10, and A is:
(1) halogen,
(2) cycloalkyl having a saturated carbocyclic ring containing 3 to 7 carbon atoms,
(3) hydroxy,
(4) amino,
(5) cyano,
(6) nitro,
(7) carboxy,
(8) alkoxy having 1 to 6 carbon atoms,
(9) alkylthio having 1 to 6 carbon atoms,

(10) alkoxycarbonyl, wherein the alkoxy thereof has 1 to 6 carbon atoms,
(11) aryloxycarbonyl having 7 to 13 carbon atoms,
(12) alkyloxycarbonylamino, wherein the alkyloxy thereof has 1 to 6 carbon atoms,
(13) alkylamino having 1 to 4 carbon atoms,
(14) dialkylamino having 2 to 8 carbon atoms,
(15) saturated monocyclic heterocycle comprising not more than 6 carbon atoms and one or two hetero atoms selected from the group consisting of nitrogen, oxygen and sulfur,
(16) aryl having up to 10 carbon atoms,
(17) aryl having up to 10 carbon atoms and one or more substituents selected from the group consisting of:
  (i) halogen,
  (ii) alkyl having 1 to 10 carbon atoms,
  (iii) alkoxy having 1 to 6 carbon atoms,
  (iv) nitro,
  (v) cyano,
  (vi) carboxy,
  (vii) hydroxy,
  (viii) amino,
  (ix) trifluoromethyl,
  (x) alkylamino having 1 to 4 carbon atoms,
  (xi) dialkylamino having 2 to 8 carbon atoms,
  (xii) alkanoyl having 1 to 6 carbon atoms,
  (xiii) alkanoylamino having 1 to 6 carbon atoms,
  (xiv) sulfamoyl,
  (xv) alkylaminosulfonyl, wherein the alkylamino thereof has 1 to 4 carbon atoms,
  (xvi) dialkylaminosulfonyl, wherein the dialkylamino thereof has 2 to 8 carbon atoms and
  (xvii) alkoxycarbonyl, wherein the alkoxy thereof has 1 to 6 carbon atoms, or
  (xviii) substituents which are combined to form methylenedioxy, ethylenedioxy or dihydroxyfuran or
(18) unsaturated aromatized monocyclic or bicyclic heterocycle comprising not more than 9 carbon atoms and 1 to 3 hetero atoms selecting from the group consisting of nitrogen, oxygen and sulfur;

$R^2$ is hydrogen or alkyl having 1 to 10 carbon atoms; and
$R^3$ is:
(a) aryl having up to 10 carbon atoms,
(b) aryl having up to 10 carbon atoms and one or more substituents selected from the group consisting of:
  (1) halogen,
  (2) alkyl having 1 to 10 carbon atoms,
  (3) alkoxy having 1 to 6 carbon atoms,
  (4) nitro,
  (5) cyano,
  (6) carboxy,
  (7) hydroxy,
  (8) amino,
  (9) trifluoromethyl,
  (10) alkylamino having 1 to 4 carbon atoms,
  (11) dialkylamino having 2 to 8 carbon atoms,
  (12) alkanoyl having 1 to 6 carbon atoms,
  (13) alkanoylamino having 1 to 6 carbon atoms,
  (14) sulfamoyl,
  (15) alkylaminosulfonyl, wherein the alkylamino thereof has 1 to 4 carbon atoms,
  (16) dialkylaminosulfonyl, wherein the dialkylamino thereof has 2 to 8 carbon atoms and
  (17) alkoxycarbonyl, wherein the alkoxy thereof has 1 to 6 carbon atoms, or
  (18) substituents which are combined to form methylenedioxy, ethylenedioxy or dihydroxyfuran,
(c) unsaturated aromatized monocyclic or bicyclic heterocycle comprising not more than 9 carbon atoms and 1 to 3 hetero atoms selected from the group consisting of nitrogen, oxygen and sulfur or
(d) —$(CH_2)_{m1}$-$A^1$, wherein m1 is an integer selected from the group consisting of 1 and 2, and $A^1$ is:
  (1) aryl having up to 10 carbon atoms,
  (2) aryl having up to 10 carbon atoms and one or more substituents selected from the group consisting of:
    (i) halogen,
    (ii) alkyl having 1 to 10 carbon atoms,
    (iii) alkoxy having 1 to 6 carbon atoms,
    (iv) nitro,
    (v) cyano,
    (vi) carboxy,
    (vii) hydroxy,
    (viii) amino,
    (ix) trifluoromethyl,
    (x) alkylamino having 1 to 4 carbon atoms,
    (xi) dialkylamino having 2 to 8 carbon atoms,
    (xii) alkanoyl having 1 to 6 carbon atoms,
    (xiii) alkanoylamino having 1 to 6 carbon atoms,
    (xiv) sulfamoyl,
    (xv) alkylaminosulfonyl, wherein the alkylamino thereof has 1 to 4 carbon atoms,
    (xvi) dialkylaminosulfonyl, wherein the dialkylamino thereof has 2 to 8 carbon atoms and
    (xvii) alkoxycarbonyl, wherein the alkoxy thereof has 1 to 6 carbon atoms, or
    (xviii) substituents which are combined to form methylenedioxy, ethylenedioxy or dihydroxyfuran, or
  (3) unsaturated aromatized monocyclic or bicyclic heterocycle comprising not more than 9 carbon atoms and 1 to 3 hetero atoms selected from the group consisting of nitrogen, oxygen and sulfur, or a pharmaceutically acceptable salt thereof.

\* \* \* \* \*